(12) United States Patent
Lyons et al.

(10) Patent No.: US 7,985,543 B2
(45) Date of Patent: Jul. 26, 2011

(54) TEST FOR DETERMINING BLOOD TYPE IN THE CAT

(75) Inventors: Leslie A. Lyons, Woodland, CA (US); Niels C. Pedersen, Winters, CA (US); Barbara Bighignoli, Milan (IT); Tirri Niini, Espoo (FI)

(73) Assignee: The Regents of the University of California, Oakland, CA (US)

( * ) Notice: Subject to any disclaimer, the term of this patent is extended or adjusted under 35 U.S.C. 154(b) by 280 days.

(21) Appl. No.: 11/963,220

(22) Filed: Dec. 21, 2007

(65) Prior Publication Data

US 2008/0220427 A1  Sep. 11, 2008

Related U.S. Application Data

(60) Provisional application No. 60/876,721, filed on Dec. 21, 2006.

(51) Int. Cl.
*C07H 21/04* (2006.01)
*C12Q 1/68* (2006.01)

(52) U.S. Cl. ......... 435/6; 435/91.1; 435/91.2; 536/23.1; 536/24.3

(58) Field of Classification Search .................. None
See application file for complete search history.

(56) References Cited

OTHER PUBLICATIONS

Bigthigno et al. BMC Genetics, vol. 8, No. 27, pp. 1-10, 2007.*
Ando, N., et al., "On the Minor Gangliosides of Erythrocyte Membranes," *J. Biochem* (Tokyo), 91:873-881 (1982).
Andrews, G.A., et al., "N-Glycolylneuraminic Acid and N-Acetylneuraminic Acid Define Feline Blood Group A and B Antigens," *Blood*, 79(9):2485-2491 (May 1, 1992).
Furukawa, K., et al., "Identification of N-Glycolylneuraminic Acid-containing Gangliosides of Cat and Sheep Erythrocytes," *J. Biol. Chem.*, 263:14939-14947 (1988).
Hamanaka, S., et al., "Occurrence of Hematoside with Two Moles of N-Acetyl-neuraminic Acid in a Certain Breed of Persian Cat," *J. Biochem.*, 86:695-698 (1979).
Griot-Wenk, M., et al., "Biochemical characterization of the feline AB blood group system," *Animal Genetics*, 24:401-407 (1993).

* cited by examiner

*Primary Examiner* — Jeanine A Goldberg
(74) *Attorney, Agent, or Firm* — Kilpatrick Townsend & Stockton LLP

(57) ABSTRACT

The present invention provides compositions and methods for detecting mutations associated with blood type determination in the cat.

5 Claims, 17 Drawing Sheets

Cat breeds with different frequencies of the type A and type B blood groups

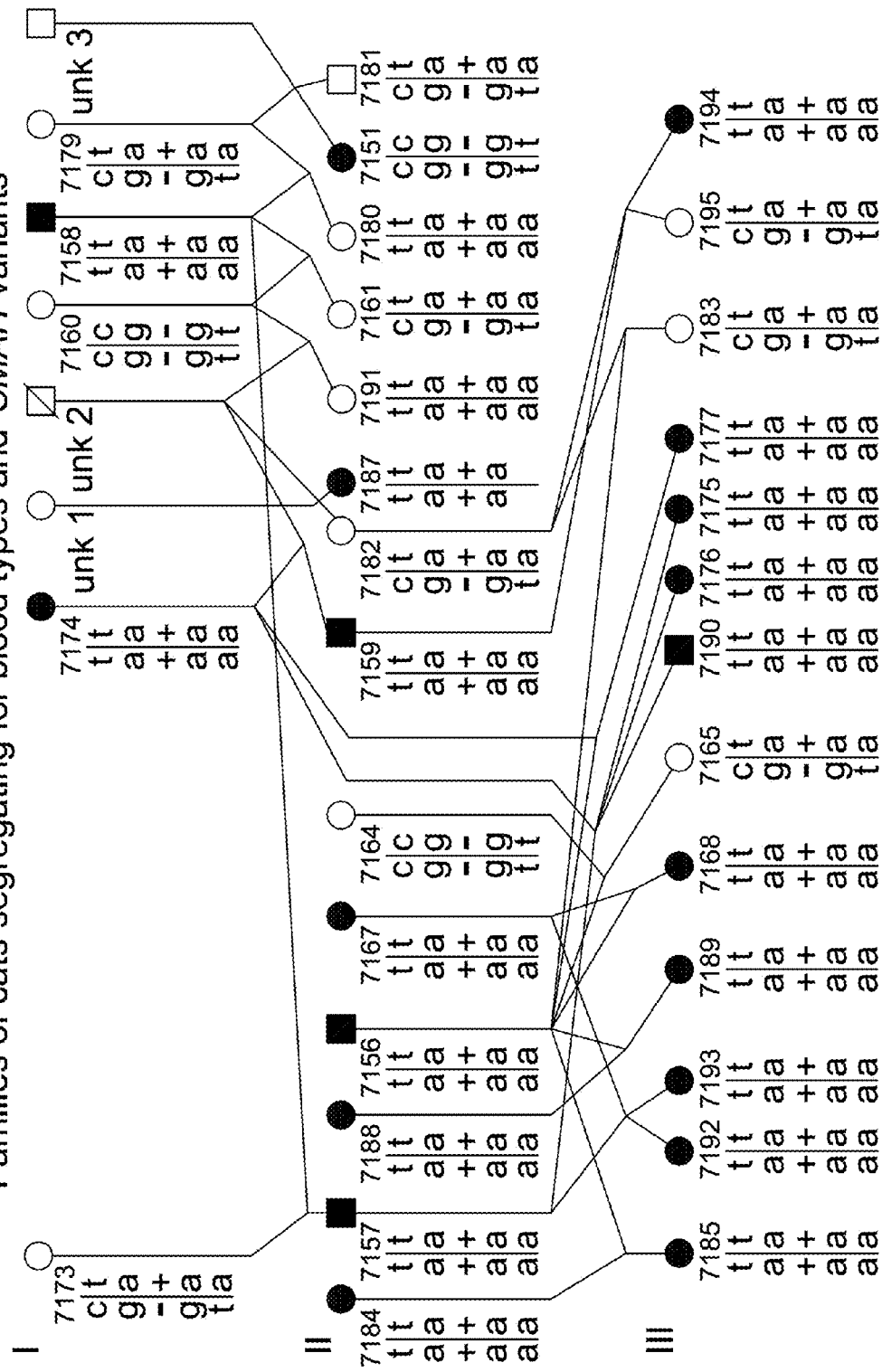

Families of cats segregating for blood types and *CMAH* variants

Fig. 3 (sheet 1)

Sequence and protein translation of feline CMAH

1: (SEQ·ID·NO:3)
2: (SEQ·ID·NO:1)
3: (SEQ·ID·NO:59)
4: (SEQ·ID·NO:60)
5: (SEQ·ID·NO:61)

| | 1........10........20........30........40........50........60........70...... |
|---|---|
| 1:Protein | M G S I E Q T T E V L L C L S P G E A A D L K E G |
| 2:Cat | ATGGGCAGCATTGAACAGACGACGGAGGTCTTGTTGTGTCACCTGGAGAAGCTGCTGACCTGAAGGAAGGA |
| 3:Dog | ..........................A..A..A..A.C...CA..........CATT....T...CA.T...... |
| 4:Human | ....................C...A..A..T..A.C...........C.A..........TT....T...CAGT..T...... |
| 5:Mouse | ...AGTGA..GGA...............AG.T...A.C..C..ACC........T...CT...T...CA...C........G |

| | 80........90.......100.......110.......120.......130.......140.......150 |
|---|---|
| Protein | I N F L R N K K T G K D F I L Y K S K N R V R A C |
| Cat | ATCAATTTCTTGAGAAACAAGAAGACCGGCAAAGATTTCATTCTGTACAAGAGCAAGAATCGCGTGAGGGCGTGC |
| Dog | .......TC..........TC...C..T.......A..C.C.........AT.......A.C..C.......A... |
| Human | .......TC.C..T.......TC.C..T.....GC..T...........C.A.G.CT.........AT....GC..AC.........A... |
| Mouse | .......T..TC.......T...TC..T....CT...T..G......GA..T.A.......GAG...G.C.ATC.A..A... |

Amended

Fig. 3 (sheet 2)

| Protein | K N V C K H Q G G L F I K D I E D L D G R S V R C |
|---|---|
| | ....160.......170.......180.......190.......200.......210.......220..... |
| Cat | AAGAACGTGTGCAAGCATCAAGGAGGCCTGTTCATAAAGACATGAAGATTTAGACGGAAGGTCTGTCAGATGC |
| Dog | .....TA................................G.......T............ |
| Human | .....TA...............C.........T......G........C........------------ |
| Mouse | ......C.C..............C..G............G........T..........C..T..A... |

| Protein | T K H N W R L D V S T M K Y V N P P G S F C Q D E |
|---|---|
| | ....230.......240.......250.......260.......270.......280.......290.......300 |
| Cat | ACAAAGCACAACTGGAGGTTGGATGTGAGCACCATGAAAWACGTCAATCCCCCAGGCAGCTTCTGTCAAGACGAA |
| Dog | ......A...............A...A.......G..TA......C......A.......T... |
| Human | --------------------------------------------------------------- |
| Mouse | ......A........A...A..C.............TA.....C.T....G................G |

| Protein | L V V E M D E E N G L L L E L N P P N P W D S E |
|---|---|
| | ....310.......320.......330.......340.......350.......360.......370..... |
| Cat | CTAGTTGTTGAAATGGATGAAGAGAMAATGGACTTTTACTTCTAGAACTGAATCCTCCCAATCCCTGGGATTCAGAA |
| Dog | ..................................................T..C............... |
| Human | --......................A.C.............G...T...........T..C..T.....C.T.C.G |
| Mouse | ..C....A.............A.C............G....CC..GG..........C.......T..C....C..T..T |

Amended

Fig. 3 (sheet 3)

| | ..380.........390.........400.........410.........420.........430.........440.........450 |
|---|---|
| Protein | P R S P E H L A F G E V Q I T Y L T H A C M D L K |
| Cat | CCCAGATCTCCTGAACATTTGGCTTTTGGAGAAGTGCAGATCACGTACCTCACCCACGCCTGCATGGACCTCAAG |
| Dog | .......G.....G..........................................G.T........T........ |
| Human | ....................................G.G...............A..A...T....T.T........ |
| Mouse | ....................G...............G.A..A............A..A...T....T.......... |

| | .........460.........470.........480.........490.........500.........510.........520...... |
|---|---|
| Protein | L G D K R M V F D P W L T G P A F A R G W L L H |
| Cat | CTGGGAGACAAGAGGATGGTGTTTGACCCCTGGTTAACGGGTCCTGCGTTCGCCCGAGGCTGGCTGCTGCAC |
| Dog | ......................C................TA.......C..T....G..A................ |
| Human | T.A........A............T..........TC..........T.T...T.A....T....C..T........ |
| Mouse | T.......C.A........A............TT..C.......T..T....A.......T....A..T........ |

| | .........530.........540.........550.........560.........570.........580.........590.........600 |
|---|---|
| Protein | E P P S D W L E R L C Q A D L I Y I S H M H S D H |
| Cat | GAGCCTCCGTCTGATTGGCTGGAGAGGCTGTGCCAGGCAGACCTGATTTACATCAGTCACATGCACTCAGACCAC |
| Dog | .......C................................A...........T.........T......G.....T |
| Human | .......A...................................C.............TC................. |
| Mouse | .......A....C.....T....................A.A......C...T.....C.................. |

Amended

Fig. 3 (sheet 4)

| | | | | | | | |
|---|---|---|---|---|---|---|---|
| Protein | ......610...... | ......620...... | ......630...... | ......640...... | ......650...... | ......660...... | ......670...... |
| | L S Y | P T L | K E L | A G R | R R P D I | P I Y V | G N T E R |
| Cat | CTGAGTTACCCCACACTGAAGGAGCTGGCTGGGAGAAGACCGGATATTCCCATTTATGTTGGAAACACGGAAAGA |
| Dog | ..C...C.........G.........A...T...A.................A.......................... |
| Human | .....................AA....T.................A.............................A......G |
| Mouse | .....C.....T.C.....C....TT.CCA....C....A.C.................CG....A......G |

| | | | | | | | |
|---|---|---|---|---|---|---|---|
| | ..680...... | ......690...... | ......700...... | ......710...... | ......720...... | ......730...... | ......740......750 |
| Protein | P V F | W N L | N Q S | G V Q | L T N I | N I V P | F G I W Q |
| Cat | CCTGTATTTTGGAATCTGAATCAGAGGCGGTGTCCAGTTGACCAATATCAATAGTGCCATTCGGAATATGGCAG |
| Dog | ..................................................T...........G.................. |
| Human | ..................................................T.........G.C.................. |
| Mouse | .................G.............T.C...GG....A.T.C....CG.G..T....T...........A |

| | | | | | | | |
|---|---|---|---|---|---|---|---|
| | ......760...... | ......770...... | ......780...... | ......790...... | ......800...... | ......810...... | ......820...... |
| Protein | Q V D | K N L | R F M I L | M D G | V H P E | M D T | C I I V |
| Cat | CAGGTAGACAAAAATCTTCGATTCATGATCTTGATGGATGGCGTTCATCCTGAGATGGACACTTGCATTATTGTG |
| Dog | ......................................................A............................ |
| Human | ......G..........................................C.T.............................. |
| Mouse | .............G...G..G.........................C........................A....C... |

Amended

Fig. 3 (sheet 5)

| | | | | | | | | | | | | | | | | | | | | | | | |
|---|---|---|---|---|---|---|---|---|---|---|---|---|---|---|---|---|---|---|---|---|---|---|---|
| Protein | | | ..830...... | | | ..840...... | E Y G H K I L N T V D C T R P N G G R L P E K V | ..850...... | | | ..860...... | | | ..870...... | | | ..880...... | | | ..890...... | | | ..900 |
| Cat | GAGTATAAAGGTCATAAGATACTTAATACAGTGGACTGCACCAGACCCAATGGGGGAAGGTTGCCTGAGAAGGTT |
| Dog | ........................................................................ |
| Human | .....C..............A......C...T...A................C...........AT....... |
| Mouse | .....C..............A......C..C.....................C.T.........A........ |

| | | | | | | | | | | | | | | | | | | | | | | | |
|---|---|---|---|---|---|---|---|---|---|---|---|---|---|---|---|---|---|---|---|---|---|---|---|
| Protein | | | ..910...... | | | ..920...... | A L M M S D F A G G A S G F P M T F S G G K F T E | ..930...... | | | ..940...... | | | ..950...... | | | ..960...... | | | ..970 |
| Cat | GCTCTAATGATGAGTGATTTTGCTGGAGGAGCATCAGGCTTTCCAATGACTTTCAGTGGTGAAAATTTACCGAG |
| Dog | ..........................................................T............. |
| Human | ..........C..A.......T..................................G............... |
| Mouse | ..........C..A.......T..................................T............... |

| | | | | | | | | | | | | | | | | | | | | | | | |
|---|---|---|---|---|---|---|---|---|---|---|---|---|---|---|---|---|---|---|---|---|---|---|---|
| Protein | | | ..980...... | | | ..990...... | E W K A Q F I K A E R K K L L N Y K A R L V K D L | ..1000..... | | | ..1010..... | | | ..1020..... | | | ..1030..... | | | ..1040..... | ..1050 |
| Cat | GAATGGAAAGCCCARTTCATTAAAGCAGAAAGGAAGAAGCTTCTTGAACTACAAGGCCCGGCTGGTGAAGGACCTA |
| Dog | ........G.G...........GA.....A............................A.............. |
| Human | ........G.G...........A...A............C................T......A.....G... |
| Mouse | ........G..............G.T...A..A.GA....TC.....T.....A..T.A..........G... |

Amended

Fig. 3 (sheet 6)

| | | | | | | | |
|---|---|---|---|---|---|---|---|
| | ....1060......1070......1080......1090......1100......1110......1120..... | | | | | | |
| Protein | Q P R I Y C P F A G Y F V E S H P S D K Y I K E T | | | | | | |
| Cat | CAACCCGAATTTATTGCCCCTTTGCTGGGTATTTTGTGGAATCTCACCATCAGACAAGTATATTAAGGAAACA | | | | | | |
| Dog | ......T.....C.....T................................C..T................. | | | | | | |
| Human | .................T...............................................C..C.. | | | | | | |
| Mouse | ..G.........C..C..T..G........C.........G............T.....C............ | | | | | | |

| | ....1130......1140......1150......1160......1170......1180......1190......1200 |
|---|---|
| Protein | N I K N D P N E L N N L I K K N S D V T W T P R |
| Cat | AACATCAAAAATGACCCAAATGAACTCAATAATCTTATCAAGAAAAACTCTGATGTGGTAACGTGGACCCCACGG |
| Dog | .............................G..T..................A.....A...............A |
| Human | .................C.....................................A.......A...T..A |
| Mouse | ..C.......................C.G.....C............G...........C....G..A....A |

| | ....1210......1220......1230......1240......1250......1260......1270..... |
|---|---|
| Protein | P G A T L D L S R M L K D P T D S K G I I E P P E |
| Cat | CCTGGAGCCACTCTTGATCTGAGTCGGATGCTAAAGGACCCGACAGACAGCAAGGGCATCATAGARCCTCCAGAG |
| Dog | .............A........................A..T.....................G......A.T |
| Human | ..G........C...........G..AA..A.....G.....T.GA.........................G.. |
| Mouse | ..C..TGTC..C..C..TG.CA.........G..........A...............TG..G.G......... |

Amended

Fig. 3 (sheet 7)

| | .1280.....1290.....1300.....1310.....1320.....1330.....1340.....1350 |
|---|---|
| Protein | G T K I Y K D S W D F E P Y L N I L N A A V G D E |
| Cat | GGGACCAAGATCTACAAGGATTCCTGGGACTTTGAACCCTATTTGAACATCTTGAATGCTGCTGTAGGAGATGAG |
| Dog | .....A..A..T.................................G..A........AG.........A..A........A |
| Human | .....A..A..T.................T........T......GAA...................C..........A |
| Mouse | .....A......T........................................GC..G..CC..G.G.......T.........CA........A |

| | .....1360.....1370.....1380.....1390.....1400.....1410.....1420..... |
|---|---|
| Protein | I F L H S S W I K E Y F T W A G F K D Y N L V V R |
| Cat | ATATTTCTTCACTCATCATCCTGGATAAAAGAATACTTCACYTGGGCKGGATTTAAGGATTACAACCTGGTGGTCAGG |
| Dog | .................................................T........A...............T......... |
| Human | .................................................T.......T........A................ |
| Mouse | ..C..CTG...T...................T.........G............T.........A................ |

| | .1430.....1440.....1450.....1460.....1470.....1480.....1490.....1500 |
|---|---|
| Protein | M I E T D E D F S P F P G G Y D Y L V D F L D L S |
| Cat | ATGATTGAAACAGATGAGGACTTCAGCCCTTTTCCYGGAAGGATATGACTATTTGGTTGACTTTCTAGACTTATCC |
| Dog | .........A.................................................T...T......... |
| Human | .........G...............AT........................................T...T......... |
| Mouse | ...................................................G..C.....C.....G.............T......... |

Amended

Fig. 3 (sheet 8)

Amended

Fig. 3 (sheet 9)

| | .1730......1740......1750......1760......1770......1780......1790......1780 |
|---|---|
| Protein | C  G  * |
| Cat | TGTGGGTAG |
| Dog | ......... |
| Human | ....A.C..AAGTGGCCTGCGATTTTGCAATTCTCTACAGAAAGAA |
| Mouse | ....AT... |

Amended

Fig. 4 (sheet 1)

Cat genomic sequence of *CMAH* including the 5'UTR to exon 2

1: (SEQ·ID·NO:2)
2: (SEQ·ID·NO:62)
3: (SEQ·ID·NO:63)

```
         -540         -530         -520         -510         -500         -490
1: A     ACGGAGGTTCTGTGGGAAAGTTAACTCACGAAGTAGCTGGTAGAGATACACCGCGTG
2: B     ............A...........................................
3: AB    ............R...........................................

-480         -470         -460         -450         -440         -430
   A     ACAGGCCGTGTGCTCAGCGACACAGGGAGGAGAATGTTTGGAAAAGCGTCCCTATGTAAATA
   B     .......................G......................................
   AB    .......................R......................................

-420         -410         -400         -390         -380         -370
   A     AACGGGGCACCGTGCCGGGTGTAAGGTTCTCATGTTCTACAGAATGGTAGTGCGTATCAGC
   B     ..........................................................T.
   AB    ..........................................................Y.

-360         -350         -340         -330         -320         -310
   A     ACGTGTAGGCTTGTCCCGGGGGTGGCTTGACCCAGGCTGGGGTAGGAGGACT
   B     .G..................................................
   AB    ....................................................
```

Amended

Fig. 4 (sheet 2)

```
         -300        -290        -280        -270        -260        -250
A   GGGTTCTATTTGAACCTGGAGGGTGGTAAACATGACTAGTGGTGAAAGTTGAACCGTGCTT
B   ............................................................
AB  ............................................................

-240        -230        -220        -210        -200        -190
A   GTGAGCAAAAGGATCAGATCTAAACGCAGAAGTGTGCAGGTGGGAGCGGGCAGGGTGGGCA
B   ...................................A........................
AB  ...................................R........................

-180        -170        -160        -150        -140        -130
A   CCTGGAGCCCAATAGGATCCTGCGTCTGAAGCAACACAGCAGAGGAAGTGGTGCAACGGAA
B   ............................................................
AB  ............................................................

-120        -110        -100         -90         -80         -70
A   TCAGTAGTGAACCGGCGTCATATGCATCCTCCGTCTCATACTTTGTGGGAGCA------
B   ..................A.........................................AACGAGCA
AB  ..................R.........................................

-60         -50         -40         -30         -20         -10
A   ------AACGAGCAACCACCGTCCTTTCAGAATTCCCAGGGAGAGGCAGCTGCGGAC
B   ACCGAAGCTG..............................................
AB  ----------..............................................
```

Amended

Fig. 4 (sheet 3)

```
        10         20         30         40         50         60
  -1  ...:....|....:....|....:....|....:....|....:....|....:....|
A     CATGGGCaggcaagtgacaggggcattgggtctggaggaacccgagaccaacactgagcaa
B     ..............................................................
AB    ..............................................................

70         80         90        100        110        120
      ...:....|....:....|....:....|....:....|....:....|....:....|
A     gcagagcgtgcatttccaggggagcagccaagcctggtcctgcgaggagggcttgagc
B     ..............................................................
AB    ..............................................................

130        140        150        160        170        180
      ...:....|....:....|....:....|....:....|....:....|....:....|
A     ctatcgcggtggaaagaggctttgagccgccagtttcaaaagATGctctccctaagtcttaa
B     ......t.......................................................
AB    ......y.......................................................

190        200        210        220        230
      ...:....|....:....|....:....|....:....|....:....|
A     cgttattaacctttccctccccccaaaATGtctgcctttccgtAGCATTGAA
B     ..............................................................
AB    ..............................................................
```

Amended

Fig. 5 (sheet 1)

5' UTR mRNA sequence of feline CMAH

1: (SEQ·ID·NO:55)
2: (SEQ·ID·NO:64)
3: (SEQ·ID·NO:65)
4: (SEQ·ID·NO:66)
5: (SEQ·ID·NO:67)
6: (SEQ·ID·NO:68)

a.

```
        -121      -110       -100       -90        -80        -70
1: A    AGTAGTGAACCGCGTGCATATGCATCCTCCGTCTCATACTTTGTGGGAGCA-----------
2: Ab   ------------------------------------------------------------
3: Ab   ------------------------------------------------------------
4: B    ---------------------------------------------------AACGAGCAACCGAAGCTG
5: AB   ...................................................AACGAGCAACCGAAGCTG
6: AB   ------------------------------------------------------------

-50        -40        -30        -20        -10         -1123    12
1: A    AACGAGCAACCACCGTCCTTTCAGAATTCCCAGGGAGAGGCAGCTGCGACCATGGGCAGCATT
2: Ab   ..........................................................
3: Ab   .......G..................................................
4: B    ..........................................................
5: AB   .............................C............................
6: AB   ..........................................................
```

Amended

Fig. 5 (sheet 2)

1: (SEQ-ID-NO:56)
2: (SEQ-ID-NO:69)
3: (SEQ-ID-NO:70)
4: (SEQ-ID-NO:71)
5: (SEQ-ID-NO:72)

b.

```
1: Ab  cagtttcaaaagATGctctcctaagtcttaacgttatta
2: B   -----------------.....................
3: AB  -----------------.....................
4: AB  -----------------.....................
5: AB  -----------------.....................

Ab  accttcctccccccaaATGtctgcctttccgtAGCATT
   B   ......................................
   AB  ......................................
   AB  ......................................
   AB  g.....................................
```

Amended

TEST FOR DETERMINING BLOOD TYPE IN THE CAT

CROSS-REFERENCES TO RELATED APPLICATIONS

The present application claims priority to U.S. Ser. No. 60/876,721, filed Dec. 21, 2006.

STATEMENT AS TO RIGHTS TO INVENTIONS MADE UNDER FEDERALLY SPONSORED RESEARCH AND DEVELOPMENT

Funding for this research was provided by NIH-NCRR RR016094. This invention was made with government support under NIH-NCRR RR016094 awarded by National Institutes of Health. The government has certain rights in the invention.

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Only one major blood group system has been identified for the domestic cat, whereas a plethora of systems are recognized in dogs, humans, horses and other species. (Bell, K. *Red blood cells of domestic mammals*, 133-164 (1983)) The major blood group system of domestic cats was identified in the early 1900's. (Ingebrigsten, *R. J Exper Med.*, 16:169-177 (1912); Ottenburg, R. et al., *J Med Res.*, 28:213-229 (1915)) This blood group was later found to contain two types based on red cell reactions with naturally occurring alloantibodies. (Eyquem, A. et al., *Ann N Y Acad Sci.*, 97:320-328 (1962); Holmes, R. *J Physiol.*, 111:61 (1950)) The two major blood types are called type A and type B. (Auer, L. et al., *Anim Blood Groups Biochem Genet.*, 12:287-297 (1981)) The common types are allelic, with type A dominant to type B. A rare type AB has not been as clearly defined, but is suspected to be allelic to types A and B. (Auer, L. et al., *Anim Blood Groups Biochem Genet.*, 12:287-297 (1981); Griot-Wenk, M. et al., *Anim Genet.*, 24:401-407 (1993)) Several studies have shown familial segregation for type A and type B. However, families segregating for type AB are limited and the parentage of the matings was not confirmed, thus, inheritance of the third type AB allele is not clearly resolved (Auer, L. et al., *Anim Blood Groups Biochem Genet.*, 12:287-297 (1981); Griot-Wenk, M. et al., *Anim Genet.*, 24:401-407 (1993)), though it appears to be recessive to type A but dominant to type B. (Griot-Wenk, M. E. et al., *Am J Vet Res.*, 57:1438-1442 (1996)) A majority of random bred cats throughout the world are type A. (Eyquem, A. et al., *Ann N Y Acad Sci.*, 97:320-328 (1962); Holmes, R., *J Physiol.*, 111:61 (1950); Auer, L. et al., *Anim Blood Groups Biochem Genet.*, 12:287-297 (1981); Bagdi, N. et al., *Acta Vet Hung.*, 49:369-375 (2001); Giger, U. et al., *J Am Vet Med Assoc.*, 195:1230-1232 (1989); Hubler, M. et al., *Schweiz Arch Tierheilkd.*, 135:231-235 (1993); Knottenbelt, C. M. et al., *J Small Anim Pract.*, 40:115-118 (1990); Malik, R. et al., *Aust Vet J*, 83:38-44 (2005)) However, some pure breeds have a high frequency of type B individuals (FIG. 1). The Siamese, Tonkinese and Burmese breeds are nearly fixed for type A, whereas the prevalence of type B individuals of British Shorthairs, Birmans, Devon and Cornish Rex can range between 25-50%. (Giger, U. et al., *J Hered.*, 82:15-20 (1991)) Although type B cats are rare in random bred populations, admixtures with cat breeds are increasing the frequency of type B cats in the random bred population. For example, type B cats are more common in the random bred populations of California (Giger, U. et al., *Feline Practice*, 19:21-27 (1991)) and Australia than in Europe and the rest of the United States. (Malik, R. et al., *Aust Vet J.*, 83:38-44 (2005)) Thus, veterinary clinics and hospitals are finding it increasingly necessary to maintain both type A and type B cats for blood transfusions.

Feline blood types are especially important because of the phenomena of neonatal isoerythrolysis (Cain, G. R. et al., *J Am Vet Med. Assoc.*, 187:46-48 (1985); Giger, U. et al., *J Reprod Fertil Suppl.*, 51:313-316 (1997); Hubler, M. et al., *Journal of Small Animal Practice*, 28 (1987)) and transfusion reactions (Auer, I. et al., In: Kirk R W, ed. "Current Veterinary Therapy IX," Philadelphia: WB Saunders Co; 515-521 (1986); Auer, L. et al., *Res Vet Sci.*, 35:145-152 (1983); Auer, L. et al., *J Am Vet Med Assoc.*, 180:729-730 (1982); Giger, U., et al., *Probl Vet Med.*, 4:600-611 (1992)) between previously non-sensitized donors. Similar to the unrelated ABO system of humans, cats often possess alloantibodies for their opposite blood type. Blood type B cats possess strong agglutinins and hemolysins to type A red cells. Type A cats possess alloantibodies that are weak agglutinins but strong hemolysins for type B red cells. Thus, a blood transfusion of a type B cat with type A blood can cause a severe reaction. Milder reactions occur if type B blood is transfused into a type A cat. Interestingly, blood type AB cats are universal recipients since they lack alloantibodies against either blood type. The presence of strong, naturally occurring alloantibodies in the type B cat against the A antigens also leads to neonatal isoerythrolysis for type A kittens born from a type B queen. The prevention of transfusion reactions and neonatal isoerythrolysis requires close monitoring of blood types of donor and recipient, and toms and queens. (Giger, U. et al., *J Reprod Fertil Suppl.*, 51:313-316 (1997); Jonsson, N. N. et al., *Aust Vet J.*, 67:416-417 (1990); Bucheler, J., *Vet Clin North Am Small Anim Pract.*, 29:853-870 (1999); Bridle, K. H. et al., *J Small Anim Pract.* 39:88-89 (1998); Casal, M. L. et al., *Am J Vet Res.*, 57:1653-1658 (1996)).

For these and other reasons, new and improved methods of blood typing cats are needed. The present invention satisfies these and other needs.

BRIEF SUMMARY OF THE INVENTION

One embodiment of the present invention provides isolated polynucleotides comprising the sequence in SEQ ID NO:1 or a complement thereof. In an aspect of this embodiment, an expression vector comprising a polynucleotide of SEQ ID NO:1, operably linked to an expression control sequence, and host cells comprising the expression vector are provided. In another embodiment, an isolated polypeptide comprising an amino acid sequence encoded by a polynucleotide of SEQ ID NO:1 is provided.

A further embodiment of this invention provides a method of determining blood type in the cat, comprising the steps of obtaining a biological sample and detecting the presence or absence of a mutation in both alleles of the feline CMAH gene, where a mutation in both alleles is indicative of blood type B, thereby distinguishing blood type B from blood types A and AB. In an aspect of this embodiment, the mutation is selected from the group consisting of: inclusion of an 18 base pair insertion at position −53 in the 5' UTR of exon 1, a G to A substitution at position −217 in the 5' UTR of exon 1, a C to T substitution at position −371 in the 5' UTR of exon 1, a G to A substitution at position 139 of exon 2, a G to A substitution at position 139 of exon 2, a T to A substitution at position 265 of exon 3, a T to A substitution at position 265 of exon 3, and a G to A substitution at position 1600 of exon 13. A further aspect of this embodiment provides for the detection of the mutation comprising the steps of (a) specifically amplifying a subsequence of the gene encoding CMAH containing the mutation, thereby amplifying nucleic acids comprising the mutation, and (b) detecting the amplified nucleic acids. In various aspects of this embodiment, the subsequence comprises: position −53 in the 5' UTR in exon 1, position −217 in the 5' UTR in exon 1, position −371 in the 5' UTR in exon 1, position 139 in exon 2, position 265 in exon 3, or position 1600 in exon 13. In various aspects, the relevant subsequence can be specifically amplified using pairs of primers comprising the sequences set forth in SEQ ID NO: 4 and 5; SEQ ID NO: 6 and 7; SEQ ID NO: 8 and 9; or SEQ ID NO: 24 and 25. In some aspects of this embodiment, the amplified nucleic acids are detected by sequencing.

In another embodiment of this invention, the invention provides a method of determining blood type in the cat, comprising the steps of obtaining a biological sample and detecting a haplotype of the feline CMAH gene, where presence of the haplotype in homozygous form is indicative of blood type B, thereby distinguishing blood type B from blood types A and AB. In an aspect of this embodiment, the haplotype comprises: an 18 base pair insertion at position −53 in the 5' UTR of exon 1, a G to A substitution at position −217 in the 5' UTR of exon 1, a C to T substitution at position −371 in the 5' UTR of exon 1, a G to A substitution at position 139 of exon 2, a G to A substitution at position 139 of exon 2, a T to A substitution at position 265 of exon 3, a T to A substitution at position 265 of exon 3, and a G to A substitution at position 1600 of exon 13.

In a further embodiment of this invention, a method of identifying a blood type B carrier in the cat is provided, comprising the steps of obtaining a biological sample and detecting the presence or absence of a mutation of the feline CMAH gene, where presence of the mutation is indicative of blood type B, thereby identifying a blood type B carrier in the cat. In an aspect of this embodiment, the mutation can include: inclusion of an 18 base pair insertion at position −53 in the 5' UTR of exon 1, a G to A substitution at position −217 in the 5' UTR of exon 1, a C to T substitution at position −371 in the 5' UTR of exon 1, a G to A substitution at position 139 of exon 2, a G to A substitution at position 139 of exon 2, a T to A substitution at position 265 of exon 3, a T to A substitution at position 265 of exon 3, or a G to A substitution at position 1600 of exon 13.

In yet a further embodiment, the present invention provides a method of identifying a blood type B carrier in the cat, comprising the steps of obtaining a biological sample and detecting a haplotype of the feline CMAH gene, where presence of the haplotype is indicative of blood type B, thereby identifying a blood type B carrier in the cat. In an aspect of this embodiment, the haplotype can comprise: an 18 base pair insertion at position −53 in the 5' UTR of exon 1, a G to A substitution at position −217 in the 5' UTR of exon 1, a C to T substitution at position −371 in the 5' UTR of exon 1, a G to A substitution at position 139 of exon 2, a G to A substitution at position 139 of exon 2, a T to A substitution at position 265 of exon 3, a T to A substitution at position 265 of exon 3, or a G to A substitution at position 1600 of exon 13.

BRIEF DESCRIPTION OF THE DRAWINGS

FIG. 3. Sequence and protein translation of feline CMAH. The composite feline sequence of CMAH (SEQ ID NO:1) is presented with its protein translation (SEQ ID NO:3) listed above the cDNA sequence. Identified DNA variants are presented in bold and underlined. Mutations that cause an amino acid change are presented with an underlined codon, the mutation and protein code in bold. The cDNA sequence of the dog (SEQ ID NO:86), human (SEQ ID NO:87) and mouse (SEQ ID NO:88) are presented below the cat. Missing sequence is presented as a dash. The 2 codons of exon 1 have not yet been identified in the dog, 2 additional codons are absent downstream. Approximately 31 amino acids are deleted in humans, causing inactivation of the enzyme.

FIG. 4. Cat genomic sequence of CMAH including the 5'UTR to exon 2. A 781 bp sequence generated from genomic DNA from cats of each blood type (SEQ ID NOS:2, 89 and 90). Lower case letters represent introns 1. The six bold upper case letters are the last six nucleotides of exon 1 that are translated to the methionine start and a glycine prior to the splice with exon 2. AGT sites are underlined. The lower case in italics is the intronic 1 sequence that is the splice variant sequence found in the cDNA of type B cats, spliced immediately upstream of the exon 2 sequence. Two GATA transcription factor sites are underlined. The mutations that are consistent with blood group phenotypes, a-217g and the t-371c, are presented in bold and underlined. One introns 1 variant and three 5' UTR mutations that are not consistent with blood types are also presented.

FIG. 5. 5' UTR mRNA sequence of feline CMAH. A. Presented are the 5' UTR regions of the CMAH cDNA (SEQ ID NOS:58 and 91-95) sequences identified from cats of each blood type. The cat blood type is presented on the left. The number of clones with the same sequence is represented in parentheses. The last six nucleotides show the AGT start and the last codon of exon 1, presenting a strong kozak sequence for translation initiation. The upstream sequence is untranslated, in accordance with CMAH alignments and cDNA studies from other species. However, an additional ATG occurs at −102 bp, which is in frame for the putative type A allele. The 18 bp insertion is a concordant with type B cats. This insertion disrupts the reading frame if the −102 bp ATG is active. B. Additional cDNA (SEQ ID NOS:59 and 96-98) species were identified that are apparent splicing errors, which splice introns 1 sequence, presented in lower case nucleotides, to the beginning of exon 2. No alternatively spliced sequences were identified in the type A cat, which is assumed to be homozygous and has a homozygous type A genotype for the other diagnostic SNPs.

DETAILED DESCRIPTION OF THE INVENTION

I. Introduction

Figure 1:
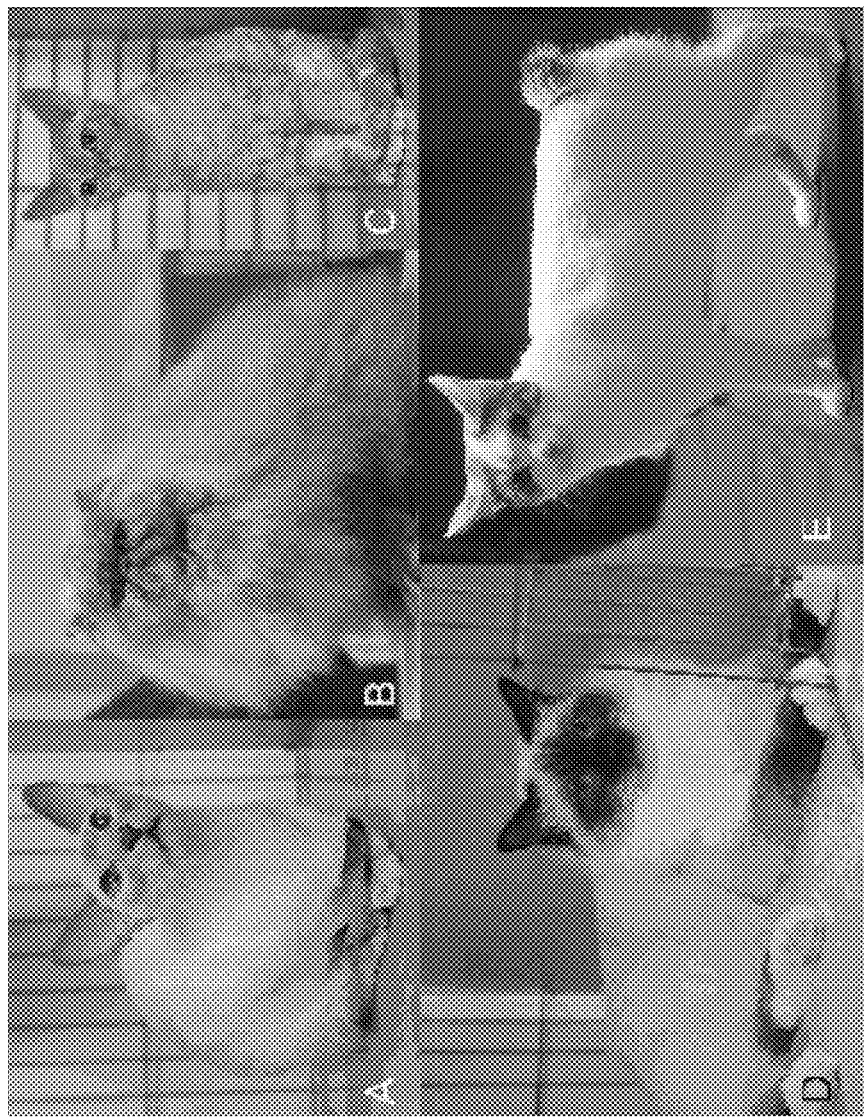
FIG. 1. Cats breeds with different frequencies of the type A and type B blood groups. a. Siamese are fixed for type A. b. Persian, c. Devon Rex, d. Birman and e. Japanese Bobtail all segregate for type B and management of neonatal isoerythrolysis is pertinent to the breeds.

The A and B blood types of cats are caused by differences in the neuraminic acid residues present on a ceramide dihexose backbone on the surface of erythrocytes. (Ando, N. et al., *J Biochem (Tokyo)*, 91:873-881 (1982); Andrews, G. A. et al., *Blood.*, 79:2485-2491 (1992); Furukawa, K. et al., *J Biol Chem.*, 263:14939-14947 (1988); Hamanaka, S. et al., *J Biochem (Tokyo)*, 86:695-698 (1979)) The type A cat has mainly N-glycolylneuraminic acid (NeuGc) and a small amount of N-acetylneuraminic acid (NeuAc), while the type B cat has only NeuAc. (Andrews, G. A. et al., *Blood.*, 79:2485-2491 (1992)) Since type A is dominant to type B, obligate carriers of type B (type Ab) present similarly to the type A cat. Rare type AB cats have both NeuAc and NeuGc presented on the red cells in similar quantities, each at approximately 50% normal expression levels. (Griot-Wenk, M. et al., *Anim Genet.*, 24:401-407 (1993))

NeuAc is converted to NeuGc in a pathway that catalyzed by cytidine monophospho-N-acetylneuraminic acid hydroxylase (CMAH). (Muchmore, E. A. et al., *J Biol Chem.*, 264:20216-20223 (1989)) N-glycolylneuraminic acid (NeuGc) is expressed in most mammals but not in humans. (Irie, A. et al., *J Biol Chem.*, 273:15866-15871 (1998)) Human CMAH was inactivated after their divergence from chimpanzees by a deletion in the coding region. (Irie, A. et al., *J Biol Chem.*, 273:15866-15871 (1998)) However, CMAH has remained active in cats, but only in cats with type A red cells. CMAH is postulated to be either absent or nonfunctional in type B cats, because recessive type B cats do not convert NeuAc to NeuGc. (Andrews, G. A. et al., *Blood.*, 79:2485-2491 (1992)) In this study, feline CMAH was characterized and examined for mutations that could influence, and characterize, the cat AB blood group system.

The cat has one common blood group with two allelic types, blood type A that is dominant to type B. A rare type AB may also be allelic. Cat blood type Antigens are defined, N-glycolylneuraminic acid (NeuGc) is associated with type A and N-acetylneuraminic acid (NeuAc) with type B. The enzyme cytidine monophospho-N-acetylneuraminic acid hydroxylase (CMAH) converts NeuAc to NeuGc, determining the sugar bound to the red cell. Thus, mutations in CMAH may cause the A and B blood types. Genomic sequence of CMAH from eight cats and the cDNA of four cats representing all blood types were analyzed to identify causative mutations. DNA variants consistent with the blood types were genotyped in over 200 cats. Five SNPs and an indel formed haplotypes that were consistent with each blood type. Mutations in type B cats likely disrupt the gene function of CMAH, leading to a predominance of NeuAc. Type AB concordant variants were not identified, however, cDNA species suggest an alternative allele that activates a downstream start site, leading to a CMAH protein that would be altered at the 5' region. The identified mutations can be used to distinguish type A and Type B cats without blood sample collection.

The present invention is based on the identification of mutations in the feline CMAH gene that are associated with the determination of blood type in the cat. Each of the exons of the CMAH gene from cats of different blood types was scanned for mutations. The result of this investigation was the identification of 6 mutations in the CMAH gene which are indicative of the B blood type in cats. Thus, the present invention can be used to distinguish cats with blood type B from those with blood types A and AB. Furthermore, the present invention can be used to identify carriers of the B blood type.

II. Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y.), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

The terms "CMAH," and "CMAH" refer to nucleic acids and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to an amino acid sequence encoded by a CMAH nucleic acid (for a cat CMAH nucleic acid sequence, see, e.g., SEQ ID NOS: 1, 2, or 3 and FIG. 1; for an amino acid sequence of a cat CMAH polypeptide see, e.g., FIG. 1); (2) bind to antibodies, e.g., polyclonal antibodies, raised against an immunogen comprising an amino acid sequence of a CMAH polypeptide (e.g., encoded by SEQ ID NOS: 1, 2, or 3), and conservatively modified variants thereof; (3) specifically hybridize under stringent hybridization conditions to an anti-sense strand corresponding to a nucleic acid sequence encoding a CMAH protein, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a CMAH nucleic acid. A polynucleotide or polypeptide sequence is typically from a mammal including, but not limited to, domestic cats and wild cats (e.g., of the family Felidae; the subfamilies, Felinae, Pantherinae, and Acinonychinae; the genera *Caracal, Catopuma, Felis, Herpailurus, Leopardus, Leptailurus, Lynx, Oncifelis, Oreailurus, Otocolobus, Prionailurus, Profelis, Puma, Neofelis, Panthera, Pardofelis,* and *Uncia*; and the species *felis, lybica, jubatus, caracal, badia, bieti, chaus, margarita, nigripes, silvestris, gordonii, yaguarondi, pardalis, tigrinus, wiedi, serval, canadensis, lynx, pardinus, rufus, colocolo, geoffroyi, guigna, jacobita, manul, bengalensis, planiceps, rubiginosus, viverrinus, aurata, concolor, nebulosa, leo, onca, pardus, tigris, marmorata,* and *uncia*. The nucleic acids and proteins of the invention include both naturally occurring or recombinant molecules.

The term "haplotype" refers generally to a set of closely linked genetic markers present on one chromosome which tend to be inherited together (i.e., are not easily separable by recombination). A haplotype can be characterized by a series of single nucleotide polymorphisms (SNPs) that are present on one chromosome and which are inherited together.

The term "allele" has the meaning conventionally associated with this term in genetics and generally refers to any of a number of alternative forms of a gene or segment of the chromosome.

The terms "homozygous" and "heterozygous" have the meanings conventionally associated with these terms in genetics and generally refer to the state of having two identical or non-identical, respectively, alleles of a particular gene or segment of the chromosome.

The term "blood type" refers generally to one of many groups into which an individual's blood can be categorized, based on the presence or absence of specific antigens on the surface of blood cells. In the cat, three blood types have been recognized, termed A, B, and AB.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated CMAH nucleic acid is separated from open reading frames that flank the CMAH gene and encode proteins other than CMAH. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or "detectable label" is a composition detectable by spectroscopic, photochemical, biochemical, immunochemical, or chemical means. For example, useful labels include radioisotopes (e.g., $^3$H, $^{35}$S, $^{32}$P, $^{51}$Cr, or $^{125}$I), fluorescent dyes, electron-dense reagents, enzymes (e.g., alkaline phosphatase, horseradish peroxidase, or others commonly used in an ELISA), biotin, digoxigenin, or haptens and proteins for which antisera or monoclonal antibodies are available (e.g., the polypeptide encoded by SEQ ID NOS: 1, 2, or 3 can be made detectable, e.g., by incorporating a radiolabel into the peptide, and used to detect antibodies specifically reactive with the peptide).

An "amplification reaction" refers to any chemical reaction, including an enzymatic reaction, which results in increased copies of a template nucleic acid sequence. Amplification reactions include polymerase chain reaction (PCR) and ligase chain reaction (LCR) (see U.S. Pat. Nos. 4,683,195 and 4,683,202; PCR Protocols: A Guide to Methods and Applications (Innis et al., eds, 1990)), strand displacement amplification (SDA) (Walker, et al. Nucleic Acids Res. 20(7): 1691 (1992); Walker PCR Methods Appl 3(1):1 (1993)), transcription-mediated amplification (Phyffer, et al., J. Clin. Microbiol. 34:834 (1996); Vuorinen, et al., J. Clin. Microbiol. 33:1856 (1995)), nucleic acid sequence-based amplification (NASBA) (Compton, Nature 350(6313):91 (1991), rolling circle amplification (RCA) (Lisby, Mol. Biotechnol. 12(1):75 (1999)); Hatch et al., Genet. Anal. 15(2):35 (1999)) and branched DNA signal amplification (bDNA) (see, e.g., Iqbal et al., Mol. Cell Probes 13(4):315 (1999)).

"Amplifying" refers to submitting a solution to conditions sufficient to allow for amplification of a polynucleotide if all of the components of the reaction are intact. Components of an amplification reaction include, e.g., primers, a polynucleotide template, polymerase, nucleotides, and the like. Thus, an amplifying step can occur without producing a product if, for example, primers are degraded.

"Amplification reagents" refer to reagents used in an amplification reaction. These reagents can include, e.g., oligonucleotide primers; borate, phosphate, carbonate, barbital, Tris, etc. based buffers (see, U.S. Pat. No. 5,508,178); salts such as potassium or sodium chloride; magnesium; deoxynucleotide triphosphates (dNTPs); a nucleic acid polymerase such as Taq DNA polymerase; as well as DMSO; and stabilizing agents such as gelatin, bovine serum albumin, and non-ionic detergents (e.g. Tween-20).

The term "primer" refers to a nucleic acid sequence that primes the synthesis of a polynucleotide in an amplification reaction. Typically a primer comprises fewer than about 100 nucleotides and preferably comprises fewer than about 30 nucleotides. Exemplary primers range from about 5 to about 25 nucleotides. The "integrity" of a primer refers to the ability of the primer to primer an amplification reaction. For example, the integrity of a primer is typically no longer intact after degradation of the primer sequences such as by endonuclease cleavage.

The term "subsequence" refers to a sequence of nucleotides that are contiguous within a second sequence but does not include all of the nucleotides of the second sequence.

A "target" or "target sequence" refers to a single or double stranded polynucleotide sequence sought to be amplified in an amplification reaction. Two target sequences are different if they comprise non-identical polynucleotide sequences.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The terms "promoter" and "expression control sequence" are used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region such as exons 1 or 2 of the CMAH gene or another region of SEQ ID NOS: 1, 2, or 3), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to CMAH nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH—CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of monoclonal or polyclonal antibodies, any technique known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., Nature 348: 552-554 (1990); Marks et al., Biotechnology 10:779-783 (1992)).

An "immunogenic fragment" is one that elicits or modulates an immune response, preferably the composition induces or enhances an immune response in response to a particular CMAH or a portion thereof. Immune responses include humoral immune responses and cell-mediated immune responses, such as antibody production.

Figure 2B:
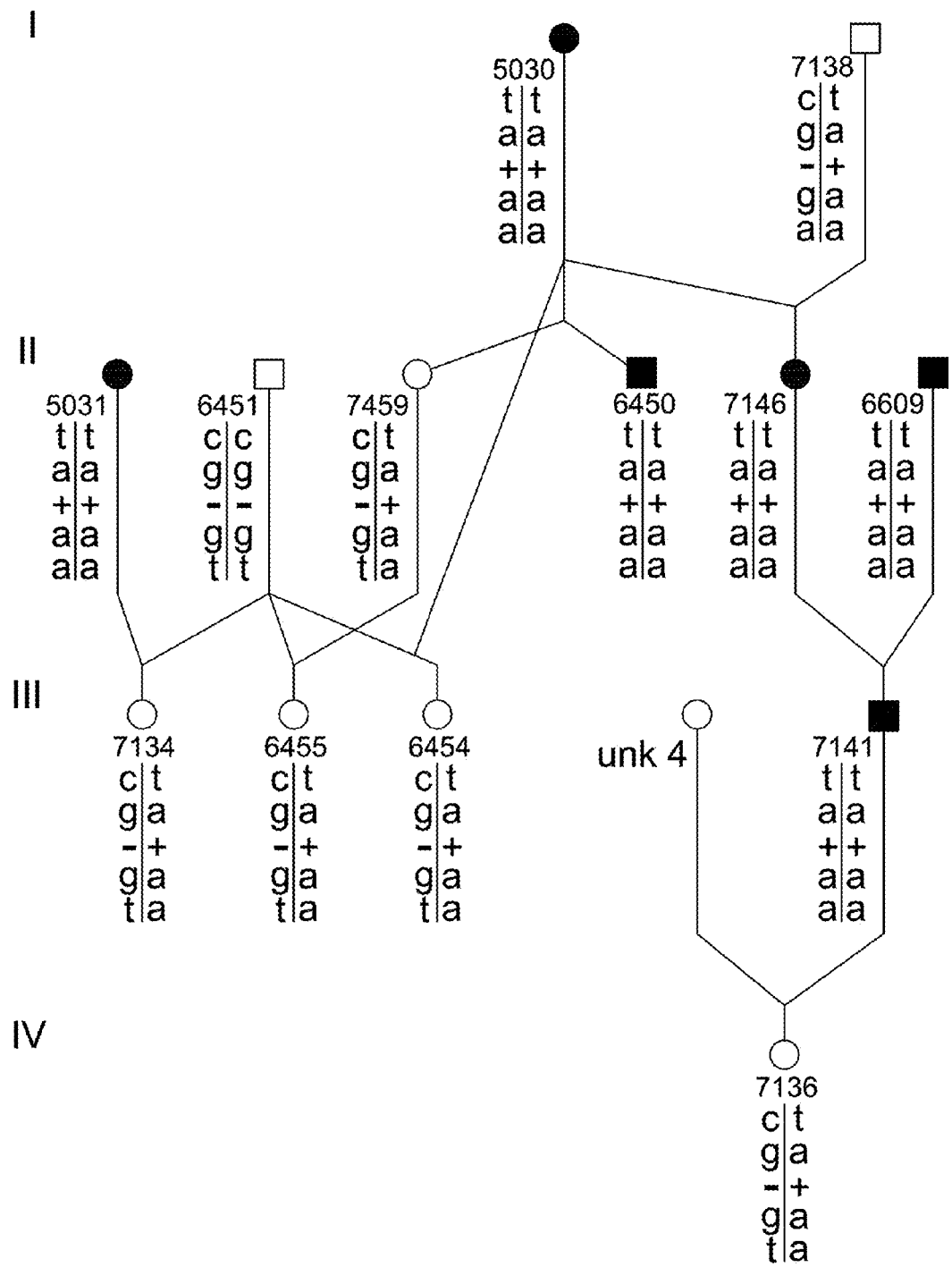
FIG. 2. Families of cats segregating for blood types and CMAH variants. a. British Shorthair, b. Birman. Circles represent females, squares represent males, filled symbols indicate type B cats from hemoagglutination assays. Symbols with a diagonal slash represent cats that were not available for the analyses. Numbers under the symbols represent the laboratory sample number. Genotypes for the CMAH variants are represented below the cat identification numbers, respectively, and are presented as haplotypes in the order; G-217A, T-371C, -53, G139A, T265A.

An "anti-CMAH" antibody is an antibody or antibody fragment that specifically binds a polypeptide encoded by a CMAH gene, cDNA, or a subsequence thereof including polypeptides encoded by a mutant CMAH gene, cDNA, or a subsequence thereof, e.g., the sequences set forth in FIG. 2 or subsequences thereof.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that uses an antibody to specifically bind an antigen. The immunoassay is characterized by the use of specific binding properties of a particular antibody to isolate, target, detect, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to CMAH can be selected to obtain only those polyclonal antibodies that are specifically immunoreactive with mutants of CMAH (e.g., a mutant comprising a sequence encoded by SEQ ID NOS: 1, 2, or 3) and not with other proteins (e.g., wild type CMAH). This selection may be achieved by subtracting out antibodies that cross-react with molecules such as CMAH from other species. In addition, polyclonal antibodies raised to CMAH polymorphic variants, alleles, orthologs, and conservatively modified variants can be selected to obtain only those antibodies that recognize specific fragments of CMAH. For example polyclonal antibodies raised to can be selected to obtain only those antibodies that recognize polypeptides encoded by exons 1 or 2 of CMAH, but not other CMAH fragments. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

"Biological sample" as used herein is a sample of biological tissue or fluid that is suspected of containing a nucleic acid encoding a mutant CMAH polypeptide or a mutant CMAH polypeptide. These samples can be tested by the methods described herein and include body fluids such as whole blood, serum, plasma, cerebrospinal fluid, urine, lymph fluids, and various external secretions of the respiratory, intestinal and genitourinary tracts, tears, saliva, milk, white blood cells, myelomas, and the like; and biological fluids such as cell extracts, cell culture supernatants; fixed tissue specimens; and fixed cell specimens. Biological samples may also include sections of tissues such as biopsy and autopsy samples or frozen sections taken for histologic purposes. These samples are well known in the art. A biological sample is obtained from any mammal including, e.g., a cat. A biological sample may be suspended or dissolved in liquid materials such as buffers, extractants, solvents and the like.

III. Nucleic Acids Encoding Mutant Wild Type and Mutant CMAH

A. General Recombinant DNA Methods

This invention relies on routine techniques in the field of recombinant genetics. Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, Tetrahedron Letts. 22:1859-1862 (1981), using an automated synthesizer, as described in Van Devanter et. al., Nucleic Acids Res. 12:6159-6168 (1984). Purification of oligonucleotides is by either native acrylamide gel electrophoresis or by anion-exchange HPLC as described in Pearson & Reanier, J. Chrom. 255:137-149 (1983).

The sequence of the cloned genes and synthetic oligonucleotides can be verified after cloning using, e.g., the chain termination method for sequencing double-stranded templates of Wallace et al., Gene 16:21-26 (1981).

B. Cloning Methods for the Isolation of Nucleotide Sequences Encoding Mutants of CMAH In general, the nucleic acid sequences encoding CMAH and related nucleic acid sequence homologues are cloned from cDNA and genomic DNA libraries or isolated using amplification techniques with oligonucleotide primers. For example, CMAH sequences are typically isolated from nucleic acid (genomic or cDNA) libraries by hybridizing with a nucleic acid probe, the sequence of which can be derived from SEQ ID NO: 1 or 2 or a subsequence thereof. CMAH RNA and cDNA can be isolated from any cat.

Nucleic acids encoding CMAH can also be isolated from expression libraries using antibodies as probes. Such polyclonal or monoclonal antibodies can be raised using, for example, the polypeptides encoded by the sequence of SEQ ID NO: 1 or fragments thereof.

CMAH polymorphic variants, alleles, and interspecies homologues that are substantially identical to CMAH can be isolated using CMAH nucleic acid probes and oligonucleotides under stringent hybridization conditions, by screening libraries. Alternatively, expression libraries can be used to clone CMAH polymorphic variants, alleles, and interspecies homologues, by detecting expressed homologues immunologically with antisera or purified antibodies made against the core domain of CMAH which also recognize and selectively bind to the CMAH homologue.

To make a cDNA library, CMAH mRNA may be purified from any cat. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, Gene 25:263-269 (1983); Sambrook et al., supra; Ausubel et al., supra).

For a genomic library, the DNA is extracted from the tissue and either mechanically sheared or enzymatically digested to yield fragments of about 1-8 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, Science 196:180-182 (1977). Colony hybridization is carried out as generally described in Grunstein et al., Proc. Natl. Acad. Sci. USA., 72:3961-3965 (1975).

An alternative method of isolating CMAH nucleic acids and their homologues combines the use of synthetic oligonucleotide primers and amplification of an RNA or DNA template (see U.S. Pat. Nos. 4,683,195 and 4,683,202; PCR Protocols: A Guide to Methods and Applications (Innis et al., eds, 1990)). Methods such as polymerase chain reaction (PCR) and ligase chain reaction (LCR) can be used to amplify nucleic acid sequences of CMAH directly from mRNA, from cDNA, from genomic libraries or cDNA libraries. Degenerate oligonucleotides can be designed to amplify CMAH homologues using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of CMAH encoding mRNA in physiological samples, for nucleic acid sequencing, or for other purposes. Genes amplified by the PCR reaction can be purified from agarose gels and cloned into an appropriate vector.

Amplification techniques using primers can also be used to amplify and isolate CMAH DNA or RNA. For example, nucleic acids encoding CMAH or fragments thereof may be obtained by amplification of a cat cDNA library or reverse transcribed from cat RNA using isolated nucleic acid primer pairs having the following sequences: 5' primer: CAACACTGAGCAAGCAGAGC (SEQ ID NO:6) and 3' primer GGTTTCCTCTCTCTCAGGGG (SEQ ID NO:60) (exon 2); 5' primer CTCTTAGGACATGGACTGAACG (SEQ ID NO:8) and 3' primer CTTTGGTAAGACGGGTGAGAG (SEQ ID NO:61) (exon 3), among others, such as those shown in Table 1.

These primers can be used, e.g., to amplify either the full length sequence or a probe of one to several hundred nucleotides, which is then used to screen a cDNA library for full-length CMAH.

Gene expression of CMAH can also be analyzed by techniques known in the art, e.g., reverse transcription and amplification of mRNA, isolation of total RNA or poly A+ RNA, northern blotting, dot blotting, in situ hybridization, RNase protection, probing DNA microchip arrays, and the like.

Synthetic oligonucleotides can be used to construct recombinant CMAH genes for use as probes or for expression of protein. This method is performed using a series of overlapping oligonucleotides usually 40-120 bp in length, representing both the sense and non-sense strands of the gene. These DNA fragments are then annealed, ligated and cloned. Alternatively, amplification techniques can be used with precise primers to amplify a specific subsequence of the CMAH gene. The specific subsequence is then ligated into an expression vector. CMAH chimeras can be made, which combine, e.g., a portion of CMAH with a portion of a heterologous CMAH to create a chimeric, functional CMAH.

The gene for CMAH is typically cloned into intermediate vectors before transformation into prokaryotic or eukaryotic cells for replication and/or expression. These intermediate vectors are typically prokaryote vectors, e.g., plasmids, or shuttle vectors. Isolated nucleic acids encoding CMAH proteins comprise a nucleic acid sequence encoding a CMAH protein and subsequences, interspecies homologues, alleles and polymorphic variants thereof. In preferred embodiments, the isolated nucleic acid encoding a CMAH protein is SEQ ID NOS: 1, 2, or 3 or a complement thereof.

C. Expression of CMAH in Prokaryotes and Eukaryotes

To obtain high level expression of a cloned gene, such as those cDNAs encoding CMAH, one typically subclones CMAH into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the CMAH protein are available in, e.g., *E. coli, Bacillus* sp., and *Salmonella* (Palva et al., Gene 22:229-235 (1983); Mosbach et al., Nature 302:543-545 (1983). Kits for such expression systems are commercially available. Eukaryotic expression systems for mammalian cells, yeast, and insect cells are well known in the art and are also commercially available.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the CMAH encoding nucleic acid in host cells. A typical expression cassette thus contains a promoter operably linked to the nucleic acid sequence encoding CMAH and signals required for efficient polyadenylation of the transcript, ribosome binding sites, and translation termination. The nucleic acid sequence encoding CMAH may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a CMAH encoding sequence under the direction of the polyhedrin promoter or other strong baculovirus promoters.

The elements that are typically included in expression vectors also include a replicon that functions in $E.$ $coli$, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of CMAH protein, which are then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing CMAH.

After the expression vector is introduced into the cells, the transfected cells are cultured under conditions favoring expression of CMAH, which is recovered from the culture using standard techniques identified below.

D. Purification of CMAH Protein

Either naturally occurring or recombinant CMAH can be purified for use in functional assays. Naturally occurring CMAH are purified, e.g., from cat and any other source of a CMAH homologue. Recombinant CMAH is purified from any suitable expression system.

CMAH may be purified to substantial purity by standard techniques, including selective precipitation with such substances as ammonium sulfate; column chromatography, immunopurification methods, and others (see, e.g., Scopes, Protein Purification: Principles and Practice (1982); U.S. Pat. No. 4,673,641; Ausubel et al., supra; and Sambrook et al., supra).

A number of procedures can be employed when recombinant CMAH is being purified. For example, proteins having established molecular adhesion properties can be reversible fused to CMAH. With the appropriate ligand, CMAH can be selectively adsorbed to a purification column and then freed from the column in a relatively pure form. The fused protein is then removed by enzymatic activity. Finally CMAH could be purified using immunoaffinity columns.

1. Purification of CMAH from Recombinant Bacteria

Recombinant proteins are expressed by transformed bacteria in large amounts, typically after promoter induction; but expression can be constitutive. Promoter induction with IPTG is a one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of CMAH inclusion bodies. For example, purification of inclusion bodies typically involves the extraction, separation and/or purification of inclusion bodies by disruption of bacterial cells, e.g., by incubation in a buffer of 50 mM Tris/HCl pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. CMAH is separated from other bacterial proteins by standard separation techniques, e.g., with Ni-NTA agarose resin.

Alternatively, it is possible to purify CMAH from bacteria periplasm. After lysis of the bacteria, when CMAH is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

E. Standard Protein Separation Techniques for Purifying CMAH

1. Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

2. Size Differential Filtration

The molecular weight of CMAH can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

3. Column Chromatography

CMAH can also be separated from other proteins on the basis of their size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Alternatively, CMAH protein can be expressed transiently in a cell by introducing into a cell an RNA encoding the CMAH protein. The RNA is transcribed in vitro according to standard procedures and then introduced into a cell (e.g. such as *Xenopus* oocytes, CHO, and HeLa cells) by means such as injection or electroporation. The RNA then expresses the CMAH protein.

IV. Detection of CMAH Nucleic Acid Sequences

Determination of the presence of absence of a particular mutant CMAH gene is generally performed by analyzing a nucleic acid sample that is obtained from a cat (e.g., of the genus *felis, panthera, neofelis*, or *acinonyx*) to be analyzed. Often, the nucleic acid sample comprises genomic DNA. It is also possible to analyze RNA samples for the presence of CMAH mutations.

Detection techniques for evaluating nucleic acids for the presence of a single base change involve procedures well known in the field of molecular genetics. Further, many of the methods involve amplification of nucleic acids. Ample guidance for performing the methods is provided in the art. Exemplary references include manuals such as PCR Technology: PRINCIPLES AND APPLICATIONS FOR DNA AMPLIFICATION (ed. H. A. Erlich, Freeman Press, NY, N.Y., 1992); PCR PROTOCOLS: A GUIDE TO METHODS AND APPLICATIONS (eds. Innis, et al., Academic Press, San Diego, Calif., 1990); CURRENT PROTOCOLS IN MOLECULAR BIOLOGY, Ausubel, 1994-1999, including supplemental updates through April 2004; Sambrook & Russell, *Molecular Cloning, A Laboratory Manual* (3rd Ed, 2001).

Methods for detecting single base changes well known in the art often entail one of several general protocols: hybridization using sequence-specific oligonucleotides, primer extension, sequence-specific ligation, sequencing, or electrophoretic separation techniques, e.g., singled-stranded conformational polymorphism (SSCP) and heteroduplex analysis. Exemplary assays include 5' nuclease assays, template-directed dye-terminator incorporation, molecular beacon allele-specific oligonucleotide assays, single-base extension assays, and SNP scoring by real-time pyrophosphate sequences. Analysis of amplified sequences can be performed using various technologies such as microchips, fluorescence polarization assays, and matrix-assisted laser desorption ionization (MALDI) mass spectrometry. In addition to these frequently used methodologies for analysis of nucleic acid samples to detect single base changes, any method known in the art can be used to detect the presence of the CMAH mutations described herein.

Although the methods typically employ PCR steps, other amplification protocols may also be used. Suitable amplification methods include ligase chain reaction (see, e.g., Wu & Wallace, *Genomics* 4:560-569, 1988); strand displacement assay (see, e.g., Walker et al., *Proc. Natl. Acad. Sci. USA* 89:392-396, 1992; U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., *Proc. Natl. Acad. Sci. USA* 86:1173-1177, 1989); and self-sustained sequence replication (3SR) (Guatelli et al., *Proc. Natl. Acad. Sci. USA* 87:1874-1878, 1990; WO 92/08800). Alternatively, methods that amplify the probe to detectable levels can be used, such as Qβ-replicase amplification (Kramer & Lizardi, *Nature* 339:401-402, 1989; Lomeli et al., *Clin. Chem.* 35:1826-1831, 1989). A review of known amplification methods is provided, for example, by Abramson and Myers in *Current Opinion in Biotechnology* 4:41-47, 1993.

In some embodiments, the mutant CMAH is detected using oligonucleotide primers and/or probes. Oligonucleotides can be prepared by any suitable method, including chemical synthesis. Oligonucleotides can be synthesized using commercially available reagents and instruments. Alternatively, they can be purchased through commercial sources. Methods of synthesizing oligonucleotides are well known in the art (see, e.g., Narang et al., *Meth. Enzymol.* 68:90-99, 1979; Brown et al., *Meth. Enzymol.* 68:109-151, 1979; Beaucage et al., *Tetrahedron Lett.* 22:1859-1862, 1981; and the solid support method of U.S. Pat. No. 4,458,066).

B. PCR Determination of Blood Type

PCR can be used to determine blood type by amplification of nucleic acids encoding CMAH. A general overview of the applicable technology can be found in PCR Protocols: A Guide to Methods and Applications (Innis et al. eds. (1990)) and PCR Technology: Principles and Applications for DNA Amplification (Erlich, ed. (1992)). In addition, amplification technology is described in U.S. Pat. Nos. 4,683,195 and 4,683,202.

PCR permits the copying, and resultant amplification of a target nucleic acid, e.g., a nucleic acid encoding CMAH. Briefly, a target nucleic acid, e.g. DNA from a biological sample from a subject to be blood typed is combined with a sense and antisense primers, dNTPs, DNA polymerase and other reaction components. (See, Innis et al., supra) The sense primer can anneal to the antisense strand of a DNA sequence of interest. The antisense primer can anneal to the sense strand of the DNA sequence, downstream of the location where the sense primer anneals to the DNA target. In the first round of amplification, the DNA polymerase extends the antisense and sense primers that are annealed to the target nucleic acid. The first strands are synthesized as long strands of indiscriminate length. In the second round of amplification, the antisense and sense primers anneal to the parent target nucleic acid and to the complementary sequences on the long strands. The DNA polymerase then extends the annealed primers to form strands of discrete length that are complementary to each other. The subsequent rounds serve to predominantly amplify the DNA molecules of the discrete length.

In general, PCR and other methods of amplification use primers which anneal to either end of the DNA sequence of interest. For example, nucleic acids encoding mutant CMAH or fragments thereof may be amplified using isolated nucleic acid primer pairs having the following sequences: 5' primer: TTCCTTTGCTGCTGGAGTG (SEQ ID NO:4) and 3' primer CAACACTGAGCAAGCAGAGC (SEQ ID NO:6) (exon 1-5' UTR); 5' primer: CAACACTGAGCAAGCAGAGC (SEQ ID NO:6) and 3' primer GGTTTCCTCTCTCTCAGGGG (SEQ ID NO:60) (exon 2), among others. Amplification of DNA encoding one of the mutations in CMAH identified in Table 1 from a biological sample from a subject being blood typed is indicative of the blood type of the subject.

Target nucleic acid sequences may be double or single-stranded DNA or RNA from any biological sample from a subject to be blood typed. Preferably, the target template is an isolated DNA sequence. Target DNA sequences may be isolated using a variety of techniques. For example, methods are known for lysing organisms and preparing extracts or purifying DNA. See, Current Protocols in Molecular Biology Volumes 1-3, John Wiley & Sons, Inc. (Ausubel et al., eds., 1994-1998) (hereinafter "Ausubel et al."). Also, total RNA or polyA+ RNA can be reverse transcribed to produce cDNA that can serve as the target DNA.

B. Reaction Components

1. Oligonucleotides

The oligonucleotides that are used in the present invention as well as oligonucleotides designed to detect amplification products can be chemically synthesized, as described above. These oligonucleotides can be labeled with radioisotopes, chemiluminescent moieties, or fluorescent moieties. Such labels are useful for the characterization and detection of amplification products using the methods and compositions of the present invention.

The primer components may be present in the PCR reaction mixture at a concentration of, e.g., between 0.1 and 1.0 µM. The concentration of the target primers can be from about 0.1 to about 0.75 µM. The primer length can be between, e.g., 15-100 nucleotides in length and preferably have 40-60% G and C composition. In the choice of primer, it is preferable to have exactly matching bases at the 3' end of the primer but this requirement decreases to relatively insignificance at the 5' end. Preferably, the primers of the invention all have approximately the same melting temperature.

Typically, the primers have the following design. The most 3' portion anneals to the constant region flanking the target region to be amplified, this portion will normally have at least 6 bp of homology to the target region, preferably 9 or more bp. The region of homology is adjacent to the restriction enzyme sequence. If this recognition site is an interrupted sequence, the intervening portion of sequence between the two portions of the restriction enzyme site will normally contain bases which can anneal to the appropriate portion of the constant region flanking the target of interest. 5' to the restriction enzyme site are sufficient bases to allow the restriction enzyme to recognize its site and cleave the recognized sequence. Where the restriction enzyme site cleaves twice, once on either side of the recognition site, the primer should be sufficiently long to allow the enzyme to cleave at both of the cleavage sites. The extra nucleotides may or may not have further homology to the constant region flanking the target of interest.

2. Buffer

Buffers that may be employed are borate, phosphate, carbonate, barbital, Tris, etc. based buffers. (See, U.S. Pat. No. 5,508,178). The pH of the reaction should be maintained in the range of about 4.5 to about 9.5. (See, U.S. Pat. No. 5,508,178. The standard buffer used in amplification reactions is a Tris based buffer between 10 and 50 mM with a pH of around 8.3 to 8.8. (See Innis et al., supra.).

One of skill in the art will recognize that buffer conditions should be designed to allow for the function of all reactions of interest. Thus, buffer conditions can be designed to support the amplification reaction as well as any subsequent restriction enzyme reactions. A particular reaction buffer can be tested for its ability to support various reactions by testing the reactions both individually and in combination.

3. Salt Concentration

The concentration of salt present in the reaction can affect the ability of primers to anneal to the target nucleic acid. (See, Innis et al.). Potassium chloride is added up to a concentration of about 50 mM to the reaction mixture to promote primer annealing. Sodium chloride can also be added to promote primer annealing. (See, Innis et al.).

4. Magnesium Ion Concentration

The concentration of magnesium ion in the reaction can affect amplification of the target sequence(s). (See, Innis et al.). Primer annealing, strand denaturation, amplification specificity, primer-dimer formation, and enzyme activity are all examples of parameters that are affected by magnesium concentration. (See, Innis et al.). Amplification reactions should contain about a 0.5 to 2.5 mM magnesium concentration excess over the concentration of dNTPs. The presence of magnesium chelators in the reaction can affect the optimal magnesium concentration. A series of amplification reactions can be carried out over a range of magnesium concentrations to determine the optimal magnesium concentration. The optimal magnesium concentration can vary depending on the nature of the target nucleic acid(s) and the primers being used, among other parameters.

5. Deoxynucleotide Triphosphate Concentration

Deoxynucleotide triphosphates (dNTPs) are added to the reaction to a final concentration of about 20 µM to about 300 µM. Typically, each of the four dNTPs (G, A, C, T) are present at equivalent concentrations. (See, Innis et al.).

6. Nucleic Acid Polymerase

A variety of DNA dependent polymerases are commercially available that will function using the methods and compositions of the present invention. For example, Taq DNA Polymerase may be used to amplify target DNA sequences. The PCR assay may be carried out using as an enzyme component a source of thermostable DNA polymerase suitably comprising Taq DNA polymerase which may be the native enzyme purified from *Thermus aquaticus* and/or a genetically engineered form of the enzyme. Other commercially available polymerase enzymes include, e.g., Taq polymerases marketed by Promega or Pharmacia. Other examples of thermostable DNA polymerases that could be used in the invention include DNA polymerases obtained from, e.g., *Thermus* and *Pyrococcus* species. Concentration ranges of the polymerase may range from 1-5 units per reaction mixture. The reaction mixture is typically between 20 and 100 µl.

In some embodiments, a "hot start" polymerase can be used to prevent extension of mispriming events as the temperature of a reaction initially increases. Hot start polymerases can have, for example, heat labile adducts requiring a heat activation step (typically 95° C. for approximately 10-15 minutes) or can have an antibody associated with the polymerase to prevent activation.

7. Other Agents

Additional agents are sometimes added to the reaction to achieve the desired results. For example, DMSO can be added to the reaction, but is reported to inhibit the activity of Taq DNA Polymerase. Nevertheless, DMSO has been recommended for the amplification of multiple target sequences in the same reaction. (See, Innis et al. supra). Stabilizing agents such as gelatin, bovine serum albumin, and non-ionic detergents (e.g. Tween-20) are commonly added to amplification reactions. (See, Innis et al. supra).

C. Detection of Amplified Products

Amplified products can be detected using any means known in the art, including, e.g., restriction fragment length polymorphism (RFLP) analysis; denaturing gel electrophoresis, direct sequencing, and HPLC-based analysis.

1. RFLP Analysis

In some embodiments, a mutant CMAH gene is detected using restriction fragment length polymorphism (RFLP) analysis. A subsequence of CMAH is amplified from a biological sample from a cat. The amplification products are digested with a restriction enzyme. If the restriction site is present in the mutant CMAH but not the wild-type CMAH, the mutant sequences will be digested, but the wild type will not. Conversely if the restriction site is present in the wild-type CMAH, but not the mutant CMAH, the wild-type sequences will be digested, but the mutant will not. The restriction fragments are then analyzed using gel electrophoresis. Further analysis to confirm the sequence can be performed as described herein.

2. Sequencing

The mutant CMAH genes are typically detected by direct sequencing, e.g., to detect the 18 bp insertion at position −53 of exon 1 of CMAH; a G to A substitution in exon 2 at position 139 of CMAH or to detect the sequences set forth in SEQ ID NOS: 1 or 2, among others. Methods include e.g., dideoxy sequencing-based methods and Maxam and Gilbert sequence (see, e.g., Sambrook and Russell, supra).

3. HPLC

Mutant CMAH sequences can be differentiated using high performance liquid chromatography (HPLC) based methods including denaturing HPLC (dHPLC) as described in e.g., Premstaller and Oefner, *LC-GC Europe* 1-9 (July 2002); Bennet et al., *BMC Genetics* 2:17 (2001); Schrimi et al., *Biotechniques* 28(4):740 (2000); and Nairz et al., *PNAS USA* 99(16): 10575-10580 (2002); and ion-pair reversed phase HPLC-electrospray ionization mass spectrometry (ICEMS) as described in e.g., Oberacher et al.; *Hum. Mutat.* 21(1):86 (2003).

Partially denaturing HPLC analysis compares two or more sets of amplified products (e.g., a wild-type CMAH amplicon and a mutant CMAH amplicon). The amplified products are denatured (e.g., at about 95° C.) and allowed to reanneal by gradually lowering the temperature from about 95° C. to about 30° C. In the presence of a CMAH mutation the original homoduplex products are reformed along with heteroduplex products comprising the sense and anti-sense strands of either homoduplex. The homoduplexes and heteroduplexes are loaded onto an HPLC apparatus at a partially denaturing temperature of about 50° C. to about 70° C. and can be distinguished based on their elution profile. Completely denaturing HPLC analysis compares two or more sets of amplicons (e.g., primer extension products). The amplified products are loaded onto an HPLC apparatus at a completely denaturing temperature of about 70° C. to about 80° C. Specific sequence variants are eluted from the column by varying the temperature of the column and sequence variants are distinguished based on their order of elution from the column.

Ion-pair reversed phase HPLC-electrospray ionization mass spectrometry (ICEMS) uses a combination of HPLC under completely denaturing conditions and ICEMS to resolve differences between nucleic acid sequences.

4. Denaturing Gradient Gel Electrophoresis

Amplification products generated using the polymerase chain reaction can be analyzed by the use of denaturing gradient gel electrophoresis. Different CMAH mutations can be identified based on the different sequence-dependent melting properties and electrophoretic migration of DNA in solution (see, e.g., Erlich, ed., PCR TECHNOLOGY, PRINCIPLES AND APPLICATIONS FOR DNA AMPLIFICATION, W. H. Freeman and Co, New York, 1992, Chapter 7).

5. Single Base Extensions

Another method for characterizing single base changes in CMAH does not require use of a complete PCR, but typically uses only the extension of a primer by a single, fluorescence-labeled dideoxyribonucleic acid molecule (ddNTP) that is complementary to the nucleotide to be investigated. The nucleotide at the site of the CMAH mutation can be identified via detection of a primer that has been extended by one base and is fluorescently labeled (e.g., Kobayashi et al, *Mol. Cell. Probes,* 9:175-182, 1995).

6. Single-Strand Conformation Polymorphism Analysis

Mutant CMAH sequences can be differentiated using single-strand conformation polymorphism analysis, which identifies base differences by alteration in electrophoretic migration of single stranded PCR products, as described, e.g., in Orita et al., *Proc. Nat. Acad. Sci.* 86, 2766-2770 (1989). Amplified PCR products can be generated using methods known in the art, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between wild type and mutant CMAH sequences.

Methods for detecting single base changes often employ labeled oligonucleotides. Oligonucleotides can be labeled by incorporating a label detectable by spectroscopic, photochemical, biochemical, immunochemical, or chemical means. Useful labels include fluorescent dyes, radioactive labels, e.g., $^{32}P$, electron-dense reagents, enzyme, such as peroxidase or alkaline phosphatase, biotin, or haptens and proteins for which antisera or monoclonal antibodies are available. Labeling techniques are well known in the art (see, e.g., Current Protocols in Molecular Biology, supra; Sambrook & Russell, supra).

7. Sequence Specific Hybridization

A technique commonly referred to as allele specific oligonucleotide hybridization (ASO) (e.g., Stoneking et al., *Am. J. Hum. Genet.* 48:70-382, 1991; Saiki et al., *Nature* 324, 163-166, 1986; EP 235,726; and WO 89/11548) can used to detect mutant CMAH genes. Two DNA molecules differing by one base are distinguished by hybridizing an oligonucleotide probe that is specific for one of the variants (e.g., wild type or mutant CMAH) to an amplified product obtained from amplifying the nucleic acid sample. The probes are designed to differentially hybridize to one variant versus another. Principles and guidance for designing such probes is available in the art (see, e.g., Jeffrys and Mays, *Genome Res.* 13(1): 2316-2324 (2003) and Howell et al., *Nature Biotech* 17(1): 87-88 (1999)). Hybridization conditions should be sufficiently stringent that there is a significant difference in hybridization intensity between alleles, and preferably an essentially binary response, whereby a probe hybridizes to only one of the sequences.

The presence of a CMAH mutation is determined by measuring the amount of sequence-specific oligonucleotide that is hybridized to the sample. Typically, the oligonucleotide is labeled with a label such as a fluorescent label. For example, a mutant CMAH-specific oligonucleotide is applied to immobilized oligonucleotides representing CMAH sequences. After stringent hybridization and washing conditions, fluorescence intensity is measured for each CMAH oligonucleotide.

For example, the nucleotide present at the site of the CMAH mutation is identified by hybridization under sequence-specific hybridization conditions with an oligonucleotide probe exactly complementary to a CMAH mutation in a region encompassing the CMAH mutation. The probe hybridizing sequence and sequence-specific hybridization conditions are selected such that a single mismatch at the mutation site destabilizes the hybridization duplex sufficiently so that it is effectively not formed. Thus, under sequence-specific hybridization conditions, stable duplexes will form only between the probe and the exactly complementary CMAH sequence.

Suitable assay formats for detecting hybrids formed between probes and target nucleic acid sequences in a sample are known in the art and include the immobilized target (dot-blot) format and immobilized probe (reverse dot-blot or line-blot) assay formats. Dot blot and reverse dot blot assay formats are described in U.S. Pat. Nos. 5,310,893; 5,451,512; 5,468,613; and 5,604,099; each incorporated herein by reference.

In a dot-blot format, amplified target DNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe. A preferred dot-blot detection assay is described in the examples.

In the reverse dot-blot (or line-blot) format, the probes are immobilized on a solid support, such as a nylon membrane or a microtiter plate. The target DNA is labeled, typically during amplification by the incorporation of labeled primers. One or both of the primers can be labeled. The membrane-probe complex is incubated with the labeled amplified target DNA under suitable hybridization conditions, unhybridized target DNA is removed by washing under suitably stringent conditions, and the membrane is monitored for the presence of bound target DNA. A preferred reverse line-blot detection assay is described in the examples.

An allele-specific probe that is specific for one of the polymorphism variants is often used in conjunction with the allele-specific probe for the other polymorphism variant. In some embodiments, the probes are immobilized on a solid support and the target sequence in an individual is analyzed using both probes simultaneously. Examples of nucleic acid arrays are described by WO 95/11995. The same array or a different array can be used for analysis of characterized polymorphisms. WO 95/11995 also describes subarrays that are optimized for detection of variant forms of a pre-characterized polymorphism. Such a subarray can be used in detecting the presence of the mutant CMAH gene described herein.

8. Sequence-Specific Primers

Mutations are also commonly detected using sequence-specific amplification or primer extension methods. These reactions typically involve use of primers that are designed to specifically target a polymorphism via a mismatch at the 3' end of a primer. The presence of a mismatch effects the ability of a polymerase to extend a primer when the polymerase lacks error-correcting activity. For example, to detect a CMAH sequence using a CMAH-specific amplification- or extension-based method, a primer complementary to the wild type or mutant CMAH gene is designed such that the 3' terminal nucleotide hybridizes at the mutation site. The presence of the CMAH mutation can be determined by the ability of the primer to initiate extension. If the 3' terminus is mismatched, the extension is impeded. Thus, for example, if a primer matches the CMAH mutation at the 3' end, the primer matches and will be efficiently extended.

Typically, the primer is used in conjunction with a second primer in an amplification reaction. The second primer hybridizes at a site unrelated to the polymorphic position. Amplification proceeds from the two primers leading to a detectable product signifying the particular allelic form is present. Sequence-specific amplification- or extension-based methods are described in, for example, WO 93/22456; U.S. Pat. Nos. 5,137,806; 5,595,890; 5,639,611; and U.S. Pat. No. 4,851,331.

Using sequence-specific amplification-based genotyping, identification of the mutations requires only detection of the presence or absence of amplified target sequences. Methods for the detection of amplified target sequences are well known in the art. For example, gel electrophoresis and probe hybridization assays described are often used to detect the presence of nucleic acids.

In an alternative probe-less method, the amplified nucleic acid is detected by monitoring the increase in the total amount of double-stranded DNA in the reaction mixture, is described, e.g., in U.S. Pat. No. 5,994,056; and European Patent Publication Nos. 487,218 and 512,334. The detection of double-stranded target DNA relies on the increased fluorescence various DNA-binding dyes, e.g., SYBR® Green, exhibit when bound to double-stranded DNA.

As appreciated by one in the art, sequence-specific amplification methods, can be performed in reaction that employ multiple sequence-specific primers to target particular mutations. Primers for such multiplex applications are generally labeled with distinguishable labels or are selected such that the amplification products produced from the target sequences are distinguishable by size. Thus, for example, the presence of both a wild type and mutant CMAH gene in a single sample can be identified using a single amplification by gel analysis of the amplification product.

As in the case of sequence-specific probes, a sequence-specific oligonucleotide primer may be exactly complementary to one of the CMAH mutants in the hybridizing region or may have some mismatches at positions other than the 3' terminus of the oligonucleotide, which mismatches occur away from the site of the CMAH mutation.

D. 5'-Nuclease Assay

Genotyping can also be performed using a "TaqMan®" or "5'-nuclease assay", as described in U.S. Pat. Nos. 5,210,015; 5,487,972; and 5,804,375; and Holland et al., 1988, *Proc. Natl. Acad. Sci. USA* 88:7276-7280. In the TaqMan® assay, labeled detection probes that hybridize within the amplified region are added during the amplification reaction. The probes are modified so as to prevent the probes from acting as primers for DNA synthesis. The amplification is performed using a DNA polymerase having 5' to 3' exonuclease activity. During each synthesis step of the amplification, any probe which hybridizes to the target nucleic acid downstream from the primer being extended is degraded by the 5' to 3' exonuclease activity of the DNA polymerase. Thus, the synthesis of a new target strand also results in the degradation of a probe, and the accumulation of degradation product provides a measure of the synthesis of target sequences.

The hybridization probe can be a sequence-specific probe that discriminates between wild type and mutant CMAH. Alternatively, the method can be performed using a sequence-specific primer and a labeled probe that binds to amplified product.

Any method suitable for detecting degradation product can be used in a 5' nuclease assay. Often, the detection probe is labeled with two fluorescent dyes, one of which is capable of quenching the fluorescence of the other dye. The dyes are attached to the probe, preferably one attached to the 5' terminus and the other is attached to an internal site, such that quenching occurs when the probe is in an unhybridized state and such that cleavage of the probe by the 5' to 3' exonuclease activity of the DNA polymerase occurs in between the two dyes. Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673 describe alternative methods for detecting the degradation of probe which occurs concomitant with amplification.

In some cases, mRNA can also be used to determine the whether a cat carries a CMAH mutation associated with a particular blood type. Such an analysis can be performed by first reverse-transcribing the target RNA from a biological sample from the cat using, for example, a viral reverse transcriptase, and then amplifying the resulting cDNA; or using a combined high-temperature reverse-transcription-polymerase chain reaction (RT-PCR), as described in U.S. Pat. Nos. 5,310,652; 5,322,770; 5,561,058; 5,641,864; and 5,693,517.

V. Immunological Detection of Mutant CMAH

In addition to the determination of blood type by detection of mutant CMAH genes and gene expression using nucleic acid hybridization technology, one can also use immunoassays to determine blood type by detecting mutant CMAH or antibodies that specifically bind to them. Immunoassays can be used to qualitatively or quantitatively analyze mutant CMAH. A general overview of the applicable technology can be found in Harlow & Lane, Antibodies: A Laboratory Manual (1988).

A. Antibodies to Mutant CMAH

Methods of producing polyclonal and monoclonal antibodies that react specifically with mutant CMAH, or immunogenic fragments of mutant CMAH, are known to those of skill in the art (see, e.g., Coligan, Current Protocols in Immunology (1991); Harlow & Lane, supra; Goding, Monoclonal Antibodies: Principles and Practice (2d ed. 1986); and Kohler & Milstein, Nature 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of immunogens comprising portions of mutant CMAH may be used to produce antibodies specifically reactive with mutant CMAH or homologues thereof. For example, recombinant mutant CMAH (encoded by SEQ ID NO: 1) or antigenic fragments thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-CMAH proteins, using a competitive binding immunoassay. Specific polyclonal antisera and monoclonal antibodies will usually bind with a Kd of at least about 0.1 mM, more usually at least about 1 µM, preferably at least about 0.1 µM or better, and most preferably, 0.01 µM or better. Antibodies specific only for a particular CMAH homologue, such as feline CMAH, can also be made, by subtracting out other cross-reacting homologues from a species such as a non-human mammal.

Once the specific antibodies against a CMAH are available, CMAH homologues can be detected by a variety of immunoassay methods. For a review of immunological and immunoassay procedures, see Basic and Clinical Immunology (Stites & Terr eds., 7th ed. 1991). Moreover, the immunoassays of the present invention can be performed in any of several configurations, which are reviewed extensively in Enzyme Immunoassay (Maggio, ed., 1980); and Harlow & Lane, supra. Additional assay configurations (i.e., using multiplex assays using microspheres) are described in, e.g., De Jager et al., *Clin. Diagn. Lab. Immunol.* 10(1):13309 (2003); Earley et al., *Cytometry* 50(5):239-42 (2002); and Seidman and Peritt, *J. Immunol. Methods* 267(2):165-71 (2002).

In one exemplary embodiment, the immunoassays are performed using Luminex technology. With Luminex technology, molecular reactions take place on the surface of microscopic beads called microspheres (Literature from Luminex Corporation, Austin, Tex.). For each reaction in a Luminex profile, thousands of molecules are attached to the surface of internally color-coded microspheres. The assigned color-code identifies each reaction throughout the test. The magnitude of the biomolecular reaction is measured using a second molecule called a reporter which can be a secondary antibody labeled with color. The reporter molecule signals the extent of the reaction by attaching to the molecules on the microspheres. Because the reporter's signal is also a color, there are two sources of color, the color-code inside the microsphere and the reporter color on the surface of the microsphere. To perform a test, the color-coded microspheres, reporter molecules, and sample are combined. This mixture is then injected into an instrument that uses microfluidics to align the microspheres in single file where lasers illuminate the colors inside and on the surface of each microsphere. Next, advanced optics capture the color signals. Finally, digital signal processing translates the signals into real-time, quantitative data for each reaction. The advantages of this Luminex techniques are that multiplex antigens representing different pathogens can be tested with single serum sample, therefore, it saves on labor, reagents, time and samples: and that it makes high throughput (20,000 microsphere per second) possible and shortens analysis time. For example, one color coded beads can be coated with wild type CMAH, and a different color coded beads can be coated with mutant CMAH: and 2 sets of beads can be mixed and reacted with the same fluid sample to determine whether the sample has wild type CMAH, mutant CMAH, or both by a single test.

B. Immunological Binding Assays

The CMAH polypeptides of the invention and antibodies that specifically bind to them can be detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology: Antibodies in Cell Biology, volume 37 (Asai, ed. 1993); Basic and Clinical Immunology (Stites & Terr, eds., 7th ed. 1991). Immunological binding assays (or immunoassays) typically use an antibody that specifically binds to a protein or antigen of choice (in this case CMAH or an immunogenic fragment thereof). The antibody (e.g., anti-CMAH) may be produced by any of a number of means well known to those of skill in the art and as described above. Alternatively, a protein or antigen of choice (in this case CMAH, or an immunogenic fragment thereof) may be used to bind antibodies that specifically bind to the protein or antigen. The protein or antigen may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled CMAH polypeptide or a labeled anti-CMAH antibody. Alternatively, the labeling agent may be a third moiety, such a secondary antibody, which specifically binds to the antibody/CMAH complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135: 2589-2542 (1985)). The labeling agent can be modified with a detectable moiety, such as biotin, to which another molecule can specifically bind, such as streptavidin. The streptavidin may be bound to a label or detectable group as discussed below. A variety of detectable moieties are well known to those skilled in the art.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecule (e.g., streptavidin), which is either inherently detectable or covalently bound to a signal system, such as a detectable enzyme, a fluorescent compound, or a chemiluminescent compound. The ligands and their targets can be used in any suitable combination with antibodies that recognize CMAH, or secondary antibodies that recognize anti-CMAH antibodies.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

1. Non-Competitive Assay Formats

Immunoassays for detecting CMAH or immunogenic fragments thereof in samples may be either competitive or non-competitive. Noncompetitive immunoassays are assays in which the amount of antigen is directly measured. In one preferred "sandwich" assay, for example, the anti-CMAH antibodies can be bound directly to a solid substrate on which they are immobilized. These immobilized antibodies then capture CMAH present in the test sample. CMAH are thus immobilized and then bound by a labeling agent, such as a second CMAH antibody bearing a label. Alternatively, the second antibody may lack a label, but it may, in turn, be bound by a labeled third antibody specific to antibodies of the species from which the second antibody is derived. The second or third antibody is typically modified with a detectable label, such as biotin, to which another molecule specifically binds, e.g., streptavidin, to provide a detectable moiety.

Noncompetitive immunoassays may also be assays in which the amount of anti-CMAH antibody is directly measured. CMAH or an immunogenic fragment thereof can be bound directly to a solid substrate on which they are immobilized. The immobilized CMAH then captures anti-CMAH antibodies present in the test sample. Anti-CMAH antibodies are thus immobilized and then bound by a labeling agent, such as an anti-Fc antibody bearing a label. The anti-Fc antibody may be, for example, an anti-mouse Fc antibody, an anti-rat Fc antibody, or an anti-rabbit Fc antibody. Those of skill in the art will appreciate that any suitable anti-Fc antibody may be selected for use in this type of assay. Alternatively, the anti-Fc antibody may lack a label, but it may, in turn, be bound by a labeled third antibody specific to antibodies of the species from which the second antibody is derived. The second or third antibody is typically modified with a detectable label, such as biotin, to which another molecule specifically binds, e.g., streptavidin, to provide a detectable moiety.

2. Competitive Assay Formats

In competitive assays, the amount of the CMAH present in the sample is measured indirectly by measuring the amount of known, added (exogenous) CMAH displaced (competed away) from an anti-CMAH antibody by the unknown CMAH present in a sample. In one competitive assay, a known amount of the CMAH is added to a sample and the sample is then contacted with an antibody that specifically binds to the CMAH. The amount of exogenous CMAH bound to the antibody is inversely proportional to the concentration of the CMAH present in the sample. In a particularly preferred embodiment, the antibody is immobilized on a solid substrate. The amount of CMAH bound to the antibody may be determined either by measuring the amount of CMAH present in a CMAH/antibody complex, or alternatively by measuring the amount of remaining uncomplexed protein. The amount of CMAH may be detected by providing a labeled CMAH molecule.

A hapten inhibition assay is another preferred competitive assay. In this assay the known CMAH is immobilized on a solid substrate. A known amount of anti-CMAH antibody is added to the sample, and the sample is then contacted with the immobilized CMAH. The amount of anti-CMAH antibody bound to the known immobilized CMAH is inversely proportional to the amount of CMAH present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

3. Cross-Reactivity Determinations

Immunoassays in the competitive binding format can also be used for crossreactivity determinations for CMAH homologues. For example, a CMAH protein at least partially corresponding to a polypeptide sequence encoded by SEQ ID NOS: 1, 2, or 3 or an immunogenic fragment thereof, (e.g., the polypeptide encoded by exon 29 of CMAH, can be immobilized to a solid support. Other proteins such as CMAH homologues or other proteins from other cat species, are added to the assay so as to compete for binding of the antisera to the immobilized antigen. The ability of the added proteins to compete for binding of the antisera to the immobilized protein is compared to the ability of the CMAH or immunogenic portion thereof to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologues. Antibodies that specifically bind only to CMAH, or only to particular homologues of CMAH can also be made using this methodology.

The immunoabsorbed and pooled antisera are then used in a competitive binding immunoassay as described above to compare a second protein, thought to be perhaps a CMAH homologue or an allele, or polymorphic variant of CMAH, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by CMAH that is required to inhibit 50% of binding, then the second protein is said to specifically bind to the polyclonal antibodies generated to the respective CMAH immunogen.

4. Other Assay Formats

Western blot (immunoblot) analysis is used to detect and quantify the presence of the CMAH polypeptides in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind CMAH polypeptides. The anti-CMAH antibodies specifically bind to CMAH on the solid support, thereby forming an antibody-polypeptide complex. These antibodies may be directly labeled or alternatively may be subsequently detected using labeled antibodies (e.g., labeled sheep anti-mouse antibodies) that specifically bind to the anti-CMAH antibodies.

Other assay formats include liposome immunoassays (LIA), which use liposomes designed to bind specific molecules (e.g., antibodies) and release encapsulated reagents or markers. The released chemicals are then detected according to standard techniques (see, Monroe et al., Amer. *Clin. Prod. Rev.* 5:34-41 (1986)).

5. Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

VI. Cytidine Monophospho-N-Acetylneuraminic Acid Hydroxylase (CMAH) Assays

Functional cytidine monophospho-N-acetylneuraminic acid hydroxylase (CMAH) assays known in the art can also be used to identify CMAH mutants (see, e.g., Muchmore, E. A. et al., J. Biol Chem., 264:20216-20223 (1989)). For example, a biological sample from a cat can be contacted with a CMAH substrate such as NeuAc to determine whether the cat is carrier for a CMAH mutation (B blood type) or has a wild-type CMAH (blood type A).

VII. Kits

CMAH and its homologues are useful tools for more specific and sensitive identification of blood type in cats. CMAH specific reagents that specifically hybridize to CMAH nucleic acid, such as CMAH probes and primers (e.g., as set forth in SEQ ID NO: 4-27), CMAH nucleic acids (e.g. as set forth in SEQ ID NO: 1 and 2), and CMAH specific reagents that specifically bind to the CMAH protein, e.g., CMAH antibodies can be used to determine blood type.

Nucleic acid assays for the presence of CMAH DNA and RNA in a sample include numerous techniques are known to those skilled in the art, such as Southern analysis, northern analysis, dot blots, RNase protection, S1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., Biotechniques 4:230-250 (1986); Haase et al., Methods in Virology, vol. VII, pp. 189-226 (1984); and Nucleic Acid Hybridization: A Practical Approach (Hames et al., eds. 1987). In addition, CMAH protein can be detected with the various immunoassay techniques described above, e.g., ELISA, western blots, etc. The test sample is typically compared to both a positive control (e.g., a sample expressing recombinant CMAH) and a negative control. A wide variety of kits and components can be prepared according to the present invention, depending upon the intended user of the kit and the particular needs of the user. For example, the kit can be tailored for in vitro or in vivo assays.

The invention also provides kits and solutions for carrying out the amplification methods of the invention. For example, the invention provides kits that include one or more reaction vessels that have aliquots of some or all of the reaction components of the invention in them. Aliquots can be in liquid or dried form. Reaction vessels can include sample processing cartridges or other vessels that allow for the containment, processing and/or amplification of samples in the same vessel. Such kits allow for ready detection of amplification products of the invention into standard or portable amplification devices. The kits can also include written instructions for the use of the kit to amplify and control for amplification of a target sample.

Kits can include, for instance, amplification reagents comprising primers sufficient to amplify at least two different target sequences, a polynucleotide sequence comprising the sequences of the primers or subsequences of the primers as described herein; and at least one probe for amplifying and detecting the polynucleotide sequence. In addition, the kit can include nucleotides (e.g., A, C, G and T), a DNA polymerase and appropriate buffers, salts and other reagents to facilitate amplification reactions.

In some embodiments, the kits comprise vessels such as sample processing cartridges useful for rapid amplification of a sample as described in Belgrader, et al., *Biosensors and Bioelectronics* 14:849-852 (2000); Belgrader, et al., *Science,* 284:449-450 (1999); and Northrup, M. A., et al. "A New Generation of PCR Instruments and Nucleic Acid Concentration Systems" in PCR PROTOCOLS (Sninsky, J. J. et al (eds.)) Academic, San Diego, Chapter 8 (1998)).

EXAMPLES

The following examples are offered to illustrate, but not to limit the claimed invention.

Example 1

Materials and Methods

Sampling

To maintain clarity within the discussions, cats that are obligate carriers of type B are presented as type Ab, whereas the third, less defined blood group, will be presented in the traditional manner as type AB. Whole blood anti-coagulated with EDTA or buccal swab samples from non-related, as well as related cats with A, B and AB blood types were obtained from owners in the USA. European cat DNA samples, which were received as part of a blood typing service, were also provided by the collaborating service laboratory (Oy Triniini Company, Helsinki, Finland). The samples (N=221) included 107 type A, 79 type B and 35 type AB cats representing 18 breeds (Table 1). The sample set included two non-purebred domestic shorthairs and 12 obligate carrier F1 hybrid cats produced by crossing a type B Persian with two type A Oriental Shorthairs, thus producing type Ab. Two purebred pedigrees segregating for the A and B blood types were developed for the British Shorthair (N=31) and Birman (N=13) cat breeds (FIG. 2a, b). Relationships within the pedigrees were confirmed with a publicly available microsatellite-based parentage testing panel for the cat (data not shown).

Blood types were determined using RapidVet-H Feline Blood Type Cards (DMS Laboratories, Flemington, N.J.). Card tests were performed by the investigators or reported by the cat owners. Samples provided by the Oy Triniini Company, which included all except one type AB cat, were typed by hemoagglutination and alloantibody assays. (Auer, L. et al., *Anim Blood Groups Biochem Genet.*, 12:287-297 (1981)) Briefly, RBCs were isolated from each cat and were independently incubated with anti-A and anti-B serum. Blood types were confirmed by backtyping with the given cat's own plasma to confirm the presence of alloantibodies. DNA from buccal swab samples was isolated using the QIAamp DNA Mini Kit (Qiagen, Valencia, Calif.). DNA from whole blood and white blood cell buffy coats was extracted using the DNeasy Tissue Kit (Qiagen).

CMAH Gene Analysis

The CMAH cDNA sequence of the domestic dog (ENSEMBL transcript ID ENSCAFT00000016708) was obtained from the ENSEMBL public database (www.ensembl.orgindex.html). The sequence of 13 dog CMAH exons were queried against the cat 2× whole genome sequence database www.ncbi.nlm.nih.govBLASTtracemb.shtml) in the cross-species MegaBLAST application. (Altschul, S. F. et al., *J Mol Biol.*, 215:403-410 (1990)) More than one sequence was identified in the trace archive for each feline exon, thus BLAST2 (Altschul, S. F. et al., *J Mol Biol.*, 215:403-410 (1990)) and MegAlign software (Madison, Wis.) was used to build a feline CMAH gene contig. PCR primers (Table 2) were developed in the intronic regions flanking each identified exon using the software Primer 3.0 frodo.wi.mit.educgi-binprimer3primer3.cgi) and Net primer www.premierbiosoft.comnetprimernetprlaunchnetprlaunch.html). Primers were tested for efficient product amplification on a DNA Engine Gradient Cycler (MJ Research, GMI, Ramsey, Minn.) as previously described. (Lyons, L. A., *Nat Genet.*, 15:47-56 (1998)) Final reaction conditions for each primer pair were as follows: 1 pmol of each forward and reverse primer, 1.25 mM dNTPs, 1.75 mM $MgCl_2$, 1× Buffer and 0.375U of Taq (ABgene, Epsom, UK) polymerase in 30 µl reaction. PCR conditions included an initial denaturation at 95° C. for 2 minutes followed by 35 cycles of 95° C. for 1 minute, 58° C. for 45 sec and 72° C. for 45 sec with a final extension at 72° C. for 10 minutes. Labeled, unlabelled and M13 tailed primers used in the genotyping described below, were synthesized by Operon (Huntsville, Ala.). Each exon was amplified from genomic DNA of a type A random bred cat, Birman, British Shorthair and Devon Rex, and a type B Biinian and British Shorthair. The CMAH genomic sequence was also determined for one Ragdoll and one Sphynx with the AB blood type (Table 1). All PCR products were size separated on 2% agarose gels and the amplicons extracted and purified using the QIAquick® Spin kit (Qiagen). Purified genomic products were directly sequenced using BigDye Terminator V 3.1 (Applied Biosystems, Foster City, Calif., USA), purified through Sephadex 50 columns (Amersham Biosciences, Uppsala, Sweden) and electrophorectically separated on an ABI 3730 DNA Analyzer (Applied Biosystems). Sequences were verified and aligned using the software Sequencer version 4.5 (Gene Codes Corp., Ann Arbor, Mich.).

CMAH mRNA Analyses

Total RNA was extracted from whole blood samples from a cat of each blood type, including a type A Oriental Shorthair, a type B Persian, a type AB Siamese and an obligate carrier of type B (type Ab) that was a hybrid between a Persian and an Oriental Shorthair) (Table 1). RNA was extracted using the Versagene™ RNA Purification Kit (Gentra System, Minneapolis, Minn.) or the PAXgene™ Blood RNA System (Qiagen). Three pools of cDNA template were synthesized by reverse transcription of 1 µg of mRNA with random primers, a gene specific primer, CMAH_GSP__5′ 5′-GAGGTACGT-GATCTGCACTT-3′ (SEQ ID NO:62), and oligo dT primers using SuperScript III (Invitrogen, Carlsbad Calif.). PCR amplification of CMAH from the random primer pool of cDNA was performed using nested primers listed in Table 2. To obtain the 5′ and 3′ portions of the gene, RNA ligase-mediated rapid amplification of 5′ and 3′ cDNA ends (RLM-RACE) were performed using the GeneRacer™ Kit (Invitrogen). The RACE primers were also presented in Table 2. The 5′ RACE used the cDNA pool generated by the CMAH specific primer listed above and the 3′ RACE used the cDNA pool generated from the oligo dT primers. The PCR conditions included an initial denaturation for 2 min, 5 cycles at 95° C. for 30 sec and 72° C. for 1 min, 5 cycles at 95° C. for 30 sec and 70° C. for 1 min, 27 cycles at 95° C. for 30 sec, 68° C. for 30 sec and 72° C. for 1 min, followed by a 10 min extension at 72° C. All PCR products were directly sequenced as previously described except that the 5′RACE-PCR products that were cloned using the TOPO TA Cloning Kit for Sequencing (Invitrogen) prior to sequencing. Seven-twenty-four 5′ RACE cDNA clones from each of the four cats were selected and sequenced.

Mutation Genotyping

Six SNPs identified by genomic sequence analyses (Table 1) were screened in 213 additional cats by pyrosequencing using an M13 biotinylated primer (5′ AGCGCATAA-CAATTTCACAGG-3′; SEQ ID NO:63) (Table 2). The two 5′UTR SNPs were amplified in a single PCR multiplex reaction and the four additional coding region SNPs were detected in separate pyrosequencing amplification reactions. Pyrosequencing reactions were performed on a PSQ 96MA (Biotage, Uppsala, Sweden). Amplification conditions for the pyrosequencing reactions were as follows: 2 min denaturation at 95° C. followed by 45 cycles of a 45 sec denaturation at 95° C., annealing for 30 sec at 62° C. and an extension at 72° C. for 30 sec. The reactions were completed with a 10 min extension at 72° C. The 5′ UTR 18 bp indel was genotyped as a size variant by PCR with a FAM fluorescently labeled forward primer (Table 2) in all 213 cats and electrophorectically separated on an ABI 3730 DNA Analyzer (Applied Biosystems).

Results

Genomic Analyses

Figure 3:
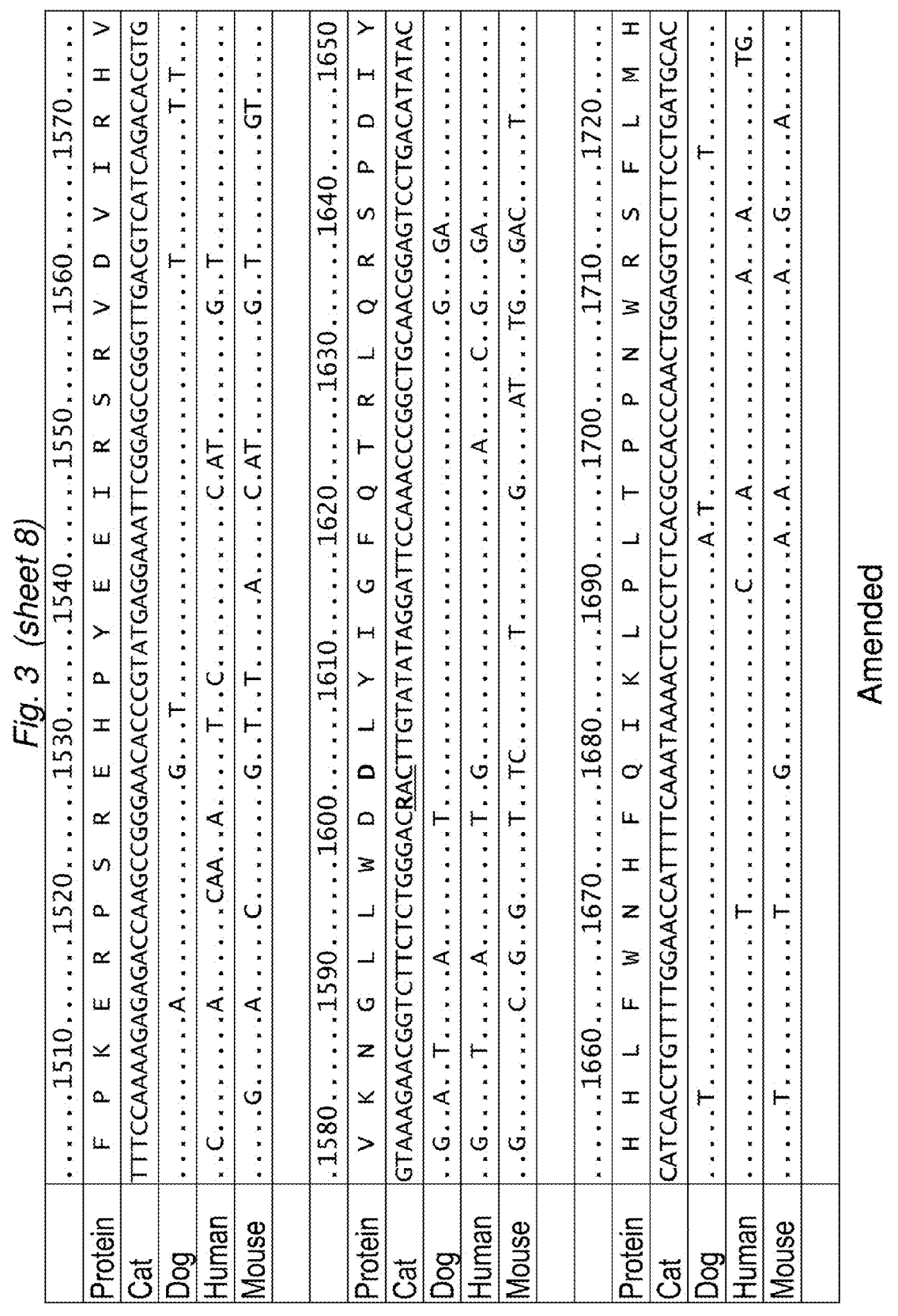

The 2× trace sequence of the cat and the CMAH sequence from the domestic dog were sufficient to identify twelve of the putative 14 exons of feline CMAH. Cat CMAH exons 4 and 10 could not be amplified from genomic DNA since the feline sequences were absent from the trace archives. The sequences of exons 4 and 10 were subsequently analyzed from cDNA comparisons. Sequence analyses of 11 of the 12 exons were obtained from genomic DNA of eight cats, representing five pure and one random breeds and all three blood types. These sequences revealed 10 DNA variants between the type A and B cats, including one silent (C1461T) and 3 missense mutations in the coding regions (FIG. 3). The missense mutations included G139A (V47M), T265A (Y89N), and G1600A (D534N). The three missense coding region SNPs and the silent G1266A in exon 11 were consistent with the blood types in the eight sequenced cats and were subsequently genotyped in 213 additional cats (Table 1), which included the cats comprising the two purebred pedigrees (FIG. 2a, b). CMAH sequences that are different from the published trace sequence were submitted to GenBank. GenBank accessions represent the sequences of the identified DNA variants consistent with type B cats, including sequences for exon 2 (Bankit No. 859860), exon 12 (Bankit No. 859864) and exon 13 (Bankit No. 859868). Other submitted GenBank accession numbers include: Type A cat 5'UTR (Bankit No. 854853); Type B cat UTR (Bankit No. 854855); Type B cat exon 13 (Bankit No. 859868); Type B cat intron 1 (Bankit No. 854859); Type A cat mRNA (Bankit No. 854861); Type B cat mRNA GenBank (Bankit No. 859872). Six additional silent mutations were identified in the coding regions but these variants were not present in all the cats with the same blood type or were unique to an individual cat (FIG. 3).

Only one coding region SNP, the silent G1266A mutation in exon 11, was inconsistent with the blood types in the expanded sample pool. Approximately 20 individuals had genotypes that were discordant with the blood types (data not shown). The other three missense SNPs, G139A (V47M), T265A (Y89N), and G1600A (D534N), formed haplotypes that were consistent with the blood types. All type B cats were homozygous for the identified variants. All type A cats that were obligate carriers of type B (Type Ab) were heterozygous, suggesting 2 haplotypes. No cats that were type A were homozygous for the type B haplotype. In addition, these haplotypes segregated concordantly with the blood types in the two breed pedigrees (FIG. 2a, b).

Approximately 550 bp of genomic DNA sequence upstream of the start codon in exon 1, including the exon 1 5' UTR, was analyzed in six type A cats, three type B cats and two type AB cats (Type A Bankit No. 854853, Type B Bankit No. 854855). Five additional SNPs and an indel were identified, including G-108A, G-217A, C-371T, A-468G and G-539A (FIG. 4). Each generated sequence included an 18 bp insertion-deletion at position −53 in the 5'UTR. The 18 bp insertion was absent in the type A homozygous cats but present in the type B cat. Two SNPs, G-217A and C-371T, and the indel were consistent with the blood types and were genotyped in the additional cats. These three 5'UTR variants, as well as the three coding region SNPs, formed consistent haplotypes with the blood types in all tested cats.

mRNA Analyses

The complete CMAH cDNA was sequenced from 3 cats, including a type A Oriental Shorthair (Bankit No. 854861), a type B Persian (Bankit No. 859872), and a type AB Siamese. The cDNA sequence and protein translation is presented in FIG. 3. The resultant cDNA sequences were compared with published sequence from several species, including mouse (D21826), human (AF074480), dog (from Ensemble ENSCAFT00000016708) and cat (AANG01215984). The cat CMAH had 578 amino acids and coded 14 exons, producing a 1734 nucleotide transcript (FIG. 3). Only the last 6 bps of exon 1 were translated, presenting the putative start codon, methionine, and a glycine, prior to the splice to the fully translated exon 2, which began with a serine. The first 72 amino acids in terminal exon 14 were translated, the polyadenylation signal is 373 bp downstream of the stop codon. Cat CMAH exhibited 91.7% nucleotide sequence identity to the predicted sequence of the dog, 83.7% with the mouse, and 84.5% with human. At the protein level, cat CMAH was 92.9% identical to the dog, 89.6% identical to the mouse and 87.7% identical to human.

The cDNA analyses allowed the comparisons of feline CMAH exons 4 and 10, which were not amplified from genomic DNA. One additional missense SNP present in the type B cat, A324C, caused an E108D amino acid change in exon 4 (FIG. 3). However, flanking sequences were insufficient to genotype this SNP in additional cats. More than two species of cDNA sequence were identified for each cat. The cloned 5' UTR sequences ranged from approximately 16-121 bp in length upstream of the putative start codon (FIG. 5). Approximately 50% of the cDNA sequences in exon 1 were missing in type B cats. Intron 1 sequence appeared prior to exon 2 sequence in these cloned sequences, with an AGT 16 bp upstream of the splice site for the initial serine codon for exon 2 (FIGS. 4 & 5). This AGT caused a shift in the reading frame of the protein. This variant form of cDNA was also identified in the type Ab and type AB cat. Cats homozygous for the haplotype of variants that were concordant with type A cats did not have cDNA sequence variants lacking exon 1.

An 18 bp insertion was present approximately 53 bp upstream of the putative start codon in several clones that retained exon 1. This insertion was genotyped in genomic DNA as described above and was identified in type B, type Ab and type AB cats. Some cDNA sequences extended to over 117 bp upstream of the putative start site in exon 1 in both type A and type B cats. An AGT was located at −102 bp, which was in frame with the exon 1 AGT. The 18 bp insertion in the type B cats caused a stop codon at −54 bp, thus, if this −102 AGT were active, the CMAH protein would be disrupted in the type B cats.

Blood Type AB Cats

Approximately 8,650 cat samples have been blood typed by hemoagglutination assay at the collaborating service laboratory (data not shown). Approximately 133 cats were type AB, suggesting a frequency of approximately 1.5%. However, a majority of the type AB cats represented the Ragdoll breed (N=104) and European shorthairs (N=18). Three of six cDNA sequences from the type AB cat were missing exon 1 and had intron 1 sequence upstream of exon 2. This type AB cat was heterozygous for the exon 1 insertion and the other SNPs that were concordant for the blood types. This suggested that one allele was similar to a type B allele. Blood type AB cats were never homozygous for the haplotype of the B blood group, thus never matching the genotype of a type B cat. Two type AB cats of the Sphynx breed were homozygous for the 18 bp insertion but heterozygous for the four other mutations in the haplotypes (Table 1).

TABLE 1

CMAH DNA variants genotyped in domestic cats.

| Breed | Blood Type[1] | No. | 5' UTR G-217A | 5' UTR C-371T | 5' UTR Δ-53 | E2 G139A | E3 T265A | E13 G1591A |
|---|---|---|---|---|---|---|---|---|
| Trace archive | | | a | a | N[2] | G | T | G |
| Birman[3] | A | 18 | AA | CC | NN | GG | TT | GG |
| British SH[3] | A | 5 | AA | CC | NN | GG | TT | GG |
| Devon Rex[3] | A | 5 | AA | CC | NN | GG | TT | GG |
| Domestic SH[3] | A | 1 | AA | CC | NN | GG | TT | GG |
| Exotic SH | A | 3 | AA | CC | NN | GG | TT | GG |
| Oriental SH[4] | A | 1 | AA | CC | NN | GG | TT | GG |
| Scottish Fold | A | 2 | AA | CC | NN | GG | TT | GG |
| | | | | | | | | |
| Birman | A | 19 | AG | CT | NP | GA | TA | GA |
| British SH | A | 14 | AG | CT | NP | GA | TA | GA |
| Devon Rex | A | 18 | AG | CT | NP | GA | TA | GA |
| Domestic SH | A | 1 | AG | CT | NP | GA | TA | GA |
| Exotic SH | A | 1 | AG | CT | NP | GA | TA | GA |
| Hybrid[4] | Ab | 12 | AG | CT | NP | GA | TA | GA |
| Scottish Fold | A | 5 | AG | CT | NP | GA | TA | GA |
| Siberian | A | 2 | AG | CT | NP | GA | TA | GA |
| | | | | | | | | |
| Birman[3] | B | 22 | GG | TT | PP | AA | AA | AA |
| British SH[3] | B | 30 | GG | TT | PP | AA | AA | AA |
| Devon Rex[3] | B | 25 | GG | TT | PP | AA | AA | AA |
| Persian[4] | B | 1 | GG | TT | PP | AA | AA | AA |
| Scottish Fold | B | 1 | GG | TT | PP | AA | AA | AA |
| | | | | | | | | |
| Bengal | AB | 1 | AA | CC | NN | GG | TT | GG |
| Devon Rex | AB | 1 | AA | CC | NN | GG | TT | GG |
| Egyptian Mau | AB | 1 | AA | CC | NN | GG | TT | GG |
| European | AB | 4 | AA | CC | NN | GG | TT | GG |
| Ragdoll | AB | 8 | AA | CC | NN | GG | TT | GG |
| Siamese[4] | AB | 1 | AA | CC | NN | GG | TT | GG |
| Siberian | AB | 1 | AA | CC | NN | GG | TT | GG |
| British SH | AB | 3 | AG | CT | NP | GA | TA | GA |
| Cornish Rex | AB | 2 | AG | CT | NP | GA | TA | GA |
| Devon Rex | AB | 7 | AG | CT | NP | GA | TA | GA |
| European | AB | 1 | AG | CT | NP | GA | TA | GA |
| Maine Coon | AB | 1 | AG | CT | NP | GA | TA | GA |
| Manx | AB | 1 | AG | CT | NP | GA | TA | GA |
| Ragdoll[3] | AB | 1 | AG | CT | NP | GA | TA | GA |
| Sphynx[3] | AB | 2 | AG | CT | NN | GA | TA | GA |
| Totals: 18 | | 221 | | | | | | |

1. Blood typing was determined as described in the Methods.
2. The 18 bp indel is represented by N for not present and P for present.
3. The genomic sequence of each CMAH exon, except exons 4 and 10 was determined for one cat of each of the indicated breeds.
4. The cDNA sequence was determined for one cat of each of the indicated breeds.

TABLE 2

Sequences and primers for CMAH analysis in the cat.

| CMAH Region | Forward Primer 5'-3' (SEQ ID NO:) | Reverse Primer 5'-3' (SEQ ID NO:) | size bp |
|---|---|---|---|
| 5'UTR-e1 | TTCCTTTGCTGCTGG AGTG (4) | CAACACTGAGCAAGC AGAGC (6) | 653 |
| Exon 2 | CAACACTGAGCAAGC AGAGC (6) | GGTTTCCTCTCTCTC AGGGG (60) | 589 |
| Exon 3 | CTCTTAGGACATGGA CTGAACG (8) | CTTTGGTAAGACGGG TGAGAG (61) | 458 |
| Exon 5 | GTGTCTGTCGCATCA CCTCT (10) | GGATGAGAAGAAGCG GACTC (64) | 668 |
| Exon 6 | GGCAGAGAGCAGGAA GACAC (12) | TTTTCCCCCATTTAC CAATG (65) | 571 |
| Exon 7 | TAGCCGATTTTGTC TGTGC (14) | TCAACACTTCCATAC ATCACCC (66) | 669 |
| Exon 8 | GATCCCATCATGCTT CCTCT (16) | GAAACCAGACTTGCA AAGCA (67) | 630 |
| Exon 9 | GTGTCTTTGGCTGGT TTGGT (18) | GACTTTTAGCCACGC CATTC (68) | 642 |
| Exon 11 | GCCACACAGCTCCCA TAGAC (20) | TGTTGTTGTGGGTTT TGTGG (69) | 624 |
| Exon 12 | CATGGTGTTTGCTGT CTCAT (22) | CCTCTACATGCTTAC TGCCC (70) | 647 |

TABLE 2-continued

Sequences and primers for CMAH analysis in the cat.

| CMAH Region | Forward Primer 5'-3' (SEQ ID NO:) | Reverse Primer 5'-3' (SEQ ID NO:) | size bp |
|---|---|---|---|
| Exon 13 | GACATGAGGGGTCGG TACG (24) | CTCAACTCCAGCGTG CATTT (71) | 579 |
| Exon 14 | TTCACTGTTGGATGA TGTGG (26) | GACTTTCAGGGGAGT GAGAAG (72) | 700 |
| ¹cDNAe2-6 | GACGACGGAGGTCTT GTTGT (28) | TTACCCCACACTGAA GGAGC (73) | 608 |
| ¹cDNAe5-11 | CAAGAGGATGGTGTT TGACC (30) | GCATCATAGAGCCTC CAGAG (74) | 817 |
| ¹cDNAe9-14 | GGAATCTCACCCATC AGACA (32) | CTGTGGGTAGAGCAG ACCTG (75) | 656 |
| 5' RACE | | AAATACGTCAATCCC CCAGGCAGCTTCT (76) | ~500 |
| 3' RACE | AACTCCCTCTCACGC CACCCAACTG (35) | | 440 |
| A-53 | TCCTCCGTCTCATAC TTTGTGG (36) | CATTTCCAGGGGAGC AGC (77) | 167 |
| UTR SNPs | ²GCCGGGTGTAAGGT TCTC (38) | CACCTGGAGCCCAAT AGG (78) | 247 |
| ³C-371T | | AGCACGTGTAGGCT (79) | |
| ³G-217A | | AAGTGTGCAGGTG (80) | |
| Exon 2 | ²CTGCTGACCTGAAG GAAGGAAT (45) | ACCCGTGAGAAGGCT CAGAA (46) | 187 |
| ³G139A | | GGCGTGCAAGAACG (81) | |
| Exon 3 | TGTCAGATGCACAAA GCACAAC (42) | ²TGCTGTGATCGTTA CTGGCGT (82) | 141 |
| ³T265A | TGTGAGCACCATG AAA (44) | | |
| Exon 10 | CGACTAACTGTCACC TTTGTGTCTT (51) | ²TGAATGCTGCTGTA GGAGAT (83) | 128 |
| ³G1266A | AAGCAAGGGCATC ATA (53) | | |
| Exon 12 | ²ATTCGGAGCCGGGT TGAC (54) | CCTGTAAGTTGGAAA GTGCCTG (84) | 135 |
| ³G1591A | | GTATATAGGATTCCA AACCC (85) | |

1. Nested primers for the cDNA analysis. The position of the primer in the exons are indicated in the primer name.
2. The M13 tail was attached to the indicated end of the indicated primer.
3. Primer for the pyrosequencing reaction of each amplified SNP region.

Discussion

The human ABO blood group, the oldest known blood group system, was discovered over 100 years ago. (Landsteiner, K., *Wochenschrift*, 14:1132-1134 (1901)) Since then, dozens of blood group systems have been recognized by the International Society of Blood Transfusion and 39 are genetically characterized in humans. (Blumenfeld, O. et al., *Human Mutation.*, 23:8-16 (2004); Daniels, G., *Transpl Immunol.*, 14:143-153 (2005)) Blood group systems of equal, or even greater complexity than in humans have been elucidated in cattle and horses. (Bell, K. *Red blood cells of domestic mammals*, In: Agar N S, Board P G, eds., Elsevier Science Publishers, 133-164 (1983); Stormont, C. J., *J Am Vet Med Assoc.*, 181:1120-1124 (1982)) Indeed, the high degree of polymorphism of some blood groups in humans and some agricultural species have allowed blood groups to be used for identification and parentage testing. The registries of several agricultural species have used blood typing for over 40 years to document pedigrees. In addition to pedigree testing, blood typing has been of crucial importance in preventing transfusion reactions and neonatal isoerythrolysis in a variety of species.

The cat AB blood type is both unique and typical of other blood groups. It is unique because it appears to be the sole major blood group system. It is typical in that cats with one blood type naturally produce alloantibodies to the opposing blood type. (Giger, U. et al., *J Reprod Fertil Suppl.*, 51:313-316 (1997); Casal, M. L. et al., *Am J Vet Res.*, 57:1653-1658 (1996)) Therefore, like other blood group systems, such as ABO of humans, the AB system of cats is important in transfusion reactions and neonatal isoerythrolysis. (Giger, U. et al., *J Reprod Fertil Suppl.*, 51:313-316 (1997); Casal, M. L. et al., *Am J Vet Res.*, 57:1653-1658 (1996)) The cat AB blood group is atypical because it has not been useful for parentage and identification testing. It has only two common alleles and the vast majority of cats have the same blood type A.

The cat is unique because its major blood group system is coded by a gene not listed among the 39 blood type genes identified in humans. Cytidine monophospho-N-acetyl-neuraminic acid hydroxylase (CMAH), which is associated with the production of the sialic acids on cat red cells (Andrews, G. A. et al., *Blood*, 79:2485-2491 (1992)), is non-functional in humans and chickens. (Irie, A. et al., *J Biol Chem.*, 273:15866-15871 (1998); Chou, H. H. et al., *Proc Natl Acad Sci USA.*, 95:11751-11756 (1998)) However, CMAH has been highly conserved and is active in species as primitive as echinoderms. (Martensen, I. et al, *Eur J Biochem.*, 268:5157-5166 (2001)) The sialic acids on the oligosaccharide chains of cell surface gylcoconjugates were found to be important for mammalian embryogenesis, the immune response, inflammation, tumor cell metastasis and other cellular interactions.

The present invention demonstrates that the genomic structure of cat CMAH is similar to the homologous gene in other species. Cat CMAH is 578 amino acids coded by 14 exons, producing a 1734 nucleotide transcript. Comparison to mouse and rat CMAH suggests that only the last 6 nucleotides of exon 1 and the first 72 in terminal exon 14 were translated. The cat CMAH genomic structure is also similar to the dog, however, dog CMAH has only been deduced by annotation by the Ensembl automatic analysis pipeline from sequence generated by the canine genome sequencing projects.

This invention also demonstrates that the cat AB blood types resulted from mutation(s) in CMAH that prevent the conversion of NeuAc to NeuGc, hence type B to type A. Several mutations, including 2 SNPs upstream of the start, an indel in the exon 1 UTR and three missense mutations in the coding region were concordant with the type A and type B blood types of cats representing 18 breeds from the USA and Europe. The six mutations were homozygous in all type B cats and heterozygous in all type A cats that were obligate carriers for type B. No type A cats were homozygous for these six variants. Thus, any or all of these mutations can be used to genotype cats for their blood group determination, allowing the identification type B carriers.

Further data indicates that the G to A substitution at position 139 in exon 2 is the most likely causative mutation for the Type B blood type and the B allele in the cat. However, the additional mutations disclosed herein are in strong linkage disequilibrium with this causative mutation and all or one of the additional mutations can still be used as a proxy for the causative mutation in most cat breeds.

CMAH may be extended at the amino terminus of the protein in the cat, which would be unique to the cat but clarify the type AB serotype. Although the CMAH protein translation start site was conserved across various species, the cDNA analyses of cat CMAH, particularly the 5' UTR, may present a different protein translation start site for the cat than what has been noted for other species. For both type A and type B cats, cDNA sequence extended approximately 121 bp upstream of the exon 1 start site. Within this sequence, a potential start codon is located at −102 bp upstream of the traditionally start site, which is the next to last codon of exon 1. For the type A cat, the upstream start would add an additional 28 amino acids to the 5' portion of the gene. For the type B cats, which have an 18 bp indel, the translation remains in frame from this putative upstream start, but the indel codes for a stop at position −54, which would terminate the protein prior to the translation of exon 1, disrupting nearly the entire protein. For the type AB cat, the cDNA sequences did not extend to the −102 bp AGT, suggesting that the traditionally regarded CMAH start site may actually initiate translation of the protein, representing this third allele. Since both salicylic acids are present on the red cell antigens in the type AB cats (Griot-Wenk, M. et al., *Anim Genet.*, 24:401-407 (1993)), CMAH must convert some N-acetylneuraminic acid (NeuAc) to N-glycolylneuraminic acid (NeuGc). The produced protein would be missing 28 amino acids at the amino terminus, producing a functional, but less efficient enzyme that would not catalyze all the available NeuAc to NeuGc. Comparative analyses of the −121 bp upstream sequence did not indicate conservation in any other species. The proposed alternative upstream start site would be unique for the cat, but readily explains the three blood group alleles for the cat.

Other identified variations in the genomic sequence upstream of the traditional protein translation start site also influences CMAH transcription in the cat. Approximately 50% of the cDNA sequences of type B cats were missing exon 1—and had part of the introns 1 sequence spliced directly to exon 2. The same cDNA sequence variants were noted in type Ab and type AB cats. The variants in the 5' upstream region may interact with transcription initiation in the mRNA, leading to the intron 1 sequence that is upstream to exon 2 for approximately 50% of the cDNA species in the type B. Notably, the C-369T mutation disrupts a GATA transcription factor site in the type B cat. An additional GATA site is located in introns 1 and is present in both the type A and type B cats. (Schug, J. et al., Transcription Element Search Software on the WWW, Technical Report CBIL-TR-1997-1001-v0.0, Computational Biology and Informatics Laboratory, School of Medicine, University of Pennsylvania (1997)) When the introns 1 sequence is present in the cDNA, an AGT is present upstream of the splice to exon 2. If active, this AGT would significantly disrupt the reading frame of the protein. If this intronic AGT is not the protein translation initiation, then the adenine SNP in exon 2 presents an in frame, however weak, methionine start, which would truncate 46 amino acids from the 5' portion of the protein. Hence, the indel, the splicing error or an active GI 39A AGT start all lead to a significantly altered enzyme that could prevent the conversion of N-acetylneuraminic acid (NeuAc) to N-glycolylneuraminic acid (NeuGc) in the type B cat. Regardless of the intron 1 or exon 2 alternative start codons, the exon 1 AGT remains the strongest start site, having a highly conserved surrounding Kozak sequence, including a G residue following the AGT and an A residue three nucleotides upstream (Kozak, 1996).

With respect to the AB blood type, although the cDNA studies suggest a mechanism for the serotype, the mutation that truncates the 5' portion of the cDNA in the type AB was not apparent from these studies. Causative mutations for the type AB allele could be present in regulatory regions of the gene, either upstream of the 550 bp region analyzed in this study or within introns. Within the analyzed regions, the type AB cat could not be differentiated by genomic sequence from a type A cat. However, no type AB cats (N=26) were homozygous for the type B haplotype of mutations. In the USA, type AB cats were noted in breeds with high frequencies of type B cats. (Giger, U. et al., *Feline Practice*, 19:21-27 (1991)) In this study, a type AB cat was identified in the Maine Coon and Siamese breeds, both of these breeds having a very low frequency of type B cats. (Giger, U. et al., *J Hered.*, 82:15-20 (1991)) Type AB in cats has been shown to be slightly higher in the Sacramento, Calif. area (Giger, U. et al., *J Hered.*, 82:15-20 (1991); Giger, U. et al., *Feline Practice*, 19:21-27 (1991)), the regional location for the type AB Siamese cat used in the cDNA analyses. The reported association between type AB and type B cats in the USA may be sampling error due to the low frequency of type AB cats. The high incidence of type B cats from Turkey, with no type AB cats supports a non-linkage between type B and AB cats. (Arikan, S. et al., *J Vet Med A Physiol Pathol Clin Med.*, 50:303-306 (2003)) The present invention indicates that AB is allelic to A and B in cats, and that the yet unidentified mutation resides on a type A allelic background.

Blood typing in cats is currently accomplished by various tube or slide-based hemoagglutination assays in large veterinary practices and commercial laboratories. Smaller laboratories and private veterinary practices often use the commercially available RapidVet Blood Type cards. Tests for type A cats use monoclonal antibodies recognizing the A antigen (NeuGc) and cause erythrocyte agglutination. Type B cat red cells are preferentially agglutinated by lectin from *Triticum vulgaris*. All the type AB cats used in this study were confirmed by alloantibody testing. Genetic testing has several obvious advantages for determining feline blood types. The cost of obtaining a buccal swab and submitting it for genetic typing would be lower than for the cost of a veterinary visit and test. More importantly, cat breeders can more accurately predict the exact genotype of their cats and use this information to prevent matings that might lead to neonatal isoerythrolysis. Furthermore, current non-genetic tests do not determine the existence of heterozygotes as is provided by the present invention.

It is understood that the examples and embodiments described herein are for illustrative purposes only and that various modifications or changes in light thereof will be suggested to persons skilled in the art and are to be included within the spirit and purview of this application and scope of the appended claims. All publications, accession numbers, patents, and patent applications cited herein are hereby incorporated by reference in their entirety for all purposes.

---

INFORMAL SEQUENCE LISTING

CMAH coding sequence

SEQ ID NO: 1

```
ATGGGCAGCATTGAACAGACGACGGAGGTCTTGTTGTGTYTGTCACCTGG
AGAAGCTGCTGACCTGAAGGAAGGAATCAATTTCTTGAGAAACAAGAAGR
CCGGCAAAGATTTCATTCTGTACAAGAGCAAGAATCGCRTGAGGGCGTGC
AAGAACGTGTGCAAGCATCAAGGAGGCCTGTTCATAAAAGACATCGAAGA
TTTAGACGGAAGGTCTGTCAGATGCACAAAGCACAACTGGAGGTTGGATG
```

INFORMAL SEQUENCE LISTING

TGAGCACCATGAAAWACGTCAATCCCCCAGGCAGCTTCTGTCAAGACGAA
CTAGTTGTTGAAATGGATGAAGAMAATGGACTTTTACTTCTAGAACTGCAG
TCCTCCCAATCCCTGGGATTCAGAACCCAGATCTCCTGAACATTTGGCTT
TTGGAGAAGTGCAGATCACGTACCTCACCCACGCCTGCATGGACCTCAAG
CTGGGAGACAAGAGGATGGTGTTTGACCCCTGGTTAACGGGTCCTGCGTT
CGCCCGAGGCTGGTGGCTGCTGCACGAGCCTCCGTCTGATTGGCTGGAGA
GGCTGTGCCAGGCAGACCTGATTTACATCAGTCACATGCACTCAGACCAC
CTGAGTTACCCCACACTGAAGGAGCTGGCTGGGAGAAGACCGGATATTCC
CATTTATGTTGGAAACACGGAAAGACCTGTATTTTGGAATCTGAATCAGA
GCGGTGTCCAGTTGACCAATATCAATATAGTGCCATTCGGAATATGCCAG
CAGGTAGACAAAAATCTTCGATTCATGATCTTGATGGATGGCGTTCATCC
TGAGATGGACACTTGCATTATTGTGGAGTATAAAGGTCATAAGATACTTA
ATACAGTGGACTGCACCAGACCCAATGGGGAAGGTTGCCTGAGAAGGTT
GCTCTAATGATGAGTGATTTTGCTGGAGGAGCATCAGGCTTTCCAATGAC
TTTCAGTGGTGGAAAATTTACCGAGGAATGGAAAGCCCA
CAGAGAGGAAGAAGCTCTTGAACTACAAGGCCCGGCTGGTGAAGGACCTA
CAACCCCGAATTTATTGCCCCTTTGCTGGGTATTTTGTGGAATCTCACCC
ATCAGACAAGTATATTAAGGAAACAAACATCAAAAATGACCCAAATGAAC
TCAATAATCTTATCAAGAAAAACTCTGATGTGGTAACGTGGACCCCACGG
CCTGGAGCCACTCTTGATCTGAGTCGGATGCTAAAGGACCCGACAGACAG
CAAGGGCATCATAGARCCTCCAGAGGGGACCAAGATCTACAAGGATTCCT
GGGACTTTGAACCCTATTTGAACATCTTGAATGCTGCTGTAGGAGATGAG
ATATTTCTCACTCATCCTGGATAAAAGAATACTTCACYTGGGCKGGATT
TAAGGATTACAACCTGGTGGTCAGGATGATTGAAACAGATGAGGACTTCA
GCCCTTTTCCYGGAGGATATGACTATTTGGTTGACTTTCTAGACTTATCC
TTTCAAAAGAGAGACCAAGCCGGGAACACCCGTATGAGGAAATTCGGAG
CCGGGTTGACGTCATCAGACACGTGGTAAAGAACGGTCTTCTCTGGGACR
ACTTGTATATAGGATTCCAAACCCGGCTGCAACGGAGTCCTGACATATAC
CATCACCTGTTTTGGAACCATTTTCAAATAAAACTCCCTCTCACGCCACC
CAACTGGAGGTCCTTCCTGATGCACTGTGGGTAG

CMAH genomic sequence including 5 UTR to exon 2

SEQ ID NO: 2

ACGGAGGTTCTGTGGGAAAGTTAACTCACGAAGTAGCTAGCTGGTAGAGA
TACACCGCGTGACAGGCCGTGTGCTCAGCGACAGGGAGGGAGAATGTTTG
GAAAAGCGTCCCTATGTAAATAAACGGGGCACCGTGCCGGGTGTAAGGTT
CTCATGTTCTACAGAATGGTAGTGCGTATCAGCACGTGTAGGCTTGTCCC
GGGGGTGGCTTTGGAGGCTTGACCCAGGCTGGGGTAGGACGACTGGGTTC
TATTTGAACCTGGAGGGTGGTAAACATGACTAGTGGTGAAAGTTGAACCG
TGCTTGTGAGCAAAAGGATCAGATCTAAACGCAgAAGTGTGCAGGTGGGA
GCGGGCAGGGTGGGCACCTGGAGCCCAATAGGATCCTGCGTCTGAAGCAA
CACAGCAGAGGAAGTGGTGCAACGGAATCAGTAGTGAACCGCGTGCATAT
GCATCCTCCGTCTCATACTTTGTGGGAGCAAACGAGCAACCACCGTCCTT
TCAGAATTCCCAGGGAGAGGCAGCTGCGGACCATGGGCaggcaagtgaca
ggggcattgggtctggaggaacccgagaccaacactgagcaagcagagcg
tgcatttccaggggagcagccaagcctgggtcctgcgagggaggggcttg
agcctatcgcggtggaaagaggctttgagccgccagtttcaaaagatgct
ctcctaagtcttaacgttattaaccttcctccccaaatgtctgcctttcc
gtAGCATTGAA CMAH protein sequence

SEQ ID NO: 3

MGSIEQTTEVLLCLSPGEAADLKEGINFLRNKKTGKDFILYKSKNRVRAC
KNVCKHQGGLFIKDIEDLDGRSVRCTKHNWRLDVSTMKYVNPPGSFCQDE
LVVEMDEENGLLLLELNPPNPWDSEPRSPEHLAFGEVQITYLTHACMDLK
LGDKRMVFDPWLTGPAFARGWWLLHEPPSDWLERLCQADLITISHMHSDH
LSYPTLKELAGRRPDIPIYVGNTERPVFWNLQSGVQLTNINIVPFGIWQ
QVDKNLRFMILMDGVHPEMDTCIIVEYKGHKILNTVDCTRPNGGRLPEKV
ALMMSDFAGGASGFPMTFSGGKFTEEWKAQFIKAERKKLLNYKARLVKDL
QPRIYCPFAGYFVESHPSDKYIKETNIKNDPNELNNLIKKNSDVVTWTPR
PGATLDLSRMLKDPTDSKGIIEPEGTKIYKDSWDFEPYLNILNAAVGDEI
FLHSSWIKEYFTWAGFKDYNLVVRMIETDEDFSPFPGGYDYLVDFLDLSF
PKERPSREHPYEEIRSRVDVIRHVVKNGLLWDDLYIGFQTRLQRSPDIYH
HLFWNHFQIKLPLTPPNWRSFLMHCG

Forward primer for 5'UTR - exon 1

SEQ ID NO: 4

TTCCTTTGCTGCTGGAGTG

Reverse primer for 5'UTR - exon 1

SEQ ID NO: 5

GCTCTGCTTGCTCAGTGTTG

Forward primer for Exon 2

SEQ ID NO: 6

CAACACTGAGCAAGCAGAGC

Reverse primer for Exon 2

SEQ ID NO: 7

CCCCTGAGAGAGAGGAAACC

Forward primer for Exon 3

SEQ ID NO: 8

CTCTTAGGACATGGACTGAACG

Reverse primer for Exon 3

SEQ ID NO: 9

CTCTCACCCGTCTTACCAAAG

Forward primer for Exon 5

SEQ ID NO: 10

GTGTCTGTCGCATCACCTCT

Reverse primer for Exon 5

SEQ ID NO: 11

GAGTCCGCTTCTTCTCATCC

Forward primer for Exon 6

SEQ ID NO: 12

GGCAGAGAGCAGGAAGACAC

Reverse primer for Exon 6

SEQ ID NO: 13

CATTGGTAAATGGGGGAAAA

Forward primer for Exon 7

SEQ ID NO: 14

TAGCCGATTTTTGTCTGTGC

Reverse primer for Exon 7

SEQ ID NO: 15

GGGTGATGTATGGAAGTGTTGA

Forward primer for Exon 8

SEQ ID NO: 16

GATCCCATCATGCTTCCTCT

Reverse primer for Exon 8

SEQ ID NO: 17

TGCTTTGCAAGTCTGGTTTC

Forward primer for Exon 9

SEQ ID NO: 18

GTGTCTTTGGCTGGTTTGGT

Reverse primer for Exon 9

SEQ ID NO: 19

GAATGGCGTGGCTAAAAGTC

Forward primer for Exon 11

SEQ ID NO: 20

GCCACACAGCTCCCATAGAC

| INFORMAL SEQUENCE LISTING | |
|---|---|
| Reverse primer for Exon 11 | |
| CCACAAAACCCACAACAACA | SEQ ID NO: 21 |
| Forward primer for Exon 12 | |
| CATGGTGTTTGCTGTCTCAT | SEQ ID NO: 22 |
| Reverse primer for Exon 12 | |
| GGGCAGTAAGCATGTAGAGG | SEQ ID NO: 23 |
| Forward primer for Exon 13 | |
| GACATGAGGGGTCGGTACG | SEQ ID NO: 24 |
| Reverse primer for Exon 13 | |
| AAATGCACGCTGGAGTTGAG | SEQ ID NO: 25 |
| Forward primer for Exon 14 | |
| TTCACTGTTGGATGATGTGG | SEQ ID NO: 26 |
| Reverse primer for Exon 14 | |
| CTTCTCACTCCCCTGAAAGTC | SEQ ID NO: 27 |
| Forward primer for cDNA exons 2-6 | |
| GACGACGGAGGTCTTGTTGT | SEQ ID NO: 28 |
| Reverse primer for cDNA exons 2-6 | |
| GCTCCTTCAGTGTGGGGTAA | SEQ ID NO: 29 |
| Forward primer for cDNA exons 5-11 | |
| CAAGAGGATGGTGTTTGACC | SEQ ID NO: 30 |
| Reverse primer for cDNA exons 5-11 | |
| CTCTGGAGGCTCTATGATGC | SEQ ID NO: 31 |
| Forward primer for cDNA exons 9-14 | |
| GGAATCTCACCCATCAGACA | SEQ ID NO: 32 |
| Reverse primer for cDNA exons 9-14 | |
| CAGGTCTGCTCTACCCACAG | SEQ ID NO: 33 |
| 5' RACE primer | |
| AGAAGCTGCCTGGGGGATTGACGTATTT | SEQ ID NO: 34 |
| 3' RACE primer | |
| AACTCCCTCTCACGCCACCCAACTG | SEQ ID NO: 35 |

| INFORMAL SEQUENCE LISTING | |
|---|---|
| Forward primer for Δ-53 | |
| TCCTCCGTCTCATACTTTGTGG | SEQ ID NO: 36 |
| Reverse primer for Δ-53 | |
| GCTGCTCCCCTGGAAATG | SEQ ID NO: 37 |
| Forward primer for UTR SNPs | |
| GCCGGGTGTAAGGTTCTC | SEQ ID NO: 38 |
| Reverse primer for UTR SNPs | |
| CCTATTGGGCTCCAGGTG | SEQ ID NO: 39 |
| Pyrosequencing primer for C-371T | |
| AGCCTACACGTGCT | SEQ ID NO: 40 |
| Pyrosequencing primer for G-217A | |
| CACCTGCACACTT | SEQ ID NO: 41 |
| Forward primer for Exon 2 | |
| TGTCAGATGCACAAAGCACAAC | SEQ ID NO: 42 |
| Reverse primer for Exon 2 | |
| ACGCCAGTAACGATCACAGC | SEQ ID NO: 43 |
| Pyrosequencing primer for G139A | |
| TGTGAGCACCATGAAA | SEQ ID NO: 44 |
| Forward primer for Exon 2 | |
| CTGCTGACCTGAAGGAAGGAAT | SEQ ID NO: 45 |
| Reverse primer for Exon 2 | |
| ACCCGTGAGAAGGCTCAGAA | SEQ ID NO: 46 |
| Pyrosequencing primer for T265A | |
| GGCGTGCAAGAACG | SEQ ID NO: 47 |
| Forward primer for Exon 4 | |
| TGTCAGATGCACAAAGCACAAC | SEQ ID NO: 48 |
| Forward primer for Exon 4 | |
| ACGCCAGTAACGATCACAGC | SEQ ID NO: 49 |
| Pyrosequencing primer for A324C | |
| TGTGAGCACCATGAAA | SEQ ID NO: 50 |

| INFORMAL SEQUENCE LISTING | |
|---|---|
| Forward primer for Exon 10 | SEQ ID NO: 51 |
| CGACTAACTGTCACCTTTGTGTCTT | |
| Reverse primer for Exon 10 | SEQ ID NO: 52 |
| TCATCTCCTACAGCAGCATTCA | |
| Pyrosequencing primer for G1266A | SEQ ID NO: 53 |
| AAGCAAGGGCATCATA | |
| Forward primer for Exon 12 | SEQ ID NO: 54 |
| ATTCGGAGCCGGGTTGAC | |
| Reverse primer for Exon 12 | SEQ ID NO: 55 |
| CAGGCACTTTCCAACTTACAGG | |

| INFORMAL SEQUENCE LISTING | |
|---|---|
| Pyrosequencing primer for G1591A | SEQ ID NO: 56 |
| GGGTTTGGAATCCTATATAC | |
| 18 bp insert at -53 of 5' UTR | SEQ ID NO: 57 |
| AACGAGCAACCGAAGCTG | |
| | SEQ ID NO: 58 |
| AGTAGTGAACCGCGTGCAT<u>ATG</u>CATCCTCCGTCTCATACTTTGTGGGAGC AAACGAGCAACCACCGTCCTTTCAGAATTCCCAGGGAGAGGCAGCTGCGG ACC<u>ATG</u>GGCAGCATT | |
| Additional cDNA sequence due to apparent splicing error | SEQ ID NO: 59 |
| cagtttcaaaagatgctctcctaagtcttaacgttattaacctttcctcc cccaaatgtctgcctttccgtAGCATT | |

What is claimed is:

1. A method of distinguishing blood type in a cat, comprising the steps of providing a biological sample and detecting the presence or absence of a mutation in both alleles of the feline CMAH gene,
   wherein the mutation is a G to A substitution at position 139 of the feline CMAH gene coding sequence,
   wherein the mutation in both alleles is indicative of blood type B,
   thereby distinguishing blood type B from blood types A and AB.

2. The method of claim 1, wherein the detection of the mutation comprises:
   (a) specifically amplifying a subsequence of the gene encoding CMAH containing the mutation, thereby amplifying nucleic acids comprising the mutation; and
   (b) detecting the amplified nucleic acids.

3. The method of claim 2, wherein the subsequence is specifically amplified using primers comprising the sequences set forth in SEQ ID NO: 6 and 7.

4. The method of claim 2, wherein the amplified nucleic acids are detected by sequencing.

5. A method of identifying a blood type B carrier in a cat, comprising the steps of providing a biological sample and detecting the presence or absence of a mutation of the feline CMAH gene,
   wherein the mutation is a G to A substitution at position 139 of the feline CMAH gene coding sequence, and
   wherein presence of the mutation is indicative of blood type B,
   thereby identifying a blood type B carrier in the cat.

* * * * *

SEQUENCE LISTING

<160> NUMBER OF SEQ ID NOS: 98

<210> SEQ ID NO 1
<211> LENGTH: 1734
<212> TYPE: DNA
<213> ORGANISM: Artificial Sequence
<220> FEATURE:
<223> OTHER INFORMATION: composite feline cytidine monophospho-N-
      acetylneuraminic acid hydroxylase (CMAH) coding sequence

<400> SEQUENCE: 1

| atgggcagca ttgaacagac gacggaggtc ttgttgtgty tgtcacctgg agaagctgct | 60 |
| gacctgaagg aaggaatcaa tttcttgaga acaagaagr ccggcaaaga tttcattctg | 120 |
| tacaagagca agaatcgcrt gagggcgtgc aagaacgtgt gcaagcatca aggaggcctg | 180 |
| ttcataaaag acatcgaaga tttagacgga aggtctgtca gatgcacaaa gcacaactgg | 240 |
| aggttggatg tgagcaccat gaaawacgtc aatcccccag gcagcttctg tcaagacgaa | 300 |
| ctagttgttg aaatggatga agamaatgga cttttacttc tagaactgaa tcctcccaat | 360 |
| ccctgggatt cagaacccag atctcctgaa catttggctt ttggagaagt gcagatcacg | 420 |
| tacctcaccc acgcctgcat ggacctcaag ctgggagaca agaggatggt gtttgacccc | 480 |
| tggttaacgg gtcctgcgtt cgcccgaggc tggtggctgc tgcacgagcc tccgtctgat | 540 |
| tggctggaga ggctgtgcca ggcagacctg atttacatca gtcacatgca ctcagaccac | 600 |
| ctgagttacc ccacactgaa ggagctggct gggagaagac cggatattcc catttatgtt | 660 |
| ggaaacacgg aaagacctgt attttggaat ctgaatcaga gcggtgtcca gttgaccaat | 720 |
| atcaatatag tgccattcgg aatatggcag caggtagaca aaaatcttcg attcatgatc | 780 |
| ttgatggatg gcgttcatcc tgagatggac acttgcatta ttgtggagta taaggtcat | 840 |
| aagatactta atacagtgga ctgcaccaga cccaatgggg aaggttgcc tgagaaggtt | 900 |
| gctctaatga tgagtgattt tgctggagga gcatcaggct ttccaatgac tttcagtggt | 960 |
| ggaaaattta ccgaggaatg gaaagcccar ttcattaaag cagagaggaa gaagctcttg | 1020 |

```
aactacaagg cccggctggt gaaggaccta caaccccgaa tttattgccc ctttgctggg     1080
tattttgtgg aatctcaccc atcagacaag tatattaagg aaacaaacat caaaaatgac     1140
ccaaatgaac tcaataatct tatcaagaaa aactctgatg tggtaacgtg gaccccacgg     1200
cctggagcca ctcttgatct gagtcggatg ctaaaggacc cgacagacag caagggcatc     1260
atagarcctc cagaggggac caagatctac aaggattcct gggactttga accctatttg     1320
aacatcttga tgctgctgt aggagatgag atatttcttc actcatcctg gataaaagaa     1380
tacttcacyt gggckggatt taaggattac aacctggtgg tcaggatgat tgaaacagat     1440
gaggacttca gcccttttcc yggaggatat gactatttgg ttgactttct agacttatcc     1500
tttccaaaag agagaccaag ccgggaacac ccgtatgagg aaattcggag ccgggttgac     1560
gtcatcagac acgtggtaaa gaacggtctt ctctgggacr acttgtatat aggattccaa     1620
acccggctgc aacggagtcc tgacatatac catcacctgt tttggaacca ttttcaaata     1680
aaactccctc tcacgccacc caactggagg tccttcctga tgcactgtgg gtag           1734
```

<210> SEQ ID NO 2
<211> LENGTH: 763
<212> TYPE: DNA
<213> ORGANISM: Felis catus
<220> FEATURE:
<223> OTHER INFORMATION: feline blood type A cytidine monophospho-N-
      acetylneuraminic acid hydroxylase (CMAH) genomic sequence
      including 5' UTR to exon 2

<400> SEQUENCE: 2

```
acggaggttc tgtgggaaag ttaactcacg aagtagctag ctggtagaga tacaccgcgt      60
gacaggccgt gtgctcagcg acagggaggg agaatgtttg gaaaagcgtc cctatgtaaa     120
taaacggggc accgtgccgg gtgtaaggtt ctcatgttct acagaatggt agtgcgtatc     180
agcacgtgta ggcttgtccc gggggtggct ttggaggctt gacccaggct ggggtaggac     240
gactgggttc tatttgaacc tggagggtgg taaacatgac tagtggtgaa agttgaaccg     300
tgcttgtgag caaaaggatc agatctaaac gcagaagtgt gcaggtggga gcgggcaggg     360
tgggcacctg gagcccaata ggatcctgcg tctgaagcaa cacagcagag gaagtggtgc     420
aacggaatca gtagtgaacc gcgtgcatat gcatcctccg tctcatactt tgtgggagca     480
aacgagcaac caccgtcctt tcagaattcc caggagagg cagctgcgga ccatgggcag     540
gcaagtgaca ggggcattgg gtctggagga acccgagacc aacactgagc aagcagagcg     600
tgcatttcca ggggagcagc caagcctggg tcctgcgagg gagggggcttg agcctatcgc     660 ggtggaaaga ggctttgagc cgccagtttc aaaagatgct ctcctaagtc ttaacgttat     720
taacctttcc tcccccaaat gtctgccttt ccgtagcatt gaa                       763
```

<210> SEQ ID NO 3
<211> LENGTH: 577
<212> TYPE: PRT
<213> ORGANISM: Felis catus
<220> FEATURE:
<223> OTHER INFORMATION: feline cytidine monophospho-N-acetylneuraminic
      acid hydroxylase (CMAH)

<400> SEQUENCE: 3

Met Gly Ser Ile Glu Gln Thr Thr Glu Val Leu Leu Cys Leu Ser Pro
 1               5                  10                  15

Gly Glu Ala Ala Asp Leu Lys Glu Gly Ile Asn Phe Leu Arg Asn Lys
            20                  25                  30

Lys Thr Gly Lys Asp Phe Ile Leu Tyr Lys Ser Lys Asn Arg Val Arg

-continued

```
                35                  40                  45
Ala Cys Lys Asn Val Cys Lys His Gln Gly Gly Leu Phe Ile Lys Asp
 50                  55                  60

Ile Glu Asp Leu Asp Gly Arg Ser Val Arg Cys Thr Lys His Asn Trp
 65                  70                  75                  80

Arg Leu Asp Val Ser Thr Met Lys Tyr Val Asn Pro Pro Gly Ser Phe
                 85                  90                  95

Cys Gln Asp Glu Leu Val Val Glu Met Asp Glu Asn Gly Leu Leu
                100                 105                 110

Leu Leu Glu Leu Asn Pro Pro Asn Pro Trp Asp Ser Glu Pro Arg Ser
                115                 120                 125

Pro Glu His Leu Ala Phe Gly Glu Val Gln Ile Thr Tyr Leu Thr His
130                 135                 140

Ala Cys Met Asp Leu Lys Leu Gly Asp Lys Arg Met Val Phe Asp Pro
145                 150                 155                 160

Trp Leu Thr Gly Pro Ala Phe Ala Arg Gly Trp Trp Leu Leu His Glu
                165                 170                 175

Pro Pro Ser Asp Trp Leu Glu Arg Leu Cys Gln Ala Asp Leu Ile Tyr
                180                 185                 190

Ile Ser His Met His Ser Asp His Leu Ser Tyr Pro Thr Leu Lys Glu
                195                 200                 205

Leu Ala Gly Arg Arg Pro Asp Ile Pro Ile Tyr Val Gly Asn Thr Glu
210                 215                 220

Arg Pro Val Phe Trp Asn Leu Asn Gln Ser Gly Val Gln Leu Thr Asn
225                 230                 235                 240

Ile Asn Ile Val Pro Phe Gly Ile Trp Gln Gln Val Asp Lys Asn Leu
                245                 250                 255

Arg Phe Met Ile Leu Met Asp Gly Val His Pro Glu Met Asp Thr Cys
                260                 265                 270

Ile Ile Val Glu Tyr Lys Gly His Lys Ile Leu Asn Thr Val Asp Cys
                275                 280                 285

Thr Arg Pro Asn Gly Gly Arg Leu Pro Glu Lys Val Ala Leu Met Met
290                 295                 300

Ser Asp Phe Ala Gly Gly Ala Ser Gly Phe Pro Met Thr Phe Ser Gly
305                 310                 315                 320

Gly Lys Phe Thr Glu Glu Trp Lys Ala Gln Phe Ile Lys Ala Glu Arg
                325                 330                 335

Lys Lys Leu Leu Asn Tyr Lys Ala Arg Leu Val Lys Asp Leu Gln Pro
                340                 345                 350

Arg Ile Tyr Cys Pro Phe Ala Gly Tyr Phe Val Glu Ser His Pro Ser
                355                 360                 365

Asp Lys Tyr Ile Lys Glu Thr Asn Ile Lys Asn Asp Pro Asn Glu Leu
                370                 375                 380

Asn Asn Leu Ile Lys Lys Asn Ser Asp Val Val Thr Trp Thr Pro Arg
385                 390                 395                 400

Pro Gly Ala Thr Leu Asp Leu Ser Arg Met Leu Lys Asp Pro Thr Asp
                405                 410                 415

Ser Lys Gly Ile Ile Glu Pro Pro Glu Gly Thr Lys Ile Tyr Lys Asp
                420                 425                 430

Ser Trp Asp Phe Glu Pro Tyr Leu Asn Ile Leu Asn Ala Ala Val Gly
                435                 440                 445

Asp Glu Ile Phe Leu His Ser Ser Trp Ile Lys Glu Tyr Phe Thr Trp
                450                 455                 460
```

-continued

```
Ala Gly Phe Lys Asp Tyr Asn Leu Val Val Arg Met Ile Glu Thr Asp
465                 470                 475                 480

Glu Asp Phe Ser Pro Phe Pro Gly Gly Tyr Asp Tyr Leu Val Asp Phe
                485                 490                 495

Leu Asp Leu Ser Phe Pro Lys Glu Arg Pro Ser Arg Glu His Pro Tyr
                500                 505                 510

Glu Glu Ile Arg Ser Arg Val Asp Val Ile Arg His Val Val Lys Asn
            515                 520                 525

Gly Leu Leu Trp Asp Asp Leu Tyr Ile Gly Phe Gln Thr Arg Leu Gln
        530                 535                 540

Arg Ser Pro Asp Ile Tyr His His Leu Phe Trp Asn His Phe Gln Ile
545                 550                 555                 560

Lys Leu Pro Leu Thr Pro Pro Asn Trp Arg Ser Phe Leu Met His Cys
                565                 570                 575

Gly
```

```
<210> SEQ ID NO 4
<211> LENGTH: 19
<212> TYPE: DNA
<213> ORGANISM: Artificial Sequence
<220> FEATURE:
<223> OTHER INFORMATION: synthetic PCR amplification forward 5' primer
      for 5'UTR - exon 1 for mutant CMAH

<400> SEQUENCE: 4
ttcctttgct gctggagtg                                                19

<210> SEQ ID NO 5
<211> LENGTH: 20
<212> TYPE: DNA
<213> ORGANISM: Artificial Sequence
<220> FEATURE:
<223> OTHER INFORMATION: synthetic reverse primer for CMAH 5'UTR -
      exon 1

<400> SEQUENCE: 5
gctctgcttg ctcagtgttg                                               20

<210> SEQ ID NO 6
<211> LENGTH: 20
<212> TYPE: DNA
<213> ORGANISM: Artificial Sequence
<220> FEATURE:
<223> OTHER INFORMATION: synthetic PCR amplification 3' primer for
      exon 1 - 5' UTR, forward 5' primer for exon 2 for mutant CMAH,
      reverse primer for CMAH 5'UTR - exon 1

<400> SEQUENCE: 6
caacactgag caagcagagc                                               20

<210> SEQ ID NO 7
<211> LENGTH: 20
<212> TYPE: DNA
<213> ORGANISM: Artificial Sequence
<220> FEATURE:
<223> OTHER INFORMATION: synthetic reverse primer for CMAH exon 2

<400> SEQUENCE: 7
cccctgagag agaggaaacc                                               20

<210> SEQ ID NO 8
<211> LENGTH: 22
<212> TYPE: DNA
<213> ORGANISM: Artificial Sequence
```

```
<220> FEATURE:
<223> OTHER INFORMATION: synthetic forward 5' primer for CMAH exon 3

<400> SEQUENCE: 8
ctcttaggac atggactgaa cg                                              22

<210> SEQ ID NO 9
<211> LENGTH: 21
<212> TYPE: DNA
<213> ORGANISM: Artificial Sequence
<220> FEATURE:
<223> OTHER INFORMATION: synthetic reverse primer for CMAH exon 3

<400> SEQUENCE: 9
ctctcacccg tcttaccaaa g                                               21

<210> SEQ ID NO 10
<211> LENGTH: 20
<212> TYPE: DNA
<213> ORGANISM: Artificial Sequence
<220> FEATURE:
<223> OTHER INFORMATION: synthetic forward primer for CMAH exon 5

<400> SEQUENCE: 10
gtgtctgtcg catcacctct                                                 20

<210> SEQ ID NO 11
<211> LENGTH: 20
<212> TYPE: DNA
<213> ORGANISM: Artificial Sequence
<220> FEATURE:
<223> OTHER INFORMATION: synthetic reverse primer for CMAH exon 5

<400> SEQUENCE: 11
gagtccgctt cttctcatcc                                                 20

<210> SEQ ID NO 12
<211> LENGTH: 20
<212> TYPE: DNA
<213> ORGANISM: Artificial Sequence
<220> FEATURE:
<223> OTHER INFORMATION: synthetic forward primer for CMAH exon 6

<400> SEQUENCE: 12
ggcagagagc aggaagacac                                                 20

<210> SEQ ID NO 13
<211> LENGTH: 20
<212> TYPE: DNA
<213> ORGANISM: Artificial Sequence
<220> FEATURE:
<223> OTHER INFORMATION: synthetic reverse primer for CMAH exon 6

<400> SEQUENCE: 13
cattggtaaa tgggggaaaa                                                 20

<210> SEQ ID NO 14
<211> LENGTH: 20
<212> TYPE: DNA
<213> ORGANISM: Artificial Sequence
<220> FEATURE:
<223> OTHER INFORMATION: synthetic forward primer for CMAH exon 7

<400> SEQUENCE: 14
tagccgattt ttgtctgtgc                                                 20
```

```
<210> SEQ ID NO 15
<211> LENGTH: 22
<212> TYPE: DNA
<213> ORGANISM: Artificial Sequence
<220> FEATURE:
<223> OTHER INFORMATION: synthetic reverse primer for CMAH exon 7

<400> SEQUENCE: 15
gggtgatgta tggaagtgtt ga                                              22

<210> SEQ ID NO 16
<211> LENGTH: 20
<212> TYPE: DNA
<213> ORGANISM: Artificial Sequence
<220> FEATURE:
<223> OTHER INFORMATION: synthetic forward primer for CMAH exon 8

<400> SEQUENCE: 16
gatcccatca tgcttcctct                                                 20

<210> SEQ ID NO 17
<211> LENGTH: 20
<212> TYPE: DNA
<213> ORGANISM: Artificial Sequence
<220> FEATURE:
<223> OTHER INFORMATION: synthetic reverse primer for CMAH exon 8

<400> SEQUENCE: 17
tgctttgcaa gtctggtttc                                                 20

<210> SEQ ID NO 18
<211> LENGTH: 20
<212> TYPE: DNA
<213> ORGANISM: Artificial Sequence
<220> FEATURE:
<223> OTHER INFORMATION: synthetic forward primer for CMAH exon 9

<400> SEQUENCE: 18
gtgtctttgg ctggtttggt                                                 20

<210> SEQ ID NO 19
<211> LENGTH: 20
<212> TYPE: DNA
<213> ORGANISM: Artificial Sequence
<220> FEATURE:
<223> OTHER INFORMATION: synthetic reverse primer for CMAH exon 9

<400> SEQUENCE: 19
gaatggcgtg gctaaaagtc                                                 20

<210> SEQ ID NO 20
<211> LENGTH: 20
<212> TYPE: DNA
<213> ORGANISM: Artificial Sequence
<220> FEATURE:
<223> OTHER INFORMATION: synthetic forward primer for CMAH exon 11

<400> SEQUENCE: 20
gccacacagc tcccatagac                                                 20

<210> SEQ ID NO 21
<211> LENGTH: 20
<212> TYPE: DNA
<213> ORGANISM: Artificial Sequence
<220> FEATURE:
<223> OTHER INFORMATION: synthetic forward primer for CMAH exon 11

<400> SEQUENCE: 21
```
ccacaaaacc cacaacaaca                                          20

<210> SEQ ID NO 22
<211> LENGTH: 20
<212> TYPE: DNA
<213> ORGANISM: Artificial Sequence
<220> FEATURE:
<223> OTHER INFORMATION: synthetic forward primer for CMAH exon 12

<400> SEQUENCE: 22
catggtgttt gctgtctcat                                          20

<210> SEQ ID NO 23
<211> LENGTH: 20
<212> TYPE: DNA
<213> ORGANISM: Artificial Sequence
<220> FEATURE:
<223> OTHER INFORMATION: synthetic reverse primer for CMAH exon 12

<400> SEQUENCE: 23
gggcagtaag catgtagagg                                          20

<210> SEQ ID NO 24
<211> LENGTH: 19
<212> TYPE: DNA
<213> ORGANISM: Artificial Sequence
<220> FEATURE:
<223> OTHER INFORMATION: synthetic forward primer for CMAH exon 13

<400> SEQUENCE: 24
gacatgaggg gtcggtacg                                           19

<210> SEQ ID NO 25
<211> LENGTH: 20
<212> TYPE: DNA
<213> ORGANISM: Artificial Sequence
<220> FEATURE:
<223> OTHER INFORMATION: synthetic reverse primer for CMAH exon 13

<400> SEQUENCE: 25
aaatgcacgc tggagttgag                                          20

<210> SEQ ID NO 26
<211> LENGTH: 20
<212> TYPE: DNA
<213> ORGANISM: Artificial Sequence
<220> FEATURE:
<223> OTHER INFORMATION: synthetic forward primer for CMAH exon 14

<400> SEQUENCE: 26
ttcactgttg gatgatgtgg                                          20

<210> SEQ ID NO 27
<211> LENGTH: 21
<212> TYPE: DNA
<213> ORGANISM: Artificial Sequence
<220> FEATURE:
<223> OTHER INFORMATION: synthetic reverse primer for CMAH exon 14

<400> SEQUENCE: 27
cttctcactc ccctgaaagt c                                        21

<210> SEQ ID NO 28
<211> LENGTH: 20
<212> TYPE: DNA
<213> ORGANISM: Artificial Sequence

```
<220> FEATURE:
<223> OTHER INFORMATION: synthetic nested forward primer for CMAH cDNA
      exons 2-6 (cDNAe2-6)

<400> SEQUENCE: 28
gacgacggag gtcttgttgt                                                20

<210> SEQ ID NO 29
<211> LENGTH: 20
<212> TYPE: DNA
<213> ORGANISM: Artificial Sequence
<220> FEATURE:
<223> OTHER INFORMATION: synthetic reverse primer for CMAH cDNA
      exons 2-6

<400> SEQUENCE: 29
gctccttcag tgtgggtaa                                                 20

<210> SEQ ID NO 30
<211> LENGTH: 20
<212> TYPE: DNA
<213> ORGANISM: Artificial Sequence
<220> FEATURE:
<223> OTHER INFORMATION: synthetic nested forward primer for CMAH cDNA
      exons 5-11 (cDNAe5-11)

<400> SEQUENCE: 30
caagaggatg gtgtttgacc                                                20

<210> SEQ ID NO 31
<211> LENGTH: 20
<212> TYPE: DNA
<213> ORGANISM: Artificial Sequence
<220> FEATURE:
<223> OTHER INFORMATION: synthetic reverse primer for CMAH cDNA
      exons 5-11

<400> SEQUENCE: 31
ctctggaggc tctatgatgc                                                20

<210> SEQ ID NO 32
<211> LENGTH: 20
<212> TYPE: DNA
<213> ORGANISM: Artificial Sequence
<220> FEATURE:
<223> OTHER INFORMATION: synthetic nested forward primer for CMAH cDNA
      exons 9-14 (cDNAe9-14)

<400> SEQUENCE: 32
ggaatctcac ccatcagaca                                                20

<210> SEQ ID NO 33
<211> LENGTH: 20
<212> TYPE: DNA
<213> ORGANISM: Artificial Sequence
<220> FEATURE:
<223> OTHER INFORMATION: synthetic reverse primer for CMAH cDNA
      exons 9-14

<400> SEQUENCE: 33
caggtctgct ctacccacag                                                20

<210> SEQ ID NO 34
<211> LENGTH: 28
<212> TYPE: DNA
<213> ORGANISM: Artificial Sequence
<220> FEATURE:
<223> OTHER INFORMATION: synthetic CMAH 5' RACE primer
```

<400> SEQUENCE: 34
agaagctgcc tgggggattg acgtattt                                              28

<210> SEQ ID NO 35
<211> LENGTH: 25
<212> TYPE: DNA
<213> ORGANISM: Artificial Sequence
<220> FEATURE:
<223> OTHER INFORMATION: synthetic CMAH 3' RACE primer

<400> SEQUENCE: 35
aactccctct cacgccaccc aactg                                                 25

<210> SEQ ID NO 36
<211> LENGTH: 22
<212> TYPE: DNA
<213> ORGANISM: Artificial Sequence
<220> FEATURE:
<223> OTHER INFORMATION: synthetic forward primer for CMAH delta-53

<400> SEQUENCE: 36
tcctccgtct catactttgt gg                                                    22

<210> SEQ ID NO 37
<211> LENGTH: 18
<212> TYPE: DNA
<213> ORGANISM: Artificial Sequence
<220> FEATURE:
<223> OTHER INFORMATION: synthetic reverse primer for CMAH delta-53

<400> SEQUENCE: 37
gctgctcccc tggaaatg                                                         18

<210> SEQ ID NO 38
<211> LENGTH: 18
<212> TYPE: DNA
<213> ORGANISM: Artificial Sequence
<220> FEATURE:
<223> OTHER INFORMATION: synthetic forward primer for CMAH UTR SNPs

<400> SEQUENCE: 38
gccgggtgta aggttctc                                                         18

<210> SEQ ID NO 39
<211> LENGTH: 18
<212> TYPE: DNA
<213> ORGANISM: Artificial Sequence
<220> FEATURE:
<223> OTHER INFORMATION: synthetic reverse primer for CMAH UTR SNPs

<400> SEQUENCE: 39
cctattgggc tccaggtg                                                         18

<210> SEQ ID NO 40
<211> LENGTH: 14
<212> TYPE: DNA
<213> ORGANISM: Artificial Sequence
<220> FEATURE:
<223> OTHER INFORMATION: synthetic pyrosequencing primer for CMAH C-371T

<400> SEQUENCE: 40
agcctacacg tgct                                                             14

<210> SEQ ID NO 41
<211> LENGTH: 13

```
<212> TYPE: DNA
<213> ORGANISM: Artificial Sequence
<220> FEATURE:
<223> OTHER INFORMATION: synthetic pyrosequencing primer for CMAH G-217A

<400> SEQUENCE: 41
cacctgcaca ctt                                                        13

<210> SEQ ID NO 42
<211> LENGTH: 22
<212> TYPE: DNA
<213> ORGANISM: Artificial Sequence
<220> FEATURE:
<223> OTHER INFORMATION: synthetic forward primer for CMAH exon 2

<400> SEQUENCE: 42
tgtcagatgc acaaagcaca ac                                              22

<210> SEQ ID NO 43
<211> LENGTH: 20
<212> TYPE: DNA
<213> ORGANISM: Artificial Sequence
<220> FEATURE:
<223> OTHER INFORMATION: synthetic reverse primer for CMAH exon 2

<400> SEQUENCE: 43
acgccagtaa cgatcacagc                                                 20

<210> SEQ ID NO 44
<211> LENGTH: 16
<212> TYPE: DNA
<213> ORGANISM: Artificial Sequence
<220> FEATURE:
<223> OTHER INFORMATION: synthetic pyrosequencing primer for CMAH G139A

<400> SEQUENCE: 44
tgtgagcacc atgaaa                                                     16

<210> SEQ ID NO 45
<211> LENGTH: 22
<212> TYPE: DNA
<213> ORGANISM: Artificial Sequence
<220> FEATURE:
<223> OTHER INFORMATION: synthetic forward primer for CMAH exon 2

<400> SEQUENCE: 45
ctgctgacct gaaggaagga at                                              22

<210> SEQ ID NO 46
<211> LENGTH: 20
<212> TYPE: DNA
<213> ORGANISM: Artificial Sequence
<220> FEATURE:
<223> OTHER INFORMATION: synthetic reverse primer for CMAH exon 2

<400> SEQUENCE: 46
acccgtgaga aggctcagaa                                                 20

<210> SEQ ID NO 47
<211> LENGTH: 14
<212> TYPE: DNA
<213> ORGANISM: Artificial Sequence
<220> FEATURE:
<223> OTHER INFORMATION: synthetic pyrosequencing primer for CMAH T265A

<400> SEQUENCE: 47
ggcgtgcaag aacg                                                       14
```

<210> SEQ ID NO 48
<211> LENGTH: 22
<212> TYPE: DNA
<213> ORGANISM: Artificial Sequence
<220> FEATURE:
<223> OTHER INFORMATION: synthetic forward primer for CMAH exon 4

<400> SEQUENCE: 48
tgtcagatgc acaaagcaca ac                                              22

<210> SEQ ID NO 49
<211> LENGTH: 20
<212> TYPE: DNA
<213> ORGANISM: Artificial Sequence
<220> FEATURE:
<223> OTHER INFORMATION: synthetic forward primer for CMAH exon 4

<400> SEQUENCE: 49
acgccagtaa cgatcacagc                                                 20

<210> SEQ ID NO 50
<211> LENGTH: 16
<212> TYPE: DNA
<213> ORGANISM: Artificial Sequence
<220> FEATURE:
<223> OTHER INFORMATION: synthetic pyrosequencing primer for CMAH A324C

<400> SEQUENCE: 50
tgtgagcacc atgaaa                                                     16

<210> SEQ ID NO 51
<211> LENGTH: 25
<212> TYPE: DNA
<213> ORGANISM: Artificial Sequence
<220> FEATURE:
<223> OTHER INFORMATION: synthetic forward primer for CMAH exon 10

<400> SEQUENCE: 51
cgactaactg tcacctttgt gtctt                                           25

<210> SEQ ID NO 52
<211> LENGTH: 22
<212> TYPE: DNA
<213> ORGANISM: Artificial Sequence
<220> FEATURE:
<223> OTHER INFORMATION: synthetic reverse primer for CMAH exon 10

<400> SEQUENCE: 52
tcatctccta cagcagcatt ca                                              22

<210> SEQ ID NO 53
<211> LENGTH: 16
<212> TYPE: DNA
<213> ORGANISM: Artificial Sequence
<220> FEATURE:
<223> OTHER INFORMATION: synthetic pyrosequencing primer for CMAH G1266A

<400> SEQUENCE: 53
aagcaagggc atcata                                                     16

<210> SEQ ID NO 54
<211> LENGTH: 18
<212> TYPE: DNA
<213> ORGANISM: Artificial Sequence
<220> FEATURE:
<223> OTHER INFORMATION: synthetic forward primer for CMAH exon 12

-continued

```
<400> SEQUENCE: 54
attcggagcc gggttgac                                                18

<210> SEQ ID NO 55
<211> LENGTH: 22
<212> TYPE: DNA
<213> ORGANISM: Artificial Sequence
<220> FEATURE:
<223> OTHER INFORMATION: synthetic reverse primer for CMAH exon 12

<400> SEQUENCE: 55
caggcacttt ccaacttaca gg                                           22

<210> SEQ ID NO 56
<211> LENGTH: 20
<212> TYPE: DNA
<213> ORGANISM: Artificial Sequence
<220> FEATURE:
<223> OTHER INFORMATION: synthetic pyrosequencing primer for CMAH G1591A

<400> SEQUENCE: 56
gggtttggaa tcctatatac                                              20

<210> SEQ ID NO 57
<211> LENGTH: 18
<212> TYPE: DNA
<213> ORGANISM: Artificial Sequence
<220> FEATURE:
<223> OTHER INFORMATION: synthetic 18 bp insert at position -53 of 5'
      UTR

<400> SEQUENCE: 57
aacgagcaac cgaagctg                                                18

<210> SEQ ID NO 58
<211> LENGTH: 115
<212> TYPE: DNA
<213> ORGANISM: Artificial Sequence
<220> FEATURE:
<223> OTHER INFORMATION: synthetic feline blood type A CMAH cDNA 5' UTR
      region

<400> SEQUENCE: 58
agtagtgaac cgcgtgcata tgcatcctcc gtctcatact ttgtgggagc aaacgagcaa   60
ccaccgtcct ttcagaattc ccagggagag gcagctgcgg accatgggca gcatt        115

<210> SEQ ID NO 59
<211> LENGTH: 77
<212> TYPE: DNA
<213> ORGANISM: Artificial Sequence
<220> FEATURE:
<223> OTHER INFORMATION: synthetic feline blood type Ab CMAH
      alternatively spliced cDNA 5' UTR region

<400> SEQUENCE: 59
cagtttcaaa agatgctctc ctaagtctta acgttattaa cctttcctcc cccaaatgtc   60
tgcctttccg tagcatt                                                 77

<210> SEQ ID NO 60
<211> LENGTH: 20
<212> TYPE: DNA
<213> ORGANISM: Artificial Sequence
<220> FEATURE:
<223> OTHER INFORMATION: synthetic PCR amplification reverse 3' primer
      for CMAH exon 2, PCR amplification 3' primer for mutant CMAH
```

```
                            exon 2

<400> SEQUENCE: 60
ggtttcctct ctctcagggg                                               20

<210> SEQ ID NO 61
<211> LENGTH: 21
<212> TYPE: DNA
<213> ORGANISM: Artificial Sequence
<220> FEATURE:
<223> OTHER INFORMATION: synthetic PCR amplification reverse 3' primer
      for CMAH exon 3

<400> SEQUENCE: 61
ctttggtaag acgggtgaga g                                             21

<210> SEQ ID NO 62
<211> LENGTH: 20
<212> TYPE: DNA
<213> ORGANISM: Artificial Sequence
<220> FEATURE:
<223> OTHER INFORMATION: synthetic gene specific primer CMAH_GSP_5'

<400> SEQUENCE: 62
gaggtacgtg atctgcactt                                               20

<210> SEQ ID NO 63
<211> LENGTH: 21
<212> TYPE: DNA
<213> ORGANISM: Artificial Sequence
<220> FEATURE:
<223> OTHER INFORMATION: synthetic pyrosequencing M13 biotinylated
      primer for CMAH SNP genomic sequence analysis

<400> SEQUENCE: 63
agcgcataac aatttcacag g                                             21

<210> SEQ ID NO 64
<211> LENGTH: 20
<212> TYPE: DNA
<213> ORGANISM: Artificial Sequence
<220> FEATURE:
<223> OTHER INFORMATION: synthetic reverse primer for CMAH exon 5

<400> SEQUENCE: 64
ggatgagaag aagcggactc                                               20

<210> SEQ ID NO 65
<211> LENGTH: 20
<212> TYPE: DNA
<213> ORGANISM: Artificial Sequence
<220> FEATURE:
<223> OTHER INFORMATION: synthetic reverse primer for CMAH exon 6

<400> SEQUENCE: 65
ttttccccca tttaccaatg                                               20

<210> SEQ ID NO 66
<211> LENGTH: 22
<212> TYPE: DNA
<213> ORGANISM: Artificial Sequence
<220> FEATURE:
<223> OTHER INFORMATION: synthetic reverse primer for CMAH exon 7

<400> SEQUENCE: 66
tcaacacttc catacatcac cc                                            22
```

```
<210> SEQ ID NO 67
<211> LENGTH: 20
<212> TYPE: DNA
<213> ORGANISM: Artificial Sequence
<220> FEATURE:
<223> OTHER INFORMATION: synthetic reverse primer for CMAH exon 8

<400> SEQUENCE: 67
gaaaccagac ttgcaaagca                                              20

<210> SEQ ID NO 68
<211> LENGTH: 20
<212> TYPE: DNA
<213> ORGANISM: Artificial Sequence
<220> FEATURE:
<223> OTHER INFORMATION: synthetic reverse primer for CMAH exon 9

<400> SEQUENCE: 68 gactttagc cacgccattc                                               20

<210> SEQ ID NO 69
<211> LENGTH: 20
<212> TYPE: DNA
<213> ORGANISM: Artificial Sequence
<220> FEATURE:
<223> OTHER INFORMATION: synthetic reverse primer for CMAH exon 11

<400> SEQUENCE: 69
tgttgttgtg ggttttgtgg                                              20

<210> SEQ ID NO 70
<211> LENGTH: 20
<212> TYPE: DNA
<213> ORGANISM: Artificial Sequence
<220> FEATURE:
<223> OTHER INFORMATION: synthetic reverse primer for CMAH exon 12

<400> SEQUENCE: 70
cctctacatg cttactgccc                                              20

<210> SEQ ID NO 71
<211> LENGTH: 20
<212> TYPE: DNA
<213> ORGANISM: Artificial Sequence
<220> FEATURE:
<223> OTHER INFORMATION: synthetic reverse primer for CMAH exon 13

<400> SEQUENCE: 71
ctcaactcca gcgtgcattt                                              20

<210> SEQ ID NO 72
<211> LENGTH: 21
<212> TYPE: DNA
<213> ORGANISM: Artificial Sequence
<220> FEATURE:
<223> OTHER INFORMATION: synthetic reverse primer for CMAH exon 14

<400> SEQUENCE: 72
gactttcagg ggagtgagaa g                                            21

<210> SEQ ID NO 73
<211> LENGTH: 20
<212> TYPE: DNA
<213> ORGANISM: Artificial Sequence
<220> FEATURE:
<223> OTHER INFORMATION: synthetic reverse nested primer for CMAH
      cDNAe2-6
```

```
<400> SEQUENCE: 73
ttaccccaca ctgaaggagc                                              20

<210> SEQ ID NO 74
<211> LENGTH: 20
<212> TYPE: DNA
<213> ORGANISM: Artificial Sequence
<220> FEATURE:
<223> OTHER INFORMATION: synthetic reverse nested primer for CMAH
      cDNAe5-11

<400> SEQUENCE: 74
gcatcataga gcctccagag                                              20

<210> SEQ ID NO 75
<211> LENGTH: 20
<212> TYPE: DNA
<213> ORGANISM: Artificial Sequence
<220> FEATURE:
<223> OTHER INFORMATION: synthetic reverse nested primer for CMAH
      cDNAe9-14

<400> SEQUENCE: 75
ctgtgggtag agcagacctg                                              20

<210> SEQ ID NO 76
<211> LENGTH: 28
<212> TYPE: DNA
<213> ORGANISM: Artificial Sequence
<220> FEATURE:
<223> OTHER INFORMATION: synthetic CMAH 5' RACE reverse primer

<400> SEQUENCE: 76
aaatacgtca atcccccagg cagcttct                                     28

<210> SEQ ID NO 77
<211> LENGTH: 18
<212> TYPE: DNA
<213> ORGANISM: Artificial Sequence
<220> FEATURE:
<223> OTHER INFORMATION: synthetic reverse primer for CMAH delta-53

<400> SEQUENCE: 77
catttccagg ggagcagc                                                18

<210> SEQ ID NO 78
<211> LENGTH: 18
<212> TYPE: DNA
<213> ORGANISM: Artificial Sequence
<220> FEATURE:
<223> OTHER INFORMATION: synthetic reverse primer for CMAH UTR SNPs

<400> SEQUENCE: 78
cacctggagc ccaatagg                                                18

<210> SEQ ID NO 79
<211> LENGTH: 14
<212> TYPE: DNA
<213> ORGANISM: Artificial Sequence
<220> FEATURE:
<223> OTHER INFORMATION: synthetic pyrosequencing reverse primer for
      CMAH C-371T

<400> SEQUENCE: 79
agcacgtgta ggct                                                    14
```

-continued

```
<210> SEQ ID NO 80
<211> LENGTH: 13
<212> TYPE: DNA
<213> ORGANISM: Artificial Sequence
<220> FEATURE:
<223> OTHER INFORMATION: synthetic pyrosequencing reverse primer for
      CMAH G-217A

<400> SEQUENCE: 80
aagtgtgcag gtg                                                          13

<210> SEQ ID NO 81
<211> LENGTH: 14
<212> TYPE: DNA
<213> ORGANISM: Artificial Sequence
<220> FEATURE:
<223> OTHER INFORMATION: synthetic pyrosequencing reverse primer for
      CMAH G139A

<400> SEQUENCE: 81
ggcgtgcaag aacg                                                         14

<210> SEQ ID NO 82
<211> LENGTH: 21
<212> TYPE: DNA
<213> ORGANISM: Artificial Sequence
<220> FEATURE:
<223> OTHER INFORMATION: synthetic reverse primer for CMAH exon 3

<400> SEQUENCE: 82
tgctgtgatc gttactggcg t                                                 21

<210> SEQ ID NO 83
<211> LENGTH: 22
<212> TYPE: DNA
<213> ORGANISM: Artificial Sequence
<220> FEATURE:
<223> OTHER INFORMATION: synthetic reverse primer for CMAH exon 10

<400> SEQUENCE: 83
tgaatgctgc tgtaggagat ga                                                22

<210> SEQ ID NO 84
<211> LENGTH: 22
<212> TYPE: DNA
<213> ORGANISM: Artificial Sequence
<220> FEATURE:
<223> OTHER INFORMATION: synthetic reverse primer for CMAH exon 12

<400> SEQUENCE: 84
cctgtaagtt ggaaagtgcc tg                                                22

<210> SEQ ID NO 85
<211> LENGTH: 20
<212> TYPE: DNA
<213> ORGANISM: Artificial Sequence
<220> FEATURE:
<223> OTHER INFORMATION: synthetic pyrosequencing reverse primer for
      CMAH G1591A

<400> SEQUENCE: 85
gtatatagga ttccaaaccc                                                   20

<210> SEQ ID NO 86
<211> LENGTH: 1722
<212> TYPE: DNA
<213> ORGANISM: Canis familiaris
```

```
<220> FEATURE:
<223> OTHER INFORMATION: dog cytidine monophospho-N-acetylneuraminic
      acid hydroxylase (CMAH) cDNA

<400> SEQUENCE: 86
agcattgaac aaacaacaga gatcctcttg catytgtcac ccattgaagt tgccaatctg      60
aaggaaggaa tcaatttctt tcgaaataag aacrctggca agattacat cctctacaag     120 aataagaatc acctgcgggc atgcaagaat atgtgcaagc atcaaggagg cctgttcata    180
aaagacatcg aggatttaga tggaaggtct gttagatgca caaaacacaa ctggaagtta    240
gatgtgagca ccatgaagwa tatcaacccc ccaagcagct tctgtcaaga tgaactagtt    300
gttgaaatgg atgaagamaa tggactttta cttctagaac tgaatcctcc taaccctgg     360 gattcagaac ccagagctcc ggaacatttg gcttttggag aaataacgta cctcgctcac    420
gcctgtatgg acctcaagct gggagacaag aggatggtgt tcgacccctg gttaataggt    480
cctgcctttg cccggggatg gtggctgctg cacgagcctc cctctgattg gctggagaag    540
ctgtgccagg cagacctaat ttacatcagt catatgcact cggaccatct cagctacccg    600
acactgaaga agcttgctga gaagaccaga gatattccca tttatgttgg aaacacggaa    660
agacctgtat tttggaatct gaatcagagc ggtgtccagt tgactaatat caatgtagtg    720
ccatttggaa tatggcagca ggtagacaaa atcttcgat tcatgatctt gatggatggc     780
attcatcctg agatggacac ttgcattatt gtggagtata aaggtcataa gatacttaat    840
acagtggact gcaccagacc caatggggga aggttgcctg agaaggttgc tctaatgatg    900
agtgattttg ctggaggagc atcaggcttt ccaatgactt tcagtggtgg aaaatttact    960
gaggaatgga agccgagtt cattaagaca gaaaggaaga agctcttgaa ctacaaagcc    1020
cggctggtga aggacctaca acctcgaatc tattgtccct ttgctgggta ttttgtggaa   1080
tcccatccat cagacaagta tattaaggaa acaaacatca aaaatgaccc aaatgagctt   1140
aataatctta tcaagaaaaa ctctgatgtg ataacatgga ccccacgacc tggagccact   1200
cttgatctga gtaggatgct aaaggaccca actgacagca agggcatcat agagcctcca   1260
aatgggacaa aaatttacaa ggattcctgg gactttggac catatttgaa agtcttgaat   1320
gctgcagtag aagatgaaat atttcttcac tcatcctgga taaaagaata tttcacytgg   1380
gcaggattta aggattataa cctggtggtc aggatgattg aaacaaatga ggacttcagc   1440
ccttttccyg gaggatatga ctatttggtt gacttttag atttatcctt tccaaaagaa   1500
agaccaagcc gggagcactc gtatgaggaa attcggagcc gggttgatgt catcagatat   1560
gtggtgaaaa atggtctact ctgggatrac ttgtatatag gattccaaac ccggctgcag   1620
cgggatcctg acatatacca tcatctgttt tggaaccatt ttcaaataaa actccctcta   1680
atgccaccca actggaggtc cttcttgatg cactgtgggt ag                     1722

<210> SEQ ID NO 87
<211> LENGTH: 1673
<212> TYPE: DNA
<213> ORGANISM: Canis familiaris
<220> FEATURE:
<223> OTHER INFORMATION: human cytidine monophospho-N-acetylneuraminic
      acid hydroxylase (CMAH)

<400> SEQUENCE: 87
atgggcagca tcgaacaaac aactgagatc ctgttgtgcy tatcacctgt tgaagttgcc      60
agtcttaagg aaggaatcaa tttctttcgc aataagagcr ctggcaaaga ctacgtcttg    120
tacaagaata agagccgact gagggcatgc aagaatatgt gcaagcacca aggaggcctg    180
```

```
ttcataaaag atatcgagga tttagccgga agttgttgaa atggatgaaa acaacggact    240
tttgctttta gaactgaatc ctcctaaccc ttgggactta cagcccagag ctccggaaca    300 tttggcttt tggagaaataa cgtacctcgc tcacgcctgt atggacctca agttaggaga    360
caagagaatg gtgtttgacc cttggttaat cggtcctgct tttgcccgtg gatggtggtt    420
gctccatgag cctccatctg attggctgga gaggctgtgc caggcagacc tcatttacat    480
cagtcatctg cactcagacc acctgagtta ccccacactg aaaaagcttg ctgggagaag    540
accagatatt cccatttatg ttggaaacac agaaaggcct gtattttgga atctgaatca    600
gagcggtgtc cagttgacta atatcaatgt cgtgccattt ggaatatggc agcaggtgga    660
caaaaatctt cgattcatga tcttgatgga cggtgttcat cctgagatgg acacttgcat    720
tattgtggag tacaaaggtc ataaaatact caatatagta gactgcacca gacccaatgg    780
gggaaggctg cctatgaagg ttgctctaat gatgagtgat tttgctggag gagcatcagg    840
ctttccaatg acttttcagtg gtggaaaatt tacggaggaa tggaaagccc arttcattaa    900
aacagaaagg aagaagctcc tgaactacaa ggctcggctg gtgaagaacc tgcaaccccg    960
aatttattgt ccctttgctg gtatttttgt ggaatctcac ccatcagaca agtacatcaa   1020
ggaaacaaac accaaaaatg acccaaatga actcaacaat cttatcaaga aaaactctga   1080
tgtgataaca tggaccccct gaccgggagc caccttgat ctgggaagaa tgctgaagga    1140
tcgaacagac agcaagggca tcatagagcc tccagagggg acaaaaattt acaaggattc   1200
ctgggacttt ggaccatatt tgaaagtctt gaatgctgca gtagaagatg aaatatttct   1260
tcactcatcc tggataaaag aatacttcac ttgggctgga tttaaagatt acaaccttgt   1320
ggtcaggatg attgagacag atgaggactt caatccttt ccyggaggat atgactattt    1380
ggttgacttt ttagatttat ccttcccaaa agaaagacca caacgagaac atccctatga   1440
ggaaatccat agccgggtgg atgtcatcag acacgtggtg aagaatggtc tactctggga   1500
tragttgtat ataggattcc aaacacggct ccagcgggat cctgacatat accatcacct   1560
gttttggaat cattttcaaa taaaactccc cctcacacca cccaactgga agtcattcct   1620
gatgtgctgt gagcagaagt ggcctgcgat tttgcaattc tctacagaaa gaa          1673
```

<210> SEQ ID NO 88
<211> LENGTH: 1734
<212> TYPE: DNA
<213> ORGANISM: Canis familiaris
<220> FEATURE:
<223> OTHER INFORMATION: mouse cytidine monophospho-N-acetylneuraminic
      acid hydroxylase (CMAH) cDNA

<400> SEQUENCE: 88

```
atgagtgaca ggaaacagac agctgagatc ctgctgaccy tgtctcctgc tgaagttgcc     60
aacctcaagg aagggatcaa ttttttttcga aataagactr ctgggaaaga gtacatttta    120
tacaaggaga aggaccatct aaaggcatgc aagaacctct gcaagcacca gggaggcctg    180
ttcatgaaag acatcgagga tttagatgga aggtccgtta atgcacaaa gcacaactgg    240 aagttagacg tgagcaccat gaaawatatc aaccctccag ggagcttctg tcaagacgag    300
ctcgttattg aaatggatga aaacaatggg cttccctgg tagaactgaa ccctcctaac    360
ccctgggact ctgatcccag gtctcctgaa gaattagctt ttggggaagt acagataaca    420
tatctcactc atgcctgcat ggacctcaag ttgggagaca gcgaatggt atttgaccct    480 tggttaattg gccctgcttt tgcccgagga tggtggttgc tacatgagcc tccatctgac    540
```

```
tggttggaga ggctgtgcaa agcagacctc atttatatca gccacatgca ctcagaccac    600
ctgagctacc ctaccctgaa gcagctttcc cagagacgac cagacattcc catttatgtt    660
ggcgacacag aaaggcctgt gttttggaac ctggatcaga gtggcgtcgg gttaactaac    720
atcaacgtgg ttccatttgg aatatggcaa caggtagaca aaagtctgcg gttcatgatc    780
ttgatggacg gcgttcatcc tgagatggac acatgcatta tcgtggagta caaaggtcat    840
aaaatactca acacagtgga ctgcaccaga cccaatgggg aaggcttcc tgagaaagtt     900
gctctaatga tgagtgattt cgcaggaggt gcatcaggct ttccaatgac tttcagtggt    960
ggaaaattta ctgaggaatg aaagcccag ttcattaagg ctgaaagaag aaagcttctg    1020
aattacaaag ctcagctggt gaaggacctg cagccccgaa tctactgtcc gtttgctggg   1080
tactttgtgg agtctcaccc atctgacaag tacattaagg aaacaaacac caaaaatgac   1140
ccaaatcagc tcaacaatct tatcaggaaa aactctgacg tggtgacatg gaccccacga   1200
cctggcgctg tcctcgacct tggcaggatg ctgaaggacc caacagacag caagggcatt   1260
gtggagcctc cagaggggac aaagatttac aaggattcct gggactttgg cccgtacctg   1320
gagatcttga attctgctgt cagagatgaa atcttctgtc attcatcctg gattaaagag   1380
tacttcacgt gggctggatt taagaattac aacctggtgg tcaggatgat tgaaacagat   1440
gaagatttca gccctttcc yggagggtac gactatctgg tggactttct agatttatcc     1500
tttccgaaag aaagacccag ccgggagcat ccttatgaag aaatccatag ccgggtggat   1560
gtcatcaggt acgtggtgaa gaacggcctg ctgtgggatr atctgtatat tggattccag   1620
acccgattgc tgcgggaccc tgatatatac catcatctgt tttggaatca ttttcagata   1680
aaactccctc taacaccacc caactggaag tcgttcctaa tgcactgtga ttag          1734
```

<210> SEQ ID NO 89
<211> LENGTH: 781
<212> TYPE: DNA
<213> ORGANISM: Felis catus
<220> FEATURE:
<223> OTHER INFORMATION: feline blood type B cytidine monophospho-N-
      acetylneuraminic acid hydroxylase (CMAH) genomic sequence
      including 5' UTR to exon 2

<400> SEQUENCE: 89

```
acggaggttc tatgggaaag ttaactcacg aagtagctag ctggtagaga tacaccgcgt     60
gacaggccgt gtgctcagcg acggggaggg agaatgtttg gaaaagcgtc cctatgtaaa    120
taaacggggc accgtgccgg gtgtaaggtt ctcatgttct acagaatggt agtgcgtatt    180
agcacgtgta ggcttgtccc ggggtggct ttggaggctt gacccaggct ggggtaggac     240
gactgggttc tatttgaacc tggagggtgg taaacatgac tagtggtgaa agttgaaccg    300
tgcttgtgag caaaaggatc agatctaaac gcaaagtgt gcaggtggga gcggcaggg     360
tgggcacctg gagcccaata ggatcctgcg tctgaagcaa cacagcagag gaagtggtgc    420
aacggaatca gtagtgaacc gcatgcatat gcatcctccg tctcatactt tgtgggagca    480
aacgagcaac cgaagctgaa cgagcaacca ccgtcctttc agaattccca gggagaggca    540
gctgcggacc atgggcaggc aagtgacagg ggcattgggt ctggaggaac ccgagaccaa    600
cactgagcaa gcagagcgtg catttccagg ggagcagcca agcctgggtc ctgcgaggga    660
ggggcttgag cctatcgtgg tggaaagagg ctttgagccg ccagtttcaa aagatgctct    720
cctaagtctt aacgttatta acctttcctc ccccaaatgt ctgcctttcc gtagcattga    780
a                                                                   781
```

<210> SEQ ID NO 90
<211> LENGTH: 763
<212> TYPE: DNA
<213> ORGANISM: Felis catus
<220> FEATURE:
<223> OTHER INFORMATION: feline blood type AB cytidine monophospho-N-
acetylneuraminic acid hydroxylase (CMAH) genomic sequence
including 5' UTR to exon 2

<400> SEQUENCE: 90

```
acggaggttc trtgggaaag ttaactcacg aagtagctag ctggtagaga tacaccgcgt      60
gacaggccgt gtgctcagcg acrggggaggg agaatgtttg gaaaagcgtc cctatgtaaa     120
taaacgggc accgtgccgg gtgtaaggtt ctcatgttct acagaatggt agtgcgtaty      180
agcacgtgta ggcttgtccc gggggtggct ttggaggctt gacccaggct ggggtaggac     240
gactgggttc tatttgaacc tggagggtgg taaacatgac tagtggtgaa agttgaaccg     300
tgcttgtgag caaaaggatc agatctaaac gcaraagtgt gcaggtggga gcgggcaggg     360
tgggcacctg gagcccaata ggatcctgcg tctgaagcaa cacagcagag gaagtggtgc     420
aacggaatca gtagtgaacc gcgtgcatat gcatcctccg tctcatactt tgtgggagca    480
aacgagcaac caccgtcctt tcagaattcc cagggagagg cagctgcgga ccatgggcag    540
gcaagtgaca gggcattgg gtctggagga acccgagacc aacactgagc aagcagagcg    600
tgcatttcca ggggagcagc caagcctggg tcctgcgagg gaggggcttg agcctatcgy    660
ggtggaaaga ggctttgagc cgccagtttc aaaagatgct ctcctaagtc ttaacgttat    720
taacctttcc tcccccaaat gtctgccttt ccgtagcatt gaa                      763
```

<210> SEQ ID NO 91
<211> LENGTH: 98
<212> TYPE: DNA
<213> ORGANISM: Artificial Sequence
<220> FEATURE:
<223> OTHER INFORMATION: synthetic feline blood type Ab CMAH cDNA 5' UTR
region

<400> SEQUENCE: 91

```
atatgcatcc tccgtctcat actttgtggg agcaaacgag caaccaccgt cctttcagaa      60
ttcccaggga gaggcagctg cggaccatgg gcagcatt                              98
```

<210> SEQ ID NO 92
<211> LENGTH: 123
<212> TYPE: DNA
<213> ORGANISM: Artificial Sequence
<220> FEATURE:
<223> OTHER INFORMATION: synthetic feline blood type Ab CMAH cDNA 5' UTR
region

<400> SEQUENCE: 92

```
cgcgtgcata tgcatcctcc gtctcatact ttgtgggagc aaacgagcaa ccgaagctga      60
acgagcaacc accgtccttt cagaattccc agggagaggc agctgcggac catgggcagc    120
att                                                                  123
```

<210> SEQ ID NO 93
<211> LENGTH: 133
<212> TYPE: DNA
<213> ORGANISM: Artificial Sequence
<220> FEATURE:
<223> OTHER INFORMATION: synthetic feline blood type B CMAH cDNA 5' UTR
region

<400> SEQUENCE: 93

```
agtagtgaac cgcgtgcata tgcatcctcc gtctcatact ttgtgggagc aaacgagcaa    60
ccgaagctga acgagcaacc accgtccttt cagaattccc agggagaggc agctgcggac   120
catgggcagc att                                                      133
```

<210> SEQ ID NO 94
<211> LENGTH: 80
<212> TYPE: DNA
<213> ORGANISM: Artificial Sequence
<220> FEATURE:
<223> OTHER INFORMATION: synthetic feline blood type AB CMAH cDNA 5' UTR
      region

<400> SEQUENCE: 94

```
atactttgtg ggagcaaagg agcaaccacc gtcctttcag aattcccagg gagaggcagc    60
tgcggaccat gggcagcatt                                                80
```

<210> SEQ ID NO 95
<211> LENGTH: 80
<212> TYPE: DNA
<213> ORGANISM: Artificial Sequence
<220> FEATURE:
<223> OTHER INFORMATION: synthetic feline blood type AB CMAH cDNA 5' UTR
      region

<400> SEQUENCE: 95

```
atactttgtg ggagcaaacg agcaaccacc gtccttccag aattcccagg gagaggcagc    60
tgcggaccat gggcagcatt                                                80
```

<210> SEQ ID NO 96
<211> LENGTH: 76
<212> TYPE: DNA
<213> ORGANISM: Artificial Sequence
<220> FEATURE:
<223> OTHER INFORMATION: synthetic feline blood type B or AB CMAH
      alternatively spliced cDNA 5' UTR region

<400> SEQUENCE: 96

```
agtttcaaaa gatgctctcc taagtcttaa cgttattaac ctttcctccc ccaaatgtct    60
gcctttccgt agcatt                                                    76
```

<210> SEQ ID NO 97
<211> LENGTH: 45
<212> TYPE: DNA
<213> ORGANISM: Artificial Sequence
<220> FEATURE:
<223> OTHER INFORMATION: synthetic feline blood type AB CMAH
      alternatively spliced cDNA 5' UTR region

<400> SEQUENCE: 97

```
gttattaacc tttcctcccc caaatgtctg cctttccgta gcatt                    45
```

<210> SEQ ID NO 98
<211> LENGTH: 76
<212> TYPE: DNA
<213> ORGANISM: Artificial Sequence
<220> FEATURE:
<223> OTHER INFORMATION: synthetic feline blood type AB CMAH
      alternatively spliced cDNA 5' UTR region

<400> SEQUENCE: 98

```
agtttcaaaa gatgctctcc taagtcttaa cgttattagc ctttcctccc ccaaatgtct    60
gcctttccgt agcatt                                                    76
```